(12) United States Patent
Smith et al.

(10) Patent No.: US 11,384,133 B2
(45) Date of Patent: Jul. 12, 2022

(54) ENGINEERING T CELL RECEPTORS

(71) Applicant: The Board of Trustees of the University of Illinois, Urbana, IL (US)

(72) Inventors: Sheena N. Smith, Champaign, IL (US); David M. Kranz, Champaign, IL (US)

(*) Notice: Subject to any disclaimer, the term of this patent is extended or adjusted under 35 U.S.C. 154(b) by 324 days.

(21) Appl. No.: 15/952,942

(22) Filed: Apr. 13, 2018

(65) Prior Publication Data
US 2018/0305434 A1  Oct. 25, 2018

Related U.S. Application Data

(62) Division of application No. 14/417,434, filed as application No. PCT/US2013/052283 on Jul. 26, 2013, now abandoned.

(60) Provisional application No. 61/676,373, filed on Jul. 27, 2012.

(51) Int. Cl.
| | | |
|---|---|---|
| *C12N 15/00* | (2006.01) | |
| *C07K 14/705* | (2006.01) | |
| *C07K 14/725* | (2006.01) | |
| *C12N 15/10* | (2006.01) | |

(52) U.S. Cl.
CPC .... *C07K 14/70503* (2013.01); *C07K 14/7051* (2013.01); *C12N 15/1037* (2013.01)

(58) Field of Classification Search
CPC .......... C07K 14/70503; C07K 14/7051; C12N 15/1037; A61P 35/00; C40B 40/02
See application file for complete search history.

(56) References Cited

U.S. PATENT DOCUMENTS

| | | | |
|---|---|---|---|
| 6,300,065 | B1 | 10/2001 | Kieke et al. |
| 6,759,243 | B2 | 7/2004 | Kranz et al. |
| 7,329,731 | B2 | 2/2008 | Jakobsen et al. |
| 8,741,814 | B2 | 6/2014 | Jakobsen et al. |
| 9,279,122 | B2 * | 3/2016 | Jakobsen ........... C12N 15/1037 |
| 2010/0009863 | A1 | 1/2010 | Himmler et al. |
| 2010/0113300 | A1 | 5/2010 | Jakobsen et al. |
| 2012/0252742 | A1 | 10/2012 | Kranz et al. |
| 2015/0191524 | A1 | 7/2015 | Smith et al. |

FOREIGN PATENT DOCUMENTS

| | | |
|---|---|---|
| WO | 01/55366 A1 | 8/2001 |
| WO | 2006103429 A2 | 10/2006 |
| WO | 2006/125962 A2 | 11/2006 |
| WO | 2007131092 A2 | 11/2007 |
| WO | 2008/039818 A2 | 4/2008 |
| WO | 2008042814 A2 | 4/2008 |

OTHER PUBLICATIONS

Aggen et al., (2011) Identification and engineering of human variable regions that allow expression of stable single-chain T cell receptors, Protein Engineering, Design, & Selection, 24:361-72.
Armstrong et al., (2008) Conformational changes and flexibility in T-cell receptor recognition of peptide-MHC complexes, Biochem. J., 415:183-96.
Boder et al., (2000) Yeast surface display for directed evolution of protein expression, affinity, and stability, Methods in Enzymology, 328: 430-444.
Chlewicki et al., (2005) High-affinity, peptide-specific T Cell receptors can be generated by mutations in CDR1, CDR2 or CDR3, J. Mol. Biol., 346:223-239.
Ding et al., (1999) Four A6-TCR/peptide/HLA-A2 structures that generate very different T cell signals are nearly identical, Immunity, 11:45-56.
Fleischer et al., (2004) Melanoma-reactive class I-restricted cytotoxic T cell clones are stimulated by dendritic cells loaded with synthetic peptides, but fail to respond to dendritic cells pulsed with melanoma-derived heat shock proteins in vitro, J. Immunol., 172:162-9.
Garboczi et al., (1996) Structure of the complex between human T-cell receptor, viral peptide and HLA-A2, Nature, 384:134-141.
Holler et al., (2003) TCRs with high affinity for foreign pMHC show self-reactivity, Nat Immunol., 4:55-62.
International Prelminary Report on Patentability (PCT/US2013/052283), dated Jan. 27, 2015.
International Search Report (PCT/US2013/052283), dated Nov. 26, 2013.
Kieke et al., (1999) Selection of functional T cell receptor mutants from a yeast surface-display library, Proc. Natl. Acad. Sci. U.S.A. 96:5651-6.
Li et al., (2005) Directed evolution of human T-cell receptors with picomolar affinities by phage display, Nat. Biotechnol., 23:349-54.
Manning et al., (1998) Alanine scanning mutagensis of an ala-beta T cell receptor: mapping the energy of antigen recognition, Immunity 8(4):413-425.
NCBI, Genbank accession No. 3QH3_A (Jan. 4, 2012).
NCBI, Genbank accession No. 3QH3_B (Jan. 4, 2012).
Richman and Kranz, (2007) Display, engineering, and applications of antigen-specific T cell receptors, Biomol. Eng., 24:361-73.
Richman et al., (2009) Structural features of T cell receptor variable regions that enhance domain stability and enable expression as single-chain Valpha Vbeta fragments, Mol. Immunol., 46:902-16.
Shusta et al., (1999) Yeast polypetide fusion surface display levels predict thermal stability soluble secretion efficiency, 292: 949-956.
Shusta et al., (2000) Directed evolution of a stable scaffold for T-cell receptor engineering, Nature Biotechnology, 18:754-749.

(Continued)

*Primary Examiner* — Mark Halvorson
(74) *Attorney, Agent, or Firm* — Womble Bond Dickinson (US) LLP; Cristin Howley Cowles; Kevin A. Fiala

(57) ABSTRACT

The use of model T cell receptors (TCRs) as scaffolds for in vitro engineering of novel specificities is provided. TCRs with de novo binding to a specific peptide-major histocompatibility complex (MHC) product can be isolated by: 1) mutagenizing a T cell receptor protein coding sequence to generate a variegated population of mutants (a library), 2) selection of the library of TCR mutants with the specific peptide-MHC, using a process of directed evolution and a "display" methodology (e.g., yeast, phage, mammalian cell) and the peptide-MHC ligand. The process can be repeated to identify TCR variants with improved affinity for the selecting peptide-MHC ligand.

8 Claims, 30 Drawing Sheets

Specification includes a Sequence Listing.

(56) References Cited

OTHER PUBLICATIONS

Smith, et al., "Plasticity in the Contribution of T Cell Receptor Variable Region Residues to Binding of Peptide-HLA-A2 Complexes" Journal of Molecular Biology, vol. 425, No. 22, Nov. 2013, pp. 4496-4507 (XP028751705).

Weber et al., (2005) Class II-restricted T cell receptor engineered in vitro for higher affinity retains peptide specificity and function, Proc. Natl. Acad. Sci. U.S.A. 102:19033-8.

Haidar, et al., "Structure-Based Design of a T-Cell Receptor Leads to Nearly 100-Fold Improvement in Binding Affinity for pepMHC," Proteins Structure Function and Bioinformatics, vol. 74, No. 4, Sep. 2, 2008, pp. 948-960 (XP002754943).

Smith, et al., "Changing the Peptide Specificity of a Human T-Cell Receptor by Directed Evolution," Nature Communications, vol. 5, Nov. 7, 2014, (XP002754940).

Stone, et al., "T Cell Receptor Engineering," Methods in Enzymology, vol. 503, Jan. 8, 2012, pp. 189-222 (XP8179207).

Hawse, et al., "Cutting Edge: Evidence for a Dynamically Driven T Cell Signaling Mechanism," Journal of Immunology, vol. 188, No. 12, Jun. 2012, pp. 5819-5823 (XP002754942).

Borbulevych et al., (2011) TCRs used in cancer gene therapy cross-react with MART-1/Melan-A tumor antigens via distinct mechanisms, J. Immunol., 187:2453-63.

Kessels, et al., "Changing T Cell Specificity by Retroviral T Cell Receptor Display," Proceedings of the National Academy of Sciences, vol. 97, Retrovuiral, No. 26, Dec. 19, 2000, p. 14578-14583 (XP002169376).

Pierce et al., (2010) Combinations of affinity-enhancing mutations in a T cell receptor reveal highly nonadditive effects within and between complementarity determining regions and chains, Biochemistry, 49:7050-9.

Marrack et al., (2008) Evolutionarily conserved amino acids that control TCR-MHC interaction, Annu. Rev. Immunol., 26:171-203.

Molloy et al., "Soluble T cell receptors: novel immunotherapies," Current Opinion in Pharmacology, (2005), vol. 5, pp. 438-443.

Schmidt et al., "Survivin is a shared tumor-associated antigen expressed in a broad variety of malignancies and Yecognized by specific cytotoxic T cells," Blood, (2003), vol. 102(2), pp. 571-576.

Garcia et al., Cell 2005, 122: 333-336.

Woolridge et al. (Journal of Biological Chemistry, 2012, 287:1168-1177).

Janeway et al. Immunology, 5th Ed., Garland Science, pp. 106-108, 117-118 and 260-263.

Goyarts et al., Molecular Immunology, 1998, 35:593-607.

Leisegang M, et al. MHC-restricted fratricide of human lymphocytes expressing survivin-specific transgenic T cell receptors. The Journal of clinical investigation. Nov. 1, 2010;120(11):3869-77.

Robbins P.F. et al. "Single and dual amino acid substitutions in TCR CDRs can enhance antigen-specific T cell functions." The Journal of Immunology, 2008; 180(9): 6116-6131).

\* cited by examiner

| Position | 1 | | | 2 | | | 3 | | | 4 | | | 5 | | |
|---|---|---|---|---|---|---|---|---|---|---|---|---|---|---|---|
| RD1 Library | N | N | S | N | N | S | N | N | S | N | N | N | N | N | S |
| | X | | | X | | | X | | | X | | | X | | |
| RD1-Tax-S4-1 | T | T | G | G | C | C | A | C | C | A | C | G | G | A | C |
| | L (3) | | | A (2) | | | T (2) | | | T (2) | | | D (1) | | |
| RD1-Tax-S4-2 | T | T | G | G | C | G | A | C | C | A | C | C | G | A | C |
| | L (3) | | | A (2) | | | T (2) | | | T (2) | | | D (1) | | |
| RD1-Tax-S4-3 | C | T | C | G | C | C | C | A | G | A | C | C | G | A | C |
| | L (3) | | | A (2) | | | Q (1) | | | T (2) | | | D (1) | | |
| RD1-Tax-S4-4 | T | T | G | G | C | G | A | C | C | A | C | C | G | A | C |
| | L (3) | | | A (2) | | | T (2) | | | T (2) | | | D (1) | | |
| RD1-Tax-S4-5 | C | T | C | G | C | C | C | A | G | A | C | C | G | A | C |
| | L (3) | | | A (2) | | | Q (1) | | | T (2) | | | D (1) | | |
| RD1-Tax-S4-6 | T | T | G | G | C | G | A | C | C | A | C | C | G | A | C |
| | L (3) | | | A (2) | | | T (2) | | | T (2) | | | D (1) | | |

*FIG. 10B*

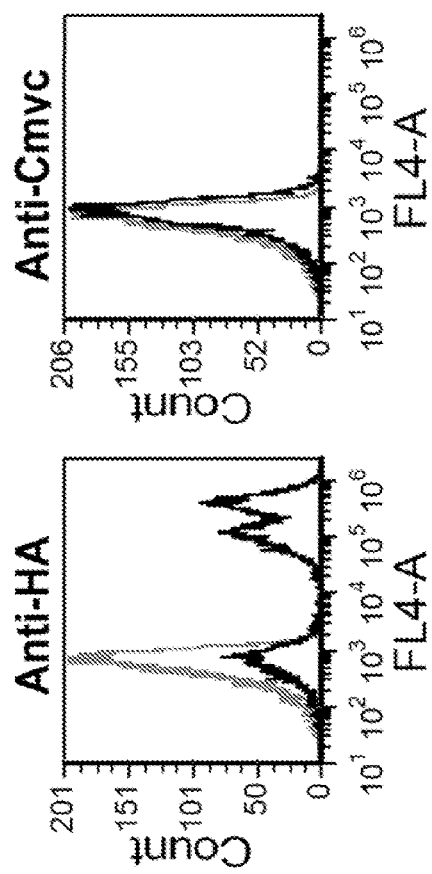
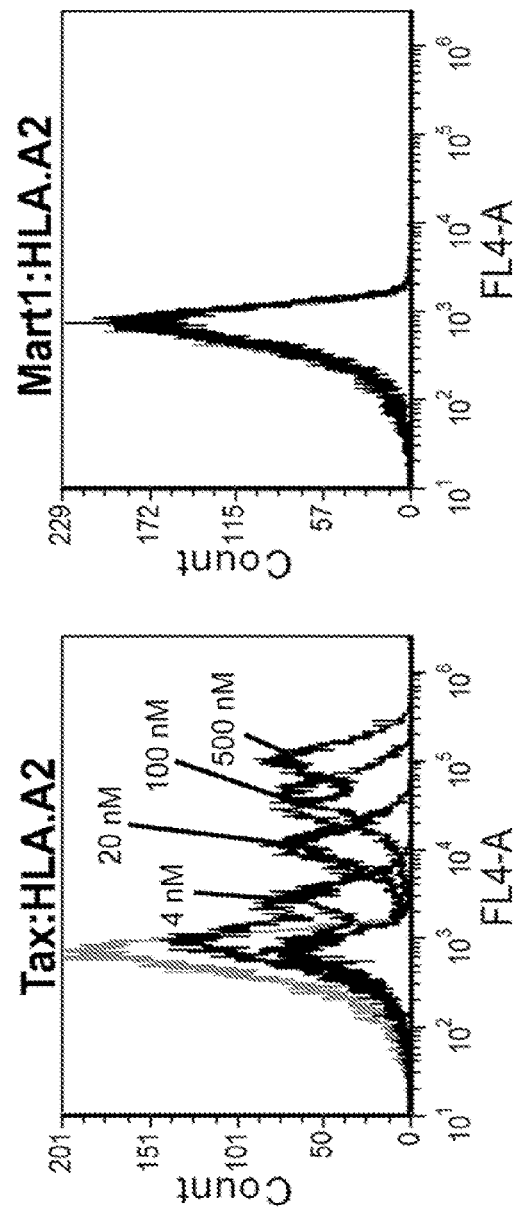
FIG. 11A
FIG. 11B
FIG. 11C
FIG. 11D

FIG. 12A

| Position | 1 | | | 2 | | | 3 | | | 4 | | | 5 | | |
|---|---|---|---|---|---|---|---|---|---|---|---|---|---|---|---|
| RD1 Library | N | N | S | N | N | S | N | N | S | N | N | N | N | N | S |
| | X | | | X | | | X | | | X | | | X | | |
| RD1-Mart1-S5-1 | T | G | G | G | G | C | A | C | G | A | A | G | T | A | C |
| | W (1) | | | G (2) | | | T (2) | | | K (1) | | | Y (1) | | |
| RD1-Mart1-S5-2 | T | G | G | G | G | C | A | C | G | A | A | G | T | A | C |
| | W (1) | | | G (2) | | | T (2) | | | K (1) | | | Y (1) | | |
| RD1-Mart1-S5-3 | T | G | G | G | G | C | A | C | G | A | A | G | T | A | C |
| | W (1) | | | G (2) | | | T (2) | | | K (1) | | | Y (1) | | |
| RD1-Mart1-S5-4 | T | G | G | G | G | C | A | C | G | A | A | G | T | A | C |
| | W (1) | | | G (2) | | | T (2) | | | K (1) | | | Y (1) | | |
| RD1-Mart1-S5-6 | T | G | G | G | G | C | A | C | G | A | A | G | T | A | C |
| | W (1) | | | G (2) | | | T (2) | | | K (1) | | | Y (1) | | |

Binding and specificity of soluble RD1-MART1^HIGH with peptide pulsed T2 cells

No peptide

Tax peptide (1 uM)

WT1 peptide (1 uM)

MART1 peptide (1 uM)

$K_{D,app} = 28 \pm 14$ nM

SEQUENCE LISTING

```
<160> NUMBER OF SEQ ID NOS: 75

<210> SEQ ID NO 1
<211> LENGTH: 113
<212> TYPE: PRT
<213> ORGANISM: Homo sapiens

<400> SEQUENCE: 1

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Thr Thr Asp Ser Trp
                85                  90                  95

Gly Lys Leu Gln Phe Gly Ala Gly Thr Gln Val Val Val Thr Pro Asp
                100                 105                 110
```

Ile

```
<210> SEQ ID NO 2
<211> LENGTH: 120
<212> TYPE: PRT
<213> ORGANISM: Homo sapiens

<400> SEQUENCE: 2
```

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Gly Ala Gly Ile Thr Asp Gln Gly Glu Val Pro Asn Gly Tyr
    50                  55                  60

Asn Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Ala Gly Gly Arg Pro Glu Gln Tyr Phe Gly Pro Gly Thr Arg Leu
            100                 105                 110

Thr Val Thr Glu Asp Leu Lys Asn
        115                 120

```
<210> SEQ ID NO 3
<211> LENGTH: 250
<212> TYPE: PRT
<213> ORGANISM: Homo sapiens

<400> SEQUENCE: 3
```

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Gln Lys Glu Val Glu Gln Asn
130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Gln Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr

```
                    195                 200                 205

Val Ser Leu Leu Ile Arg Asp Ser Gln Pro Ser Asp Ser Ala Thr Tyr
210                 215                 220

Leu Cys Ala Val Thr Thr Asp Ser Trp Gly Lys Leu Gln Phe Gly Ala
225                 230                 235                 240

Gly Thr Gln Val Val Val Thr Pro Asp Ile
                245                 250

<210> SEQ ID NO 4
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of the RD1 library
<220> FEATURE:
<221> NAME/KEY: MOD_RES
<222> LOCATION: (97)..(97)
<223> OTHER INFORMATION: Any naturally occurring amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (168)..(168)
<223> OTHER INFORMATION: Any amino acid
<220> FEATURE:
<221> NAME/KEY: MOD_RES
<222> LOCATION: (230)..(231)
<223> OTHER INFORMATION: Any amino acid

<400> SEQUENCE: 4

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
        50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Xaa Met Ser Xaa Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Xaa Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
210                 215                 220
```

```
Leu Cys Ala Val Thr Xaa Xaa Ser Trp Gly Lys Leu Gln Phe Gly Ala
225                 230                 235                 240

Gly Thr Gln Val Val Val Thr Pro Asp Ile
                245                 250

<210> SEQ ID NO 5
<211> LENGTH: 9
<212> TYPE: PRT
<213> ORGANISM: Human T cell lymphotrophic virus

<400> SEQUENCE: 5

Leu Leu Phe Gly Tyr Pro Val Tyr Val
1               5

<210> SEQ ID NO 6
<211> LENGTH: 9
<212> TYPE: PRT
<213> ORGANISM: Homo sapiens

<400> SEQUENCE: 6

Ala Ala Gly Ile Gly Ile Leu Thr Val
1               5

<210> SEQ ID NO 7
<211> LENGTH: 10
<212> TYPE: PRT
<213> ORGANISM: Homo sapiens

<400> SEQUENCE: 7

Glu Leu Ala Gly Ile Gly Ile Leu Thr Val
1               5                   10

<210> SEQ ID NO 8
<211> LENGTH: 9
<212> TYPE: PRT
<213> ORGANISM: Human immunodeficiency virus

<400> SEQUENCE: 8

Ser Leu Tyr Asn Thr Val Ala Thr Leu
1               5

<210> SEQ ID NO 9
<211> LENGTH: 9
<212> TYPE: PRT
<213> ORGANISM: Homo sapiens

<400> SEQUENCE: 9

Arg Met Phe Pro Asn Ala Pro Tyr Leu
1               5

<210> SEQ ID NO 10
<211> LENGTH: 9
<212> TYPE: PRT
<213> ORGANISM: Homo sapiens

<400> SEQUENCE: 10

Leu Thr Leu Gly Glu Phe Leu Lys Leu
1               5

<210> SEQ ID NO 11
<211> LENGTH: 9
<212> TYPE: PRT
<213> ORGANISM: Homo sapiens
```

```
<400> SEQUENCE: 11

Ser Leu Leu Met Trp Ile Thr Gln Cys
1               5

<210> SEQ ID NO 12
<211> LENGTH: 9
<212> TYPE: PRT
<213> ORGANISM: Homo sapiens

<400> SEQUENCE: 12

Ala Leu Trp Gly Pro Asp Ala Ala Ala
1               5

<210> SEQ ID NO 13
<211> LENGTH: 8
<212> TYPE: PRT
<213> ORGANISM: Homo sapiens

<400> SEQUENCE: 13

Val Leu Phe Tyr Leu Gly Gln Tyr
1               5

<210> SEQ ID NO 14
<211> LENGTH: 9
<212> TYPE: PRT
<213> ORGANISM: Hepatitis B virus

<400> SEQUENCE: 14

Phe Leu Leu Thr Arg Ile Leu Thr Ile
1               5

<210> SEQ ID NO 15
<211> LENGTH: 9
<212> TYPE: PRT
<213> ORGANISM: Homo sapiens

<400> SEQUENCE: 15

Lys Thr Trp Gly Gln Tyr Trp Gln Val
1               5

<210> SEQ ID NO 16
<211> LENGTH: 9
<212> TYPE: PRT
<213> ORGANISM: Homo sapiens

<400> SEQUENCE: 16

Ser Thr Ala Pro Pro Val His Asn Val
1               5

<210> SEQ ID NO 17
<211> LENGTH: 9
<212> TYPE: PRT
<213> ORGANISM: Homo sapiens

<400> SEQUENCE: 17

Phe Leu Trp Gly Pro Arg Ala Leu Val
1               5

<210> SEQ ID NO 18
<211> LENGTH: 9
<212> TYPE: PRT
<213> ORGANISM: Homo sapiens

<400> SEQUENCE: 18
```

-continued

```
Lys Ile Phe Gly Ser Leu Ala Phe Leu
1               5
```

<210> SEQ ID NO 19
<211> LENGTH: 9
<212> TYPE: PRT
<213> ORGANISM: Homo sapiens

<400> SEQUENCE: 19

```
Leu Glu Glu Lys Lys Gly Asn Tyr Val
1               5
```

<210> SEQ ID NO 20
<211> LENGTH: 9
<212> TYPE: PRT
<213> ORGANISM: Homo sapiens

<400> SEQUENCE: 20

```
Tyr Leu Ser Gly Ala Asn Leu Asn Leu
1               5
```

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 21

```
Gly Ser Ala Asp Asp Ala Lys Lys Asp Ala Ala Lys Lys Asp Gly Lys
1               5                   10                  15

Ser
```

<210> SEQ ID NO 22
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 22

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Ile Met Ser Glu Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
    130                 135                 140
```

```
Ser Gly Pro Leu Ser Val Pro Glu Gly Ala Ile Ala Ser Leu Asn Cys
145                 150                 155                 160

Thr Tyr Ser Asp Arg Gly Ser Ser Phe Phe Trp Tyr Arg Gln Tyr
            165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
            195                 200                 205

Val Ser Leu Leu Ile Arg Asp Ser Gln Pro Ser Asp Ser Ala Thr Tyr
        210                 215                 220

Leu Cys Ala Val Thr Pro Pro Ser Trp Gly Lys Leu Gln Phe Gly Ala
225                 230                 235                 240

Gly Thr Gln Val Val Val Thr Pro Asp Ile
            245                 250
```

<210> SEQ ID NO 23
<211> LENGTH: 250
<212> TYPE: PRT
<213> ORGANISM: Artificial Sequence
<220> FEATURE:
<223> OTHER INFORMATION: Description of Artificial Sequence: Synthetic amino acid sequence of clone from RD1 library

<400> SEQUENCE: 23

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
        50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Arg Met Ser Met Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Gln Lys Glu Val Glu Gln Asn
        130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Arg Ser Phe Phe Trp Tyr Arg Gln Tyr
            165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
            195                 200                 205

Val Ser Leu Leu Ile Arg Asp Ser Gln Pro Ser Asp Ser Ala Thr Tyr
        210                 215                 220

Leu Cys Ala Val Thr Pro Cys Ser Trp Gly Lys Leu Gln Phe Gly Ala
225                 230                 235                 240

Gly Thr Gln Val Val Val Thr Pro Asp Ile
            245                 250
```

<210> SEQ ID NO 24
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 24

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Ser Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
    130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Ala Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Ile Val Ser Trp Gly Lys Leu Gln Phe Gly Ala
225                 230                 235                 240

Gly Thr Gln Val Val Val Thr Pro Asp Ile
                245                 250

<210> SEQ ID NO 25
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 25

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
            50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                85                  90                  95

Thr Met Ser Arg Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Gln Lys Glu Val Glu Gln Asn
            130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Gly Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
            195                 200                 205

Val Ser Leu Leu Ile Arg Asp Ser Gln Pro Ser Asp Ser Ala Thr Tyr
            210                 215                 220

Leu Cys Ala Val Thr Ser Leu Ser Trp Gly Lys Leu Gln Phe Gly Ala
225                 230                 235                 240

Gly Thr Gln Val Val Val Thr Pro Asp Ile
                245                 250

<210> SEQ ID NO 26
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 26

Asn Ala Gly Val Thr Gln Thr Pro Lys Phe Gln Val Leu Lys Thr Gly
 1               5                  10                  15

Gln Ser Met Thr Leu Gln Cys Ala Gln Asp Met Asn His Glu Tyr Met
                20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
            50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                85                  90                  95

Ser Met Ser His Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Gln Lys Glu Val Glu Gln Asn
            130                 135                 140

Ser Gly Pro Leu Ser Val Pro Glu Gly Ala Ile Ala Ser Leu Asn Cys

```
                    145                 150                 155                 160
Thr Tyr Ser Asp Arg Gly Ser Phe Ser Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
            195                 200                 205

Val Ser Leu Leu Ile Arg Asp Ser Gln Pro Ser Asp Ser Ala Thr Tyr
        210                 215                 220

Leu Cys Ala Val Thr Leu His Ser Trp Gly Lys Leu Gln Phe Gly Ala
225                 230                 235                 240

Gly Thr Gln Val Val Val Thr Pro Asp Ile
                245                 250

<210> SEQ ID NO 27
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 27

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Ala Met Ser Gln Pro Glu Leu Tyr Phe Gly Pro Gly Thr Arg Leu Thr
            100                 105                 110

Val Thr Glu Asp Leu Ile Asn Gly Ser Ala Asp Asp Ala Lys Lys Asp
        115                 120                 125

Ala Ala Lys Lys Asp Gly Lys Ser Gln Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Asp Arg Gly Ser Tyr Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Asn Phe Ser Trp Gly Lys Leu Gln Phe Gly Ala Gly
225                 230                 235                 240

Thr Gln Val Val Val Thr Pro Asp Ile
                245
```

```
<210> SEQ ID NO 28
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 28

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Ser Met Ser Arg Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
    130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Ala Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Arg Thr Ser Trp Gly Lys Leu Gln Phe Gly Ala
225                 230                 235                 240

Gly Thr Gln Val Val Val Thr Pro Asp Ile
                245                 250

<210> SEQ ID NO 29
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 29

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45
```

```
Ser Val Gly Val Gly Ile Thr Asp Gln Gly Asp Val Pro Asp Gly Tyr
 50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                 85                  90                  95

Arg Met Ser Gln Gln Pro Glu Leu Tyr Phe Gly Pro Gly Thr Arg Leu
                100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Gln Lys Glu Val Glu Gln Asn
130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Trp Ser Phe Phe Trp Tyr Arg Gln Tyr
                165                 170                 175

Ser Gly Lys Ser Pro Glu Leu Ile Met Ser Ile Tyr Ser Asn Gly Asp
                180                 185                 190

Lys Glu Asp Gly Arg Phe Thr Ala Gln Leu Asn Lys Ala Ser Gln Tyr
            195                 200                 205

Val Ser Leu Leu Ile Arg Asp Ser Gln Pro Ser Asp Ser Ala Thr Tyr
210                 215                 220

Leu Cys Ala Val Thr Ser Cys Ser Trp Gly Lys Leu Gln Phe Gly Ala
225                 230                 235                 240

Gly Thr Gln Val Val Val Thr Pro Asp Ile
                245                 250

<210> SEQ ID NO 30
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 30

Asn Ala Gly Val Thr Gln Thr Pro Lys Phe Gln Val Leu Lys Thr Gly
 1                   5                  10                  15

Gln Ser Met Thr Leu Gln Cys Ala Gln Asp Met Asn His Glu Tyr Met
                 20                  25                  30

Ala Trp Tyr Arg Gln Asp Pro Gly Met Gly Leu Arg Leu Ile His Tyr
                 35                  40                  45

Ser Val Gly Val Gly Ile Thr Asp Gln Gly Asp Val Pro Asp Gly Tyr
 50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                 85                  90                  95

Tyr Met Ser Pro Gln Pro Glu Leu Tyr Phe Gly Pro Gly Thr Arg Leu
                100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Gln Lys Glu Val Glu Gln Asn
130                 135                 140

Ser Gly Pro Leu Ser Val Pro Glu Gly Ala Ile Ala Ser Leu Asn Cys
145                 150                 155                 160
```

Thr Tyr Ser Asp Arg Gly Ser Asn Ser Phe Phe Trp Tyr Arg Gln Tyr
              165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Phe Leu Ser Trp Gly Lys Leu Gln Phe Gly Ala
225                 230                 235                 240

Gly Thr Gln Val Val Val Thr Pro Asp Ile
                245                 250

<210> SEQ ID NO 31
<211> LENGTH: 250
<212> TYPE: PRT
<213> ORGANISM: Artificial Sequence
<220> FEATURE:
<223> OTHER INFORMATION: Description of Artificial Sequence: Synthetic
      amino acid sequence of clone from RD1 library

<400> SEQUENCE: 31

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Leu Gln Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Gln Lys Glu Val Glu Gln Asn
    130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Gln Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Arg Ala Ser Trp Gly Lys Leu Gln Phe Gly Ala
225                 230                 235                 240

Gly Thr Gln Val Val Val Thr Pro Asp Ile
                245                 250

-continued

```
<210> SEQ ID NO 32
<211> LENGTH: 250
<212> TYPE: PRT
<213> ORGANISM: Artificial Sequence
<220> FEATURE:
<223> OTHER INFORMATION: Description of Artificial Sequence: Synthetic
      RD1-Tax-S4-1 clone sequence

<400> SEQUENCE: 32

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
    130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Thr Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
    195                 200                 205

Val Ser Leu Leu Ile Arg Asp Ser Gln Pro Ser Asp Ser Ala Thr Tyr
    210                 215                 220

Leu Cys Ala Val Thr Thr Asp Ser Trp Gly Lys Leu Gln Phe Gly Ala
225                 230                 235                 240

Gly Thr Gln Val Val Val Thr Pro Asp Ile
                245                 250

<210> SEQ ID NO 33
<211> LENGTH: 250
<212> TYPE: PRT
<213> ORGANISM: Artificial Sequence
<220> FEATURE:
<223> OTHER INFORMATION: Description of Artificial Sequence: Synthetic
      RD1-Mart1-S5-5 clone sequence

<400> SEQUENCE: 33

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
```

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Trp Met Ser Gly Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
                115                 120                 125

Asp Ala Ala Lys Lys Asp Gly Lys Ser Gln Lys Glu Val Glu Gln Asn
        130                 135                 140

Ser Gly Pro Leu Ser Val Pro Glu Gly Ala Ile Ala Ser Leu Asn Cys
145                 150                 155                 160

Thr Tyr Ser Asp Arg Gly Ser Thr Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
210                 215                 220

Leu Cys Ala Val Thr Lys Tyr Ser Trp Gly Lys Leu Gln Phe Gly Ala
225                 230                 235                 240

Gly Thr Gln Val Val Val Thr Pro Asp Ile
                245                 250

<210> SEQ ID NO 34
<211> LENGTH: 250
<212> TYPE: PRT
<213> ORGANISM: Artificial Sequence
<220> FEATURE:
<223> OTHER INFORMATION: Description of Artificial Sequence: Synthetic
      RD1-Mart1-High clone sequence

<400> SEQUENCE: 34

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
        50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Trp Met Ala Gly Gly Val Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Lys Glu Val Glu Gln Asn
        130                 135                 140

Ser Gly Pro Leu Ser Val Pro Glu Gly Ala Ile Ala Ser Leu Asn Cys
145                 150                 155                 160

```
Thr Tyr Ser Asp Arg Gly Ser Thr Ser Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Lys Tyr Ser Trp Gly Lys Leu Gln Phe Gly Ala
225                 230                 235                 240

Gly Thr Gln Val Val Thr Pro Asp Ile
                245                 250

<210> SEQ ID NO 35
<211> LENGTH: 249
<212> TYPE: PRT
<213> ORGANISM: Artificial Sequence
<220> FEATURE:
<223> OTHER INFORMATION: Description of Artificial Sequence: Synthetic
      degenerate amino acid sequence for RD2 library
<220> FEATURE:
<221> NAME/KEY: MOD_RES
<222> LOCATION: (97)..(97)
<223> OTHER INFORMATION: Any amino acid
<220> FEATURE:
<221> NAME/KEY: MISC_FEATURE
<222> LOCATION: (98)..(101)
<223> OTHER INFORMATION: This region may encompass 'Ala Gly Gly Arg' or
      'Met Ser Ala Gln'
<220> FEATURE:
<221> NAME/KEY: MOD_RES
<222> LOCATION: (163)..(163)
<223> OTHER INFORMATION: Any amino acid
<220> FEATURE:
<221> NAME/KEY: MOD_RES
<222> LOCATION: (165)..(165)
<223> OTHER INFORMATION: Any amino acid
<220> FEATURE:
<221> NAME/KEY: MOD_RES
<222> LOCATION: (167)..(167)
<223> OTHER INFORMATION: Gln or Thr
<220> FEATURE:
<221> NAME/KEY: MOD_RES
<222> LOCATION: (231)..(232)
<223> OTHER INFORMATION: Any amino acid
<220> FEATURE:
<223> OTHER INFORMATION: See specification as filed for detailed
      description of substitutions and preferred embodiments

<400> SEQUENCE: 35

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Xaa Xaa Xaa Xaa Xaa Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
```

```
            115                 120                 125
Asp Ala Ala Lys Lys Asp Gly Lys Ser Lys Glu Val Glu Gln Asn Ser
        130                 135                 140

Gly Pro Leu Ser Val Pro Glu Gly Ala Ile Ala Ser Leu Asn Cys Thr
145                 150                 155                 160

Tyr Ser Xaa Arg Xaa Ser Xaa Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
                195                 200                 205

Ser Leu Leu Ile Arg Asp Ser Gln Pro Ser Asp Ser Ala Thr Tyr Leu
        210                 215                 220

Cys Ala Val Thr Thr Asp Xaa Xaa Gly Lys Leu Gln Phe Gly Ala Gly
225                 230                 235                 240

Thr Gln Val Val Val Thr Pro Asp Ile
                245
```

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD2 library

<400> SEQUENCE: 36

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Cys Arg Met Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220
```

```
Cys Ala Val Thr Thr Asp Tyr Ser Gly Lys Leu Gln Phe Gly Ala Gly
225                 230                 235                 240

Thr Gln Val Val Val Thr Pro Asp Ile
                245
```

<210> SEQ ID NO 37
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD2 library

<400> SEQUENCE: 37

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Asp Ala Gly Gly Arg Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Pro Arg Arg Ser Thr Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
    195                 200                 205

Ser Leu Leu Ile Arg Asp Ser Gln Pro Ser Asp Ser Ala Thr Tyr Leu
    210                 215                 220

Cys Ala Val Thr Thr Asp Thr Asn Gly Lys Leu Gln Phe Gly Ala Gly
225                 230                 235                 240

Thr Gln Val Val Val Thr Pro Asp Ile
                245
```

<210> SEQ ID NO 38
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD2 library

<400> SEQUENCE: 38

```
Asn Ala Gly Val Thr Gln Thr Pro Lys Phe Gln Val Leu Lys Thr Gly
1               5                   10                  15
```

```
Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
 50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                85                  90                  95

Cys Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Lys Glu Val Glu Gln Asn Ser
        130                 135                 140

Gly Pro Leu Ser Val Pro Glu Gly Ala Ile Ala Ser Leu Asn Cys Thr
145                 150                 155                 160

Tyr Ser Cys Arg Phe Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
 210                 215                 220

Cys Ala Val Thr Thr Asp Glu Val Gly Lys Leu Gln Phe Gly Ala Gly
225                 230                 235                 240

Thr Gln Val Val Val Thr Pro Asp Ile
                245

<210> SEQ ID NO 39
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD2 library

<400> SEQUENCE: 39

Asn Ala Gly Val Thr Gln Thr Pro Lys Phe Gln Val Leu Lys Thr Gly
 1               5                  10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
 50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125
```

Asp Ala Ala Lys Lys Asp Gly Lys Ser Lys Glu Val Glu Gln Asn Ser
            130                 135                 140

Gly Pro Leu Ser Val Pro Glu Gly Ala Ile Ala Ser Leu Asn Cys Thr
145                 150                 155                 160

Tyr Ser Thr Arg Tyr Ser Thr Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
            195                 200                 205

Ser Leu Leu Ile Arg Asp Ser Gln Pro Ser Asp Ser Ala Thr Tyr Leu
            210                 215                 220

Cys Ala Val Thr Thr Asp Pro Leu Gly Lys Leu Gln Phe Gly Ala Gly
225                 230                 235                 240

Thr Gln Val Val Val Thr Pro Asp Ile
                245

<210> SEQ ID NO 40
<211> LENGTH: 249
<212> TYPE: PRT
<213> ORGANISM: Artificial Sequence
<220> FEATURE:
<223> OTHER INFORMATION: Description of Artificial Sequence: Synthetic
      amino acid sequence of clone from RD2 library

<400> SEQUENCE: 40

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
        50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Arg Ala Gly Gly Arg Pro Glu Leu Tyr Phe Gly Pro Gly Thr Arg Leu
            100                 105                 110

Thr Val Thr Glu Asp Leu Ile Asn Gly Ser Ala Asp Ala Lys Lys
            115                 120                 125

Asp Ala Ala Lys Lys Asp Gly Lys Ser Lys Glu Val Glu Gln Asn Ser
            130                 135                 140

Gly Pro Leu Ser Val Pro Glu Gly Ala Ile Ala Ser Leu Asn Cys Thr
145                 150                 155                 160

Tyr Ser Asn Arg Ser Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
            195                 200                 205

Ser Leu Leu Ile Arg Asp Ser Gln Pro Ser Asp Ser Ala Thr Tyr Leu
            210                 215                 220

Cys Ala Val Thr Thr Asp Asn His Gly Lys Leu Gln Phe Gly Ala Gly

```
                    225                 230                 235                 240

Thr Gln Val Val Val Thr Pro Asp Ile
                245

<210> SEQ ID NO 41
<211> LENGTH: 249
<212> TYPE: PRT
<213> ORGANISM: Artificial Sequence
<220> FEATURE:
<223> OTHER INFORMATION: Description of Artificial Sequence: Synthetic
      RD2-Mart1-S3-3 clone sequence

<400> SEQUENCE: 41

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Met Ala Gly Gly Arg Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Ser Arg His Ser Thr Ser Phe Ser Trp Tyr Arg Gln Tyr Pro
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Thr Asp Arg Ser Gly Lys Leu Gln Phe Gly Ala Gly
225                 230                 235                 240

Thr Gln Val Val Val Thr Pro Asp Ile
                245

<210> SEQ ID NO 42
<211> LENGTH: 249
<212> TYPE: PRT
<213> ORGANISM: Artificial Sequence
<220> FEATURE:
<223> OTHER INFORMATION: Description of Artificial Sequence: Synthetic
      RD2-Mart1-S3-4 clone sequence

<400> SEQUENCE: 42

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
```

```
            20                  25                  30
Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
            50                  55                  60

Lys Val Ser Arg Ser Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Met Ala Gly Gly Arg Pro Glu Leu Tyr Phe Gly Pro Gly Thr Arg Leu
                100                 105                 110

Thr Val Thr Glu Asp Leu Ile Asn Gly Ser Ala Asp Ala Lys Lys
            115                 120                 125

Asp Ala Ala Lys Lys Asp Gly Lys Ser Lys Glu Val Glu Gln Asn Ser
        130                 135                 140

Gly Pro Leu Ser Val Pro Glu Gly Ala Ile Ala Ser Leu Asn Cys Thr
145                 150                 155                 160

Tyr Ser Ser Arg His Ser Gln Ser Phe Ser Trp Tyr Arg Gln Tyr Pro
                165                 170                 175

Gly Lys Ser Pro Glu Leu Ile Met Ser Ile Tyr Ser Asn Gly Asp Lys
                180                 185                 190

Glu Asp Gly Arg Phe Thr Ala Gln Leu Asn Lys Ala Ser Gln Tyr Val
            195                 200                 205

Ser Leu Leu Ile Arg Asp Ser Gln Pro Ser Asp Ser Ala Thr Tyr Leu
        210                 215                 220

Cys Ala Val Thr Thr Asp Leu Trp Gly Lys Leu Gln Phe Gly Ala Gly
225                 230                 235                 240

Thr Gln Val Val Val Thr Pro Asp Ile
                245

<210> SEQ ID NO 43
<211> LENGTH: 247
<212> TYPE: PRT
<213> ORGANISM: Artificial Sequence
<220> FEATURE:
<223> OTHER INFORMATION: Description of Artificial Sequence: Synthetic
      Clone T1-S18.45 amino acid sequence

<400> SEQUENCE: 43

Glu Ala Gly Val Thr Gln Phe Pro Ser His Ser Val Ile Glu Lys Gly
1               5                   10                  15

Gln Thr Val Thr Leu Arg Cys Asp Pro Ile Ser Gly His Asp Asn Leu
            20                  25                  30

Tyr Trp Tyr Arg Arg Val Met Gly Lys Glu Ile Lys Phe Leu Leu His
            35                  40                  45

Phe Val Lys Glu Ser Lys Gln Asp Glu Ser Gly Met Pro Asn Asn Arg
        50                  55                  60

Phe Leu Ala Glu Arg Thr Gly Gly Thr Tyr Ser Thr Leu Lys Ile Gln
65                  70                  75                  80

Pro Ala Glu Leu Glu Asp Ser Gly Val Tyr Phe Cys Ala Ser Ser His
                85                  90                  95

Ala Gly Leu Gly Val Glu Gln Tyr Phe Gly Pro Gly Thr Arg Leu Thr
            100                 105                 110

Val Thr Glu Asp Leu Lys Asn Gly Ser Ala Asp Asp Ala Lys Glu Asp
            115                 120                 125
```

```
Ala Ala Lys Lys Asp Gly Lys Ser Gln Lys Glu Val Glu Gln Asn Ser
        130                 135                 140

Gly Pro Leu Ser Val Pro Glu Gly Ala Ile Ala Ser Leu Asn Cys Thr
145                 150                 155                 160

Tyr Ser Asp Arg Gly Ser Gln Ser Phe Phe Trp Tyr Arg Gln Tyr Pro
                165                 170                 175

Gly Lys Ser Pro Glu Leu Ile Met Ser Ile Tyr Ser Asn Gly Asp Lys
                180                 185                 190

Glu Asp Gly Arg Phe Thr Ala Gln Leu Asn Lys Ala Ser Gln Tyr Val
                195                 200                 205

Ser Leu Leu Ile Arg Asp Ser Arg Pro Ser Asp Ser Ala Thr Tyr Leu
210                 215                 220

Cys Ala Val Ser Ser Ser Asp Phe Leu Met Phe Gly Asp Gly Thr Gln
225                 230                 235                 240

Leu Val Val Lys Pro Asn Ile
                245

<210> SEQ ID NO 44
<211> LENGTH: 4
<212> TYPE: PRT
<213> ORGANISM: Homo sapiens

<400> SEQUENCE: 44

Ala Gly Gly Arg
1

<210> SEQ ID NO 45
<211> LENGTH: 4
<212> TYPE: PRT
<213> ORGANISM: Homo sapiens

<400> SEQUENCE: 45

Met Ser Ala Gln
1

<210> SEQ ID NO 46
<211> LENGTH: 9
<212> TYPE: PRT
<213> ORGANISM: Homo sapiens

<400> SEQUENCE: 46

Ala Ser Asn Glu Asn Met Asp Ala Met
1               5

<210> SEQ ID NO 47
<211> LENGTH: 9
<212> TYPE: PRT
<213> ORGANISM: Homo sapiens

<400> SEQUENCE: 47

Ala Ser Asn Glu Asn Met Glu Thr Met
1               5

<210> SEQ ID NO 48
<211> LENGTH: 9
<212> TYPE: DNA
<213> ORGANISM: Artificial Sequence
<220> FEATURE:
<223> OTHER INFORMATION: Description of Artificial Sequence: Synthetic
      5' region of RD1 gene optimized for yeast and E. coli

<400> SEQUENCE: 48
``` tctgctagc                                                              9

<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence: Synthetic
      3' region of RD1 gene optimized for yeast and E. coli

<400> SEQUENCE: 49
ctcgagatct ga                                                         12

<210> SEQ ID NO 50
<211> LENGTH: 85
<212> TYPE: DNA
<213> ORGANISM: Artificial Sequence
<220> FEATURE:
<223> OTHER INFORMATION: Description of Artificial Sequence: Synthetic
      forward primer used to add pCT302 overhangs

<400> SEQUENCE: 50
caggctagtg gtggtggtgg ttctggtggt ggtggttctg gtggtggtgg ttctgctagc    60
aatgctggtg taacacaaac gccaa                                          85

<210> SEQ ID NO 51
<211> LENGTH: 75
<212> TYPE: DNA
<213> ORGANISM: Artificial Sequence
<220> FEATURE:
<223> OTHER INFORMATION: Description of Artificial Sequence: Synthetic
      reverse primer used to add pCT302 overhangs

<400> SEQUENCE: 51
ggaacaaagt cgattttgtt acatctacac tgttgttaac agatctcgag tcattataaa    60
tcttcttcag agatc                                                     75

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      forward primer to generate the CDR3 1 library (Splice 4L)

<400> SEQUENCE: 52
ggcagcccca taaacacaca gtat                                           24

<210> SEQ ID NO 53
<211> LENGTH: 63
<212> TYPE: DNA
<213> ORGANISM: Artificial Sequence
<220> FEATURE:
<223> OTHER INFORMATION: Description of Artificial Sequence: Synthetic
      reverse primer to generate a CDR3 1 library (Splice 4L)

<400> SEQUENCE: 53
cggacgggaa gcgcagaaat acactgaggt ttgagaaggt gcagcgctta acagacgcag    60
cgg                                                                  63

<210> SEQ ID NO 54
<211> LENGTH: 79
<212> TYPE: DNA
<213> ORGANISM: Artificial Sequence
<220> FEATURE:

```
<223> OTHER INFORMATION: Description of Artificial Sequence: Synthetic
      forward primer to generate a CDR3 1 library (T7)
<220> FEATURE:
<221> NAME/KEY: modified_base
<222> LOCATION: (31)..(32)
<223> OTHER INFORMATION: a, c, t or g
<220> FEATURE:
<221> NAME/KEY: modified_base
<222> LOCATION: (34)..(35)
<223> OTHER INFORMATION: a, c, t or g
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g

<400> SEQUENCE: 54
acctcagtgt atttctgcgc ttcccgtccg nnknnknnkn nknnkcagcc tgaactgtac    60
tttggtccag gcactagac                                                79

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer to generate a CDR3 1 library (T7)

<400> SEQUENCE: 55
taatacgact cactataggg                                                20

<210> SEQ ID NO 56
<211> LENGTH: 63
<212> TYPE: DNA
<213> ORGANISM: Artificial Sequence
<220> FEATURE:
<223> OTHER INFORMATION: Description of Artificial Sequence: Synthetic
      forward primer to generate a CDR3 2 library

<400> SEQUENCE: 56
cggacgggaa gcgcagaaat acactgaggt ttgagaaggt gcagcgctta acagacgcag    60
cgg                                                                 63

<210> SEQ ID NO 57
<211> LENGTH: 85
<212> TYPE: DNA
<213> ORGANISM: Artificial Sequence
<220> FEATURE:
<223> OTHER INFORMATION: Description of Artificial Sequence: Synthetic
      primer to generate a CDR3beta2 library
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
```

```
<222> LOCATION: (46)..(47)
<223> OTHER INFORMATION: a, c, t or g
<220> FEATURE:
<221> NAME/KEY: modified_base
<222> LOCATION: (49)..(50)
<223> OTHER INFORMATION: a, c, t or g

<400> SEQUENCE: 57
acctcagtgt atttctgcgc ttcccgtccg ggttggnnkn nknnknnknn kgaactgtac    60
tttggtccag gcactagact gaccg                                         85

<210> SEQ ID NO 58
<211> LENGTH: 71
<212> TYPE: DNA
<213> ORGANISM: Artificial Sequence
<220> FEATURE:
<223> OTHER INFORMATION: Description of Artificial Sequence: Synthetic
      primer to generate a CDR3alpha library

<400> SEQUENCE: 58
cgtaaccgcg cacaagtatg tggccgaatc ggaaggctgg gagtcacgaa tcagcaaact    60
aacatactgg c                                                        71

<210> SEQ ID NO 59
<211> LENGTH: 82
<212> TYPE: DNA
<213> ORGANISM: Artificial Sequence
<220> FEATURE:
<223> OTHER INFORMATION: Description of Artificial Sequence: Synthetic
      primer to generate a CDR3alpha library
<220> FEATURE:
<221> NAME/KEY: modified_base
<222> LOCATION: (34)..(35)
<223> OTHER INFORMATION: a, c, t or g
<220> FEATURE:
<221> NAME/KEY: modified_base
<222> LOCATION: (37)..(38)
<223> OTHER INFORMATION: a, c, t or g
<220> FEATURE:
<221> NAME/KEY: modified_base
<222> LOCATION: (40)..(41)
<223> OTHER INFORMATION: a, c, t or g
<220> FEATURE:
<221> NAME/KEY: modified_base
<222> LOCATION: (43)..(44)
<223> OTHER INFORMATION: a, c, t or g
<220> FEATURE:
<221> NAME/KEY: modified_base
<222> LOCATION: (46)..(47)
<223> OTHER INFORMATION: a, c, t or g

<400> SEQUENCE: 59
tccgattcgg ccacatactt gtgcgcggtt acgnnknnkn nknnknnkaa actgcaattt    60
ggtgcgggca cccaggttgt gg                                            82

<210> SEQ ID NO 60
<211> LENGTH: 150
<212> TYPE: DNA
<213> ORGANISM: Artificial Sequence
<220> FEATURE:
<223> OTHER INFORMATION: Description of Artificial Sequence: Synthetic
      flanking N-terminal DNA from yeast codon optimized RD2 gene

<400> SEQUENCE: 60
ggcagcccca taaacacaca gtatgttttt aaggacaata gctcgacgat tgaaggtaga    60
tacccatacg acgttccaga ctacgctctg caggctagtg gtggtggtgg ttctggtggt   120
ggtggttctg gtggtggtgg ttctgctagc                                   150
```

<210> SEQ ID NO 61
<211> LENGTH: 346
<212> TYPE: DNA
<213> ORGANISM: Artificial Sequence
<220> FEATURE:
<223> OTHER INFORMATION: Description of Artificial Sequence: Synthetic
      flanking C-terminal DNA from yeast codon optimized RD2 gene

<400> SEQUENCE: 61

```
ctcgagatct gttaacaaca gtgtagatgt aacaaaatcg actttgttcc cactgtactt      60
ttagctcgta caaaatacaa tatactttc atttctccgt aaacaacatg ttttcccatg     120
taatatcctt ttctattttt cgttccgtta ccaactttac atatacttta tatagctatt     180
cacttctata cactaaaaaa ctaagacaat tttaattttg ctgcctgcca tatttcaatt     240
tgttataaat tcctataatt tatcctatta gtagctaaaa aaagatgaat gtgaatcgaa     300
tcctaagaga attgagctcc aattcgccct atagtgagtc gtatta                    346
```

<210> SEQ ID NO 62
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (168)..(168)
<223> OTHER INFORMATION: Any amino acid
<220> FEATURE:
<221> NAME/KEY: MOD_RES
<222> LOCATION: (230)..(231)
<223> OTHER INFORMATION: Any amino acid

<400> SEQUENCE: 62

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Xaa Met Ser Xaa Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Gln Leu Glu Val Glu Gln Asn
    130                 135                 140

Ser Gly Pro Leu Ser Val Pro Glu Gly Ala Ile Ala Ser Leu Asn Cys
```

```
145                 150                 155                 160
Thr Tyr Ser Asp Arg Gly Ser Xaa Ser Phe Phe Trp Tyr Arg Gln Tyr
                165                 170                 175

Ser Gly Lys Ser Pro Glu Leu Ile Met Ser Ile Tyr Ser Asn Gly Asp
            180                 185                 190

Lys Glu Asp Gly Arg Phe Thr Ala Gln Leu Asn Lys Ala Ser Gln Tyr
        195                 200                 205

Val Ser Leu Leu Ile Arg Asp Ser Gln Pro Ser Asp Ser Ala Thr Tyr
    210                 215                 220

Leu Cys Ala Val Thr Xaa Xaa Ser Trp Gly Lys Leu Gln Phe Gly Ala
225                 230                 235                 240

Gly Thr Gln Val Val Val Thr Pro Asp Ile Glu Gln Lys Leu Ile Ser
                245                 250                 255

Glu Glu Asp Leu
            260

<210> SEQ ID NO 63
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Any amino acid
<220> FEATURE:
<221> NAME/KEY: MISC_FEATURE
<222> LOCATION: (98)..(101)
<223> OTHER INFORMATION: This region may encompass 'Ala Gly Gly Arg' or
      'Met Ser Ala Gln'
<220> FEATURE:
<221> NAME/KEY: MOD_RES
<222> LOCATION: (163)..(163)
<223> OTHER INFORMATION: Any amino acid
<220> FEATURE:
<221> NAME/KEY: MOD_RES
<222> LOCATION: (165)..(165)
<223> OTHER INFORMATION: Any amino acid
<220> FEATURE:
<221> NAME/KEY: MOD_RES
<222> LOCATION: (167)..(167)
<223> OTHER INFORMATION: Gln or Thr
<220> FEATURE:
<221> NAME/KEY: MOD_RES
<222> LOCATION: (231)..(232)
<223> OTHER INFORMATION: Any amino acid
<220> FEATURE:
<223> OTHER INFORMATION: See specification as filed for detailed
      description of substitutions and preferred embodiments

<400> SEQUENCE: 63

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95
```

Xaa Xaa Xaa Xaa Xaa Pro Glu Leu Tyr Phe Gly Pro Gly Thr Arg Leu
                100                 105                 110

Thr Val Thr Glu Asp Leu Ile Asn Gly Ser Ala Asp Ala Lys Lys
            115                 120                 125

Asp Ala Ala Lys Lys Asp Gly Lys Ser Lys Glu Val Glu Gln Asn Ser
130                 135                 140

Gly Pro Leu Ser Val Pro Glu Gly Ala Ile Ala Ser Leu Asn Cys Thr
145                 150                 155                 160

Tyr Ser Xaa Arg Xaa Ser Xaa Ser Phe Phe Trp Tyr Arg Gln Tyr Ser
                165                 170                 175

Gly Lys Ser Pro Glu Leu Ile Met Ser Ile Tyr Ser Asn Gly Asp Lys
                180                 185                 190

Glu Asp Gly Arg Phe Thr Ala Gln Leu Asn Lys Ala Ser Gln Tyr Val
                195                 200                 205

Ser Leu Leu Ile Arg Asp Ser Gln Pro Ser Asp Ser Ala Thr Tyr Leu
                210                 215                 220

Cys Ala Val Thr Thr Asp Xaa Xaa Gly Lys Leu Gln Phe Gly Ala Gly
225                 230                 235                 240

Thr Gln Val Val Val Thr Pro Asp Ile Glu Gln Lys Leu Ile Ser Glu
                245                 250                 255

Glu Asp Leu

<210> SEQ ID NO 64
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Ala Met Ser

<210> SEQ ID NO 65
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Pro Glu Leu Tyr Phe Gly Pro Gly Thr Arg Leu Thr Val Thr Glu
1               5                   10                  15

Asp Leu Ile Asn Gly Ser Ala Asp Asp Ala Lys Lys Asp Ala Ala Lys

```
                20                  25                  30

Lys Asp Gly Lys Ser Gln Lys Glu Val Glu Gln Asn Ser Gly Pro Leu
                35                  40                  45

Ser Val Pro Glu Gly Ala Ile Ala Ser Leu Asn Cys Thr Tyr Ser Asp
        50                  55                  60

Arg Gly Ser Tyr Ser Phe Phe Trp Tyr Arg Gln Tyr Ser Gly Lys Ser
65                  70                  75                  80

Pro Glu Leu Ile Met Ser Ile Tyr Ser Asn Gly Asp Lys Glu Asp Gly
                85                  90                  95

Arg Phe Thr Ala Gln Leu Asn Lys Ala Ser Gln Tyr Val Ser Leu Leu
            100                 105                 110

Ile Arg Asp Ser Gln Pro Ser Asp Ser Ala Thr Tyr Leu Cys Ala Val
        115                 120                 125

Thr Asn Phe Ser Trp Gly Lys Leu Gln Phe Gly Ala Gly Thr Gln Val
    130                 135                 140

Val Val Thr Pro Asp Ile
145                 150

<210> SEQ ID NO 66
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
                20                  25                  30

Ala Trp Tyr Arg Gln Asp Pro Gly Met Gly Leu Arg Leu Ile His Tyr
            35                  40                  45

Ser Val Gly Val Gly Ile Thr Asp Gln Gly Asp Val Pro Asp Gly Tyr
        50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Asp Arg Gly Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220
```

```
Cys Ala Val Thr Thr Asp Ser Trp Gly Lys Leu Gln Phe Gly Ala Gly
225                 230                 235                 240

Thr Gln Val Val Val Thr Pro Asp Ile
                245
```

<210> SEQ ID NO 67
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (97)..(97)
<223> OTHER INFORMATION: Any amino acid
<220> FEATURE:
<221> NAME/KEY: MOD_RES
<222> LOCATION: (100)..(100)
<223> OTHER INFORMATION: Any amino acid
<220> FEATURE:
<221> NAME/KEY: MOD_RES
<222> LOCATION: (167)..(167)
<223> OTHER INFORMATION: Any amino acid
<220> FEATURE:
<221> NAME/KEY: MOD_RES
<222> LOCATION: (229)..(230)
<223> OTHER INFORMATION: Any amino acid

<400> SEQUENCE: 67

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Xaa Met Ser Xaa Gln Pro Glu Leu Tyr Phe Gly Pro Gly Thr Arg Leu
            100                 105                 110

Thr Val Thr Glu Asp Leu Ile Asn Gly Ser Ala Asp Ala Lys Lys
        115                 120                 125

Asp Ala Ala Lys Lys Asp Gly Lys Ser Lys Glu Val Glu Gln Asn Ser
130                 135                 140

Gly Pro Leu Ser Val Pro Glu Gly Ala Ile Ala Ser Leu Asn Cys Thr
145                 150                 155                 160

Tyr Ser Asp Arg Gly Ser Xaa Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Xaa Xaa Ser Trp Gly Lys Leu Gln Phe Gly Ala Gly
225                 230                 235                 240

Thr Gln Val Val Val Thr Pro Asp Ile
```

<210> SEQ ID NO 68
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Asp Arg Gly Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Thr Asp Ser Trp Gly Lys Leu Gln Phe Gly Ala Gly
225                 230                 235                 240

Thr Gln Val Val Val Thr Pro Asp Ile
                245
```

<210> SEQ ID NO 69
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
```

```
              35                  40                  45
Ser Val Gly Val Gly Ile Thr Asp Gln Gly Asp Val Pro Asp Gly Tyr
 50                  55                  60

Lys Val Ser Arg Ser Thr Thr Glu Asp Phe Pro Leu Arg Leu Leu Ser
 65                  70                  75                  80

Ala Ala Pro Ser Gln Thr Ser Val Tyr Phe Cys Ala Ser Arg Pro Gly
                 85                  90                  95

Trp Met Ser Gly Gln Pro Glu Leu Tyr Phe Gly Pro Gly Thr Arg Leu
                100                 105                 110

Thr Val Thr Glu Asp Leu Ile Asn Gly Ser Ala Asp Ala Lys Lys
                115                 120                 125

Asp Ala Ala Lys Lys Asp Gly Lys Ser Lys Glu Val Glu Gln Asn Ser
130                 135                 140

Gly Pro Leu Ser Val Pro Glu Gly Ala Ile Ala Ser Leu Asn Cys Thr
145                 150                 155                 160

Tyr Ser Asp Arg Gly Ser Thr Ser Phe Phe Trp Tyr Arg Gln Tyr Ser
                165                 170                 175

Gly Lys Ser Pro Glu Leu Ile Met Ser Ile Tyr Ser Asn Gly Asp Lys
                180                 185                 190

Glu Asp Gly Arg Phe Thr Ala Gln Leu Asn Lys Ala Ser Gln Tyr Val
                195                 200                 205

Ser Leu Leu Ile Arg Asp Ser Gln Pro Ser Asp Ser Ala Thr Tyr Leu
210                 215                 220

Cys Ala Val Thr Lys Tyr Ser Trp Gly Lys Leu Gln Phe Gly Ala Gly
225                 230                 235                 240

Thr Gln Val Val Val Thr Pro Asp Ile
                245

<210> SEQ ID NO 70
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Lys Glu Val Glu Gln Asn Ser Gly Pro Leu Ser Val Pro Glu Gly Ala
 1               5                  10                  15

Ile Ala Ser Leu Asn Cys Thr Tyr Ser Asp Arg Gly Ser Gln Ser Phe
                 20                  25                  30

Phe Trp Tyr Arg Gln Tyr Ser Gly Lys Ser Pro Glu Leu Ile Met Ser
                 35                  40                  45

Ile Tyr Ser Asn Gly Asp Lys Glu Asp Gly Arg Phe Thr Ala Gln Leu
 50                  55                  60

Asn Lys Ala Ser Gln Tyr Val Ser Leu Leu Ile Arg Asp Ser Gln Pro
 65                  70                  75                  80

Ser Asp Ser Ala Thr Tyr Leu Cys Ala Val Thr Thr Asp Ser Trp Gly
                 85                  90                  95

Lys Leu Gln Phe Gly Ala Gly Thr Gln Val Val Val Thr Pro Asp Ile
                100                 105                 110

<210> SEQ ID NO 71
<211> LENGTH: 249
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 71

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Cys Arg Met Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Thr Asp Tyr Ser Gly Lys Leu Gln Phe Gly Ala Gly
225                 230                 235                 240

Thr Gln Val Val Val Thr Pro Asp Ile
                245

<210> SEQ ID NO 72
<211> LENGTH: 249
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

```
Ala Ala Pro Ser Gln Thr Ser Val Tyr Phe Cys Ala Ser Arg Pro Gly
                85                  90                  95

Asp Ala Gly Gly Arg Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Pro Arg Arg Ser Thr Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Thr Asp Thr Asn Gly Lys Leu Gln Phe Gly Ala Gly
225                 230                 235                 240

Thr Gln Val Val Val Thr Pro Asp Ile
                245

<210> SEQ ID NO 73
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Cys Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Cys Arg Phe Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190
```

Glu Asp Gly Arg Phe Thr Ala Gln Leu Asn Lys Ala Ser Gln Tyr Val
            195                 200                 205

Ser Leu Leu Ile Arg Asp Ser Gln Pro Ser Asp Ser Ala Thr Tyr Leu
210                 215                 220

Cys Ala Val Thr Thr Asp Glu Val Gly Lys Leu Gln Phe Gly Ala Gly
225                 230                 235                 240

Thr Gln Val Val Val Thr Pro Asp Ile
            245

<210> SEQ ID NO 74
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
                85                  90                  95

Leu Met Ser Ala Gln Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
        115                 120                 125

Asp Ala Ala Lys Lys Asp Gly Lys Ser Lys Glu Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Thr Arg Tyr Ser Thr Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
        195                 200                 205

Ser Leu Leu Ile Arg Asp Ser Gln Pro Ser Asp Ser Ala Thr Tyr Leu
    210                 215                 220

Cys Ala Val Thr Thr Asp Pro Leu Gly Lys Leu Gln Phe Gly Ala Gly
225                 230                 235                 240

Thr Gln Val Val Val Thr Pro Asp Ile
            245

<210> SEQ ID NO 75
<211> LENGTH: 249
<212> TYPE: PRT
<213> ORGANISM: Artificial Sequence
<220> FEATURE:
<223> OTHER INFORMATION: Description of Artificial Sequence: Synthetic

```
              polypeptide

<400> SEQUENCE: 75

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ala Trp Tyr Arg Gln Asp Pro Gly Met Gly Leu Arg Leu Ile His Tyr
        35                  40                  45

Ser Val Gly Val Gly Ile Thr Asp Gln Gly Asp Val Pro Asp Gly Tyr
    50                  55                  60

Lys Val Ser Arg Ser Thr Thr Glu Asp Phe Pro Leu Arg Leu Leu Ser
65                  70                  75                  80

Ala Ala Pro Ser Gln Thr Ser Val Tyr Phe Cys Ala Ser Arg Pro Gly
            85                  90                  95

Arg Ala Gly Gly Arg Pro Glu Leu Tyr Phe Gly Pro Gly Thr Arg Leu
            100                 105                 110

Thr Val Thr Glu Asp Leu Ile Asn Gly Ser Ala Asp Asp Ala Lys Lys
            115                 120                 125

Asp Ala Ala Lys Lys Asp Gly Lys Ser Lys Val Glu Gln Asn Ser
    130                 135                 140

Gly Pro Leu Ser Val Pro Glu Gly Ala Ile Ala Ser Leu Asn Cys Thr
145                 150                 155                 160

Tyr Ser Asn Arg Ser Ser Gln Ser Phe Phe Trp Tyr Arg Gln Tyr Ser
                165                 170                 175

Gly Lys Ser Pro Glu Leu Ile Met Ser Ile Tyr Ser Asn Gly Asp Lys
            180                 185                 190

Glu Asp Gly Arg Phe Thr Ala Gln Leu Asn Lys Ala Ser Gln Tyr Val
            195                 200                 205

Ser Leu Leu Ile Arg Asp Ser Gln Pro Ser Asp Ser Ala Thr Tyr Leu
    210                 215                 220

Cys Ala Val Thr Thr Asp Asn His Gly Lys Leu Gln Phe Gly Ala Gly
225                 230                 235                 240

Thr Gln Val Val Val Thr Pro Asp Ile
                245
```

ENGINEERING T CELL RECEPTORS

RELATED APPLICATIONS

The present application is a divisional of U.S. patent application Ser. No. 14/417,434, filed on Jan. 26, 2015, which in turn is a U.S. national stage filing under 35 U.S.C. § 371(c), of International Application No. PCT/US2013/052283, filed on Jul. 26, 2013, which in turn claims priority to U.S. Provisional Application No. 62/676,373, filed Jul. 27, 2012. The entire contents of the foregoing applications are incorporated herein by reference.

CROSS-REFERENCE TO RELATED APPLICATIONS

This application claims the benefit under 35 U.S.C. § 119(e) of U.S. Provisional Patent Application No. 61/676,373 filed Jul. 27, 2012, and this provisional application is incorporated herein by reference in its entirety.

STATEMENT REGARDING FEDERALLY SPONSORED RESEARCH OR DEVELOPMENT

This invention was made with government support under R01 GM055767 and T32 GM070421 awarded by the National Institutes of Health. The government has certain rights in the invention.

FIELD OF THE INVENTION

The disclosure relates to T cell receptor (TCR) scaffolds and TCR libraries, as well as methods of producing modified TCRs and single chain TCRs and the corresponding use of the TCRs for therapeutic, diagnostic, and imaging methods.

STATEMENT REGARDING SEQUENCE LISTING

The Sequence Listing associated with this application is provided in text format in lieu of a paper copy, and is hereby incorporated by reference into the specification. The name of the text file containing the Sequence Listing is A103017_1230US_D1_SL.txt. The text file is 97,497 bytes, was created on Apr. 13, 2018, and is being submitted electronically via EFS-Web.

BACKGROUND

T cell receptors (TCRs) and antibodies are molecules that have evolved to recognize different classes of antigens (ligands) ((Murphy (2012), xix, 868 p.)). TCRs are antigen-specific molecules that are responsible for recognizing antigenic peptides presented in the context of a product of the major histocompatibility complex (MHC) on the surface of antigen presenting cells (APCs) or any nucleated cell (e.g., all human cells in the body, except red blood cells). In contrast, antibodies typically recognize soluble or cell-surface antigens, and do not require presentation of the antigen by an MHC. This system endows T cells, via their TCRs, with the potential ability to recognize the entire array of intracellular antigens expressed by a cell (including virus proteins) that are processed intracellularly into short peptides, bound to an intracellular MHC molecule, and delivered to the surface as a peptide-MHC complex (pepMHC). This system allows virtually any foreign protein (e.g., mutated cancer antigen or virus protein) or aberrantly expressed protein to serve a target for T cells (reviewed in (Davis and Bjorkman (1988) Nature, 334, 395-402; Davis et al. (1998) Annu Rev Immunol, 16, 523-544; Murphy (2012), xix, 868 p.)).

The interaction of a TCR and a pepMHC can drive the T cell into various states of activation, depending on the affinity (or dissociation rate) of binding. The TCR recognition process allows a T cell to discriminate between a normal, healthy cell and, e.g., one that has become transformed via a virus or malignancy, by providing a diverse repertoire of TCRs, wherein there is a high probability that one or more TCRs will be present with a binding affinity for the foreign peptide bound to an MHC molecule that is above the threshold for stimulating T cell activity (Manning and Kranz (1999) Immunology Today, 20, 417-422).

To date, wild type TCRs isolated from either human or mouse T cell clones that were identified by in vitro culturing have been shown to have relatively low binding affinities ($K_D$=1–300 µM) (Davis et al. (1998) Annu Rev Immunol, 16, 523-544). Part of the explanation for this seems to be that T cells that develop in the thymus are negatively selected (tolerance induction) on self-pepMHC ligands, such that T cells with too high of an affinity are deleted (Starr et al. (2003) Annu Rev Immunol, 21, 139-76). To compensate for these relatively low affinities, T cells have evolved a co-receptor system in which the cell surface molecules CD4 and CD8 bind to the MHC molecules (class II and class I, respectively) and synergize with the TCR in mediating signaling activity. CD8 is particularly effective in this process, allowing TCRs with very low affinity (e.g., $K_D$=300 µM) to mediate potent antigen-specific activity.

Directed evolution has been used to generate TCRs with higher affinity for a specific pepMHC. The three different display methods that have been used are yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), and T cell display (Chervin et al. (2008) J Immunol Methods, 339, 175-84). In all three approaches, the process involves engineering, or modifying, a TCR that exhibits the normal, low affinity of the wild-type TCR, so that affinity of mutants of the TCR have increased affinity for the cognate pepMHC (the original antigen that the T cells were specific for). Thus, the wild-type TCR was used as a template for producing mutagenized libraries in one or more of the CDRs, and mutants with higher affinity were selected by binding to the cognate peptide-MHC antigen.

A major problem with each of these TCR-engineering approaches is that they require a different TCR isolated from a T cell clone with reactivity towards a specific peptide antigen in order to develop a higher affinity TCR mutant specific for the peptide antigen (cognate antigen), or structurally similar variants thereof. As there are over 300 defined peptide antigens from various cancers, and many antigens from viruses, it would be advantageous if the same TCR could be used as a platform to generate TCRs against structurally very different antigens (called non-cognate antigens), using in vitro engineering. The present invention addresses these needs and more.

SUMMARY OF THE INVENTION

The present invention relates to T cell receptor (TCR) scaffolds useful, for example and by way of example only, for the generation of products having novel binding specificities. More specifically, the present invention relates to a library of T cell receptor proteins displayed on the surface of yeast, phage, or mammalian cells; to TCR proteins that are selected from the library for binding to a non-cognate antigen not recognized by the original TCR; and to the use of the TCR proteins selected in vitro for therapeutic, diagnostic, or imaging applications.

One aspect of the invention relates to a modified T cell receptor, or antigen binding fragment thereof, comprising a Vα and a Vβ derived from a wild type T cell receptor, wherein the Vα, the Vβ, or both, comprise a mutation in one or more complementarity determining regions (CDRs) relative to the wild type T cell receptor, wherein the modified T cell receptor binds to a non-cognate peptide-MHC not bound by the wild type T cell receptor.

In one embodiment, the wild type T cell receptor comprises the Vα amino acid sequence set forth in SEQ ID NO:1 and the Vβ amino acid sequence set forth in SEQ ID NO:2. In a related embodiment, the modified T cell receptor comprises a modified Vα comprising an amino acid sequence having at least 80% identity to the Vα amino acid sequence set forth in SEQ ID NO:1 and a modified Vβ comprising an amino acid sequence having at least 80% identity to the Vβ amino acid sequence set forth in SEQ ID NO:2, wherein the modified T cell receptor does not bind to the cognate peptide-MHC bound by the wild type T cell receptor. In another embodiment, the modified T cell receptor comprises an amino acid substitution at one or more of CDR1α 31, CDR3α 98, CDR3β 99, CDR3α 97, CDR3β 102, CDR3α 99, CDR3β 100, CDR3β 101, CDR1α 32, CDR1β 30, CDR3β 98. In yet another embodiment, the modified T cell receptor comprises the wild type amino acid at position CDR2α 51. In one embodiment, the modified T cell receptor further comprises the wild type amino acid at position CDR1α 31. In a related embodiment, the modified T cell receptor further comprises the wild type amino acid at position CD1α 28 and CD1α52.

In one embodiment, the wild type T cell receptor is a single-chain T cell receptor A6-X15 comprising the amino acid sequence set forth in SEQ ID NO:3. In another embodiment, the non-cognate peptide-MHC comprises Mart1:HLA.A2, SL9 HIV:HLA.A2, WT-1:HLA.A2, or SURV:HLA.A2. In a related embodiment, the modified T cell receptor comprises 1) a modified Vα region comprising an amino acid sequence having at least 90% identity to the Vα region of the amino acid sequence set forth in one of SEQ ID NOs:33, 41, or 42 and 2) a modified Vβ region comprising an amino acid sequence having at least 90% identity to the Vβ region of the amino acid sequence set forth in one of SEQ ID NOs:33, 41, or 42. In certain embodiments, the amino acid sequence set forth in one of SEQ ID NOs:33, 41, or 42.

In another embodiment, the modified T cell receptor is generated by in vitro selection of a yeast display library of mutant T cell receptors. In one embodiment, the wild type T cell receptor is human. In another embodiment, the modified T cell receptor is a single chain T cell receptor. In yet another embodiment, the wild type T cell receptor binds HLA-A2. In one embodiment, a polypeptide encoding the modified T cell receptor is provided. In a related embodiment, a polynucleotide encoding the polypeptide is provided.

Another aspect of the invention provides a modified T cell receptor, or antigen binding fragment thereof, comprising a Vα and a Vβ derived from a wild type T cell receptor, wherein the Vα comprises amino acid residues 140 to 256 of SEQ ID NO:34, and wherein the Vβ comprises amino acid residues 1 to 122 of SEQ ID NO:34.

Another aspect of the invention provides a modified T cell receptor, or antigen binding fragment thereof, comprising a Vα and a Vβ derived from a wild type T cell receptor, wherein the Vα comprises amino acid residues 140 to 255 of SEQ ID NO:43, and wherein the Vβ comprises amino acid residues 1 to 122 of SEQ ID NO:43.

One aspect of the invention provides a method for engineering a T cell receptor, or an antigen binding fragment thereof, with a desired specificity comprising: a) isolating a polynucleotide that encodes a wild type T cell receptor, or an antigen binding fragment thereof; b) generating a library of mutant T cell receptors, or antigen binding fragments thereof, wherein the mutant T cell receptors, or antigen-binding fragment thereof, comprise a mutation in one or more complementarity determining regions relative to the wild type T cell receptor; c) expressing the mutant T cell receptors in a surface display system; and d) selecting mutant T cell receptors that bind to a non-cognate peptide-MHC.

In one embodiment, the wild type T cell receptor comprises the Vα amino acid sequence set forth in SEQ ID NO:1 and the Vβ amino acid sequence set forth in SEQ ID NO:2. In another embodiment, the wild type T cell receptor is a single-chain T cell receptor A6-X15 comprising the amino acid sequence set forth in SEQ ID NO:3. In one embodiment, the surface display system is a yeast display system. In another embodiment, the non-cognate peptide-MHC is Mart1:HLA.A2, SL9 HIV:HLA.A2, WT-1:HLA.A2, or SURV:HLA.A2. In one embodiment, the method further comprises a step of affinity maturation.

BRIEF DESCRIPTION OF THE DRAWINGS

FIG. 1 discloses SEQ ID NO: 7.

FIG. 5 shows the amino acid sequence of the A6 Vβ (SEQ ID NO:2) and Vα (SEQ ID NO:1) regions, and the positions shaded in gray indicate where degenerate libraries were constructed in the stabilized variant A6-X15 (SEQ ID NO:3). The CDRs of each V domain are labeled, and the sequence of the linker that joins the two V regions in the yeast display vector is also shown.

FIG. 7 shows the amino acid sequence alignment of ten clones chosen from a degenerate library of the human A6

X15 scTCR, the RD1 library. FIG. 7 discloses SEQ ID NOs: 4, 22-26, 64-65, and 28-31, respectively, in order of appearance.

FIG. 10A shows the sequence alignments of six clones isolated following the 4th sort with the cognate ligand, Tax (LLFGYPVYV; SEQ ID NO:5):HLA-A2 dimer. FIG. 10A discloses SEQ ID NOs: 2-4, 32, 32, 3, 32, 3, 32, and 1, respectively, in order of appearance.

FIG. 10B shows the DNA sequence alignments of the six RD1 scaffold variants at degenerate positions. Below each codon is the amino acid encoded by that codon with the number of possible codon combinations within an NNS library.

FIG. 11A is a histogram depicting positive staining with the anti-HA antibody for the N-terminal tag, thus indicating surface expression of the AGA2 fusion. Cells were stained with the anti-HA antibody and goat anti-mouse IgG alexa 647 secondary antibody (black line histogram) or secondary only as a control (gray filled histogram). The negative peak for the HA stained cells (black line) is observed in all yeast display experiments and is due to yeast that have lost plasmid, and serves as an internal control for each induced yeast sample.

FIG. 11B is a histogram that shows negative staining with c-myc as this clone lacked the C-terminal c-myc tag. Cells were stained with chicken anti-c-myc antibody and goat anti-chicken IgY alexa 647 secondary antibody or secondary only as a control (gray).

FIG. 11C is a histogram showing staining of the A6-X15 clone with various concentrations of the selecting cognate antigen, Tax:HLA.A2, dimer at the indicated concentrations.

FIG. 11D is a histogram showing staining of the A6-X15 clone with various concentrations of the non-selecting non-cognate antigen, Mart1:HLA.A2.

FIG. 12A shows the sequence alignments of five clones isolated following the 5th sort with a non-cognate ligand, Mart1 (ELAGIGILTV; SEQ ID NO:7):HLA-A2 dimer. FIG. 12A discloses SEQ ID NOs: 2-4, 33, 33, 33, 33, and 33, respectively, in order of appearance.

FIG. 12B shows the DNA sequence alignments of the five RD1 scaffold variants at degenerate positions. Below each codon is the amino acid encoded by that codon with the number of possible codon combinations within an NNS library.

Figure 14:
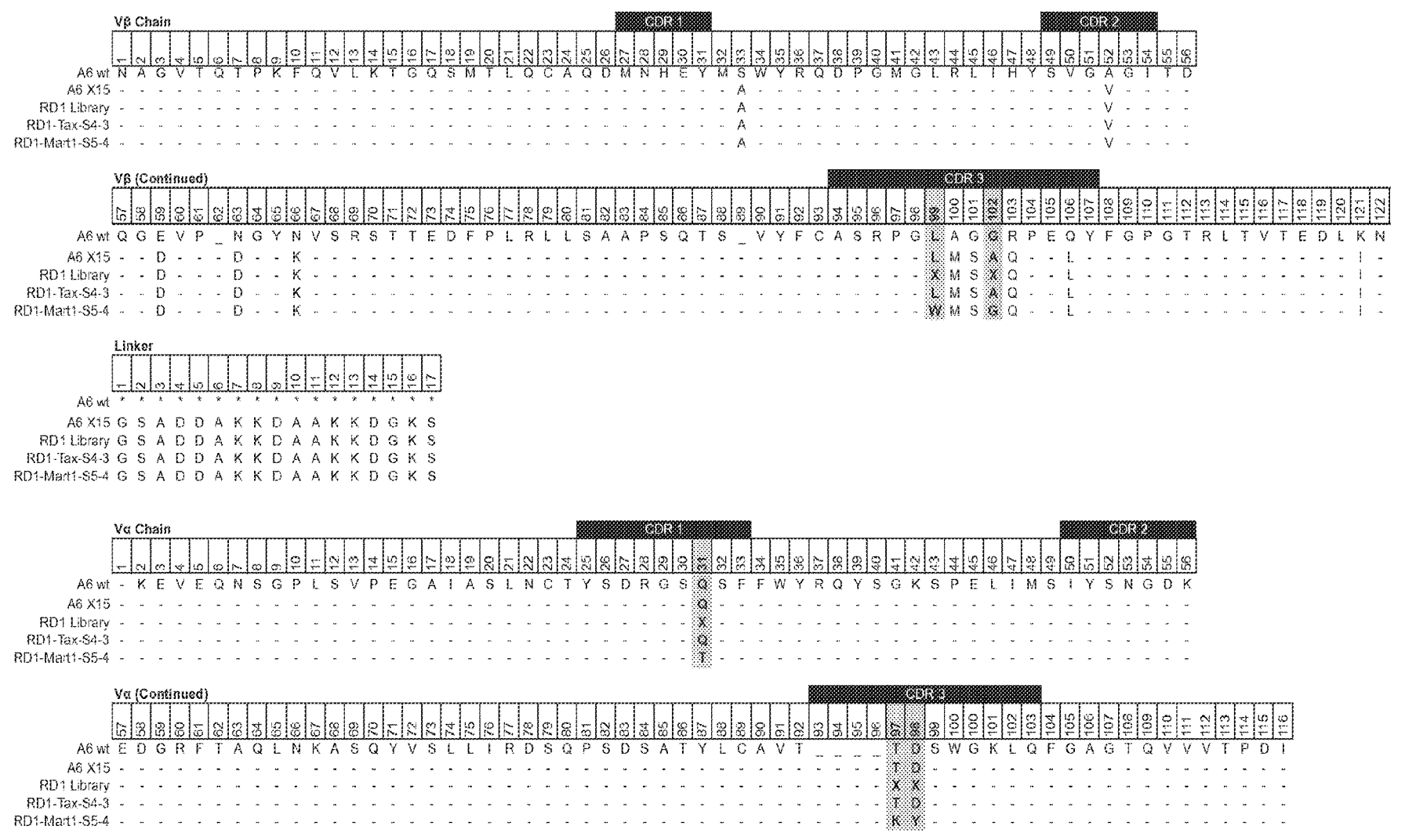

FIG. 14 shows the amino acid sequences of the scaffold A6 single-chain TCR wild type Vα and Vβ regions and two high-affinity variants isolated from the RD1 library, including the five positions of degeneracy in the library. The two clones were isolated from the selection with Tax (clone S4-3; identical to the single-chain stabilized TCR A6-X15; SEQ ID NO:3), and Mart1 (clone S5-4; SEQ ID NO:33). X represents any amino acid. The asterisk is used to indicate where no linker is present in the wild-type A6 structure. FIG. 14 discloses SEQ ID NOs: 2 and 66-70, respectively, in order of appearance.

FIG. 18 shows the amino acid sequences of the scaffold A6 single-chain TCR (wild-type) and high-affinity variants isolated and affinity matured from the RD1 library, including the five positions of degeneracy in the library. Two of the clones were isolated from the selection with Tax (clone RD1-Tax-S4-3; identical to the single-chain stabilized TCR A6-X15) and MART1 (clone RD1-MART1-S5-4). The high affinity clone selected from the RD1-MART1-S5-4 CDR3 affinity maturation libraries is shown (RD1-MART1$^{HIGH}$). X represents any amino acid. The asterisk indicates where no linker is present in the wild-type A6 structure. FIG. 18 discloses SEQ ID NOs: 2-4, 3, 33-34, and 1, respectively, in order of appearance.

FIG. 20 shows the sequence alignment of five clones isolated from the second generation degenerate library (RD2) of the human A6 scTCR that shows diversity prior to selection. FIG. 20 discloses SEQ ID NOs: 35 and 71-75, respectively, in order of appearance.

FIG. 21E shows the sequences of the scaffold A6 single-chain TCR and high-affinity variants isolated from the RD2 library selection with MART1. Sequences of the wild type A6 Vα and Vβ regions of the A6 TCR (Garboczi et al. (1996) Nature, 384, 134-141), the high affinity single-chain variant A6-X15 (Aggen et al. (2011) Protein Engineering, Design, & Selection, 24, 361-72), and two of the clones isolated from the selection with MART1 (clone RD2-MART1-S3-3 and clone RD2-MART1-S3-4) are shown. FIG. 21E discloses SEQ ID NOs: 2-3, 35, 41-42, and 1, respectively, in order of appearance.

FIG. 22 shows the amino acid sequence of an alternative scaffold, human TCR T1-518.45. FIG. 22 discloses SEQ ID NOs: 2-3, 43, and 1, respectively, in order of appearance.

FIG. 24A shows five examples of TCR formats for use as soluble therapeutic products: 1) single-chain TCR in either a Vα-Vβ orientation or Vβ-Vα orientation (mutated high-affinity V domains are shown with an asterisk); 2) single-chain TCR fused in frame with the constant region domains of an antibody; 3) in-frame immunoglobulin fusion to either the constant region of the light chain or the heavy chain; 4) single-chain TCR (or the immunoglobulin fusions shown in 2 and 3) directly coupled to a drug; and 5) single-chain TCR linked in-frame with a single-chain Fv (VL-linker-VH).

FIG. 24B shows the variable domains (V) isolated by yeast display for high-affinity binding using the TCR scaffold inserted into mammalian cell vectors for expression by T cells in adoptive T cell therapy as 1) single-chain receptors in chimeric antigen receptors (CARs) and 2) full length α and β TCRs.

BRIEF DESCRIPTION OF THE SEQUENCES

Figure 1:
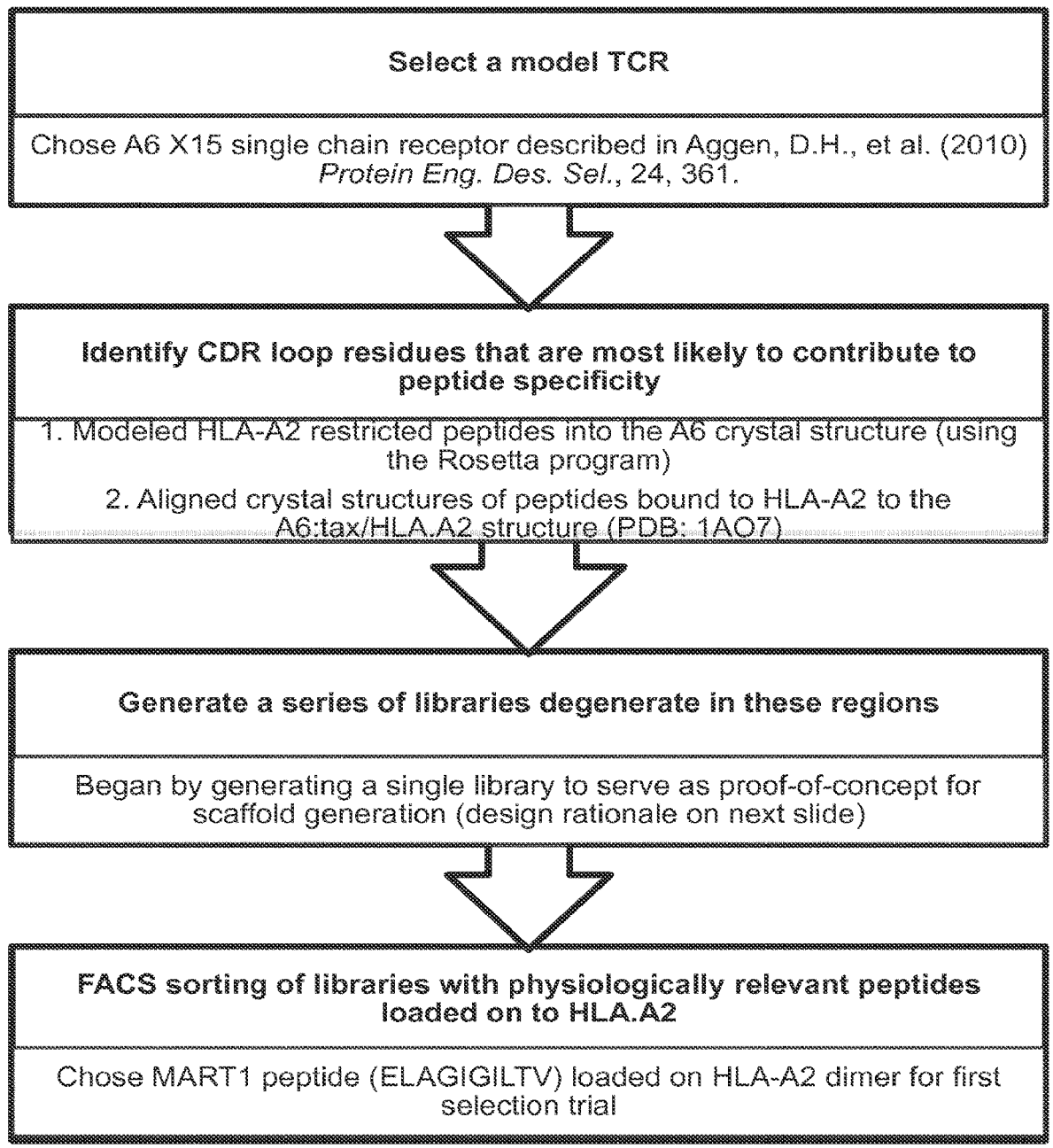
FIG. 1 is a diagram that shows a method for the rational design of a single scaffold for engineering higher affinity TCRs specific for non-cognate antigens.

SEQ ID NO:1 is the amino acid sequence of the Vα region of the A6 TCR.

SEQ ID NO:2 is the amino acid sequence of the Vβ region of the A6 TCR.

SEQ ID NO:3 is the amino acid sequence of the single chain TCR A6-X15 and the identical clones RD1-Tax-S4-3 and RD1-Tax-S4-5.

SEQ ID NO:4 is the amino acid sequence of the RD1 library.

SEQ ID NO:5 is the amino acid sequence of the Tax antigen.

SEQ ID NO:6 is the amino acid sequence of the Mart1-9mer antigen.

SEQ ID NO:7 is the amino acid sequence of the Mart1-10mer antigen.

SEQ ID NO:8 is the amino acid sequence of the SL9 HIV antigen.

SEQ ID NO:9 is the amino acid sequence of the WT-1 antigen.

SEQ ID NO:10 is the amino acid sequence of the Survivin antigen.

SEQ ID NO:11 is the amino acid sequence of the NY-ESO-1 antigen.

SEQ ID NO:12 is the amino acid sequence of the PPI antigen.

SEQ ID NO:13 is the amino acid sequence of the MDM2 antigen.

SEQ ID NO:14 is the amino acid sequence of the HBE183 antigen.

SEQ ID NO:15 is the amino acid sequence of the gp100 antigen.

SEQ ID NO:16 is the amino acid sequence of the MUC1 antigen.

SEQ ID NO:17 is the amino acid sequence of the MAGE A3 antigen.

SEQ ID NO:18 is the amino acid sequence of the HER-2/neu antigen.

SEQ ID NO:19 is the amino acid sequence of the EGFRvIII antigen.

SEQ ID NO:20 is the amino acid sequence of the CEA antigen.

SEQ ID NO:21 is the amino acid sequence of the linker of the RD1 library.

SEQ ID NOs:22-31 are the amino acid sequences of clones #1-10 of the RD1 library.

SEQ ID NO:32 is the amino acid sequence of the clone RD1-Tax-S4-1, and the identical clones RD1-Tax-S4-2, RD1-Tax-S4-4, and RD1-Tax-S4-6.

SEQ ID NO:33 is the amino acid sequence of the clone RD1-Mart1-S5-1, and the identical clones RD1-Mart1-S5-2, RD1-Mart1-S5-3, RD1-Mart1-S5-4, RD1-Mart1-S5-5, and RD1-Mart1-S5-6.

SEQ ID NO:34 is the amino acid sequence of the clone RD1-Mart1$^{HIGH}$.

SEQ ID NO:35 is the amino acid sequence of the RD2 library.

SEQ ID NOs:36-40 are the amino acid sequences of clones #1-5 of the RD2 library.

SEQ ID NO:41 is the amino acid sequence of the clone RD2-Mart1-S3-3.

SEQ ID NO:42 is the amino acid sequence of the clone RD2-Mart1-S3-4.

SEQ ID NO:43 is the amino acid sequence of the clone T1-S18.45.

SEQ ID NO:44 is the amino acid sequence of positions 100-103 in CDR3β of the A6 wild type TCR.

SEQ ID NO:45 is the amino acid sequence of positions 100-103 in CDR3β of A6-X15.

SEQ ID NO:46 is the amino acid sequence of the cognate antigen of the TCR modified by Kessels et al. ((2000) Proc Natl Acad Sci USA, 97, 14578-14583).

SEQ ID NO:47 is the amino acid sequence of the structurally similar peptide of the TCR modified by Kessels et al. ((2000) Proc Natl Acad Sci USA, 97, 14578-14583).

SEQ ID NO:48 is the polynucleotide sequence of the 5' region of the RD1 gene optimized for both yeast and *E. coli*.

SEQ ID NO:49 is the polynucleotide sequence of the 3' region of the RD1 gene optimized for both yeast and *E. coli*.

SEQ ID NO:50 is the polynucleotide sequence of the forward primer used to add pCT302 overhangs.

SEQ ID NO:51 is the polynucleotide sequence of the reverse primer used to add pCT302 overhangs.

SEQ ID NO:52 is the polynucleotide sequence of the forward primer used to generate the CDR3β1 library (Splice 4L).

SEQ ID NO:53 is the polynucleotide sequence of the reverse primer used to generate a CDR3β1 library (Splice 4L).

SEQ ID NO:54 is the polynucleotide sequence of the forward primer used to generate a CDR3β1 library (T7).

SEQ ID NO:55 is the polynucleotide sequence of the reverse primer used to generate a CDR3β1 library (T7).

SEQ ID NO:56 is the polynucleotide sequence of the forward primer used to generate a CDR3β2 library.

SEQ ID NO:57 is the polynucleotide sequence of the reverse primer used to generate a CDR3β2 library.

SEQ ID NO:58 is the polynucleotide sequence of the forward primer used to generate a CDR3α library.

SEQ ID NO:59 is the polynucleotide sequence of the reverse primer used to generate a CDR3α library.

SEQ ID NO:60 is the polynucleotide sequence of the N-terminal DNA flanking sequence added to the RD2 library sequence.

SEQ ID NO:61 is the polynucleotide sequence of the C-terminal DNA flanking sequence added to the RD2 library sequence.

DETAILED DESCRIPTION

The following description is intended to facilitate understanding of the disclosure but is not intended to be limiting.

In general, the terms and phrases used herein have their art-recognized meaning, which can be found by reference to standard texts, journal references and contexts known to those skilled in the art. The following definitions are provided to clarify their specific use in the context of the disclosure.

As used herein, "linked" refers to an association between two groups, which can be a covalent or non-covalent association. Groups may be linked using a variable length peptide chain, a non-amino acid chemical group or other means as known in the art. A linker region can be an amino acid sequence that operably links two functional or structural domains of a protein or peptide.

As used herein, the term "chemotherapeutic agent" refers to any substance capable of reducing or preventing the growth, proliferation, or spread of a cancer cell, a population of cancer cells, tumor, or other malignant tissue. The term is intended also to encompass any antitumor or anticancer agent.

As used herein, the term "effective amount" is intended to encompass contexts such as a pharmaceutically effective amount or therapeutically effective amount. For example, in certain embodiments, the effective amount is capable of achieving a beneficial state, beneficial outcome, functional activity in a screening assay, or improvement of a clinical condition.

As used herein, the term "cancer cell" is intended to encompass definitions as broadly understood in the art. In one embodiment, the term refers to an abnormally regulated cell that can contribute to a clinical condition of cancer in a human or animal. In one embodiment, the term can refer to a cultured cell line or a cell within or derived from a human or animal body. A cancer cell can be of a wide variety of differentiated cell, tissue, or organ types as is understood in the art. Particular examples of cancer cells include breast cancer, colon cancer, skin cancer, ovarian cancer, leukemia, lung cancer, liver cancer, testicular cancer, esophageal cancer, and other types of cancer.

As used herein, the term "cognate antigen" refers to the antigen for which the original TCR was shown to bind to and have specificity for. Similarly, the term "non-cognate antigen" refers to an antigen for which the TCR did not bind to nor have specificity for. More specifically, the "cognate" peptide refers to the antigenic peptide that the original TCR bound to, when it was part of a complex with a protein encoded by the major histocompatibilty complex (MHC). The "non-cognate" peptide refers to a peptide that the original TCR did not bind to, when it was part of a complex with a protein encoded by the MHC.

The terms "wild type" and "wt" are used interchangeably herein and are used in reference to a TCR having an amino acid sequence or a polynucleotide encoding the variable regions isolated from a naturally occurring or non-modified TCR, e.g., the original or parent T cell clone, with specificity for the cognate antigen.

In the figures and tables that present amino acid sequences, the wild type is designated "wt". In the sequences presented below the top sequence, a dash indicates the amino acid is the same as that present in the wt or top sequence of the alignment. A letter indicates a substitution has been made in that position from the top sequence.

As used herein, the terms "modified", "variant", "mutant", "mutated" and "derived" T cell receptor refer to TCR sequences of the variable regions as isolated from the original T cell clone having one or more mutations. Examples of modified TCRs include higher affinity TCRs and TCRs having binding specificity for a non-cognate antigen.

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules.

Downstream refers to a relative position in DNA or RNA and is the region toward the 3' end of a strand.

Expression refers to the transcription of a gene into structural RNA (rRNA, tRNA) or messenger RNA (mRNA) and subsequent translation of an mRNA into a protein.

Two nucleic acid sequences are heterologous to one another if the sequences are derived from separate organisms, whether or not such organisms are of different species, as long as the sequences do not naturally occur together in the same arrangement in the same organism.

Homology refers to the extent of identity between two nucleotide or amino acid sequences.

An amino acid sequence that is functionally equivalent to a specifically exemplified TCR sequence is an amino acid sequence that has been modified by single or multiple amino acid substitutions, by addition and/or deletion of amino acids, or where one or more amino acids have been chemically modified, but which nevertheless retains the binding specificity and high affinity binding activity of a cell-bound or a soluble TCR protein of the present disclosure. Functionally equivalent nucleotide sequences are those that encode polypeptides having substantially the same biological activity as a specifically exemplified cell-bound or soluble TCR protein. In the context of the present disclosure, a soluble TCR protein lacks the portions of a native cell-bound TCR and is stable in solution (i.e., it does not generally aggregate in solution when handled as described herein and under standard conditions for protein solutions).

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

Nucleic acid molecule means a single- or double-stranded linear polynucleotide containing either deoxyribonucleotides or ribonucleotides that are linked by 3'-5'-phosphodiester bonds.

Two DNA sequences are operably linked if the nature of the linkage does not interfere with the ability of the sequences to effect their normal functions relative to each other. For instance, a promoter region would be operably linked to a coding sequence if the promoter were capable of effecting transcription of that coding sequence.

A polypeptide is a linear polymer of amino acids that are linked by peptide bonds.

The term "promoter" refers to a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

A recombinant nucleic acid molecule, for instance a recombinant DNA molecule, is a novel nucleic acid sequence formed in vitro through the ligation of two or more nonhomologous DNA molecules (for example a recombinant plasmid containing one or more inserts of foreign DNA cloned into at least one cloning site).

The terms "transformation" and "transfection" refer to the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid. The terms "transformed" and "transfected" are used interchangeably herein.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g., promoter) for the expression of the inserted DNA. Common vectors include plasmid vectors and phage vectors.

High affinity T cell receptor (TCR) is an engineered TCR with stronger binding to a target ligand than the wild type TCR. Some examples of high affinity include an equilibrium binding constant for a target ligand of between about $10^{-6}$ M and $10^{-12}$ M and all individual values and ranges therein. This range encompasses affinities between those reported to be wild type affinities $10^{-4}$ to $10^{-6}$ M, and those which have been isolated by directed evolution (about $10^{-12}$ M).

A cytokine is a protein, peptide or glycoprotein made by cells that affect other cells.

Mammal includes both human and non-human mammals.

It will be appreciated by those of skill in the art that, due to the degeneracy of the genetic code, numerous functionally equivalent nucleotide sequences encode the same amino acid sequence.

T Cell Receptors

The T cell receptor (TCR) is composed of two chains (αβ or γδ) that pair on the surface of the T cell to form a heterodimeric receptor. The αβ TCR is expressed on most T cells in the body and is known to be involved in the recognition of MHC-restricted antigens. The molecular genetics, structure, and biochemistry of αβ TCRs have now been studied thoroughly. Each α and β chain is composed of two domains: Constant domains (C) that anchor the protein in the cell membrane and that associate with invariant subunits of the CD3 signaling apparatus, and Variable domains (V) that confer antigen recognition through six loops, called complementarity determining regions (CDR). Each of the V domains has three CDRs. These CDRs interact with a complex between an antigenic peptide bound to a protein encoded by the major histocompatibility complex (pepMHC) (Davis and Bjorkman (1988) Nature, 334, 395-402; Davis et al. (1998) Annu Rev Immunol, 16, 523-544; Murphy (2012), xix, 868 p.).

Figure 5:
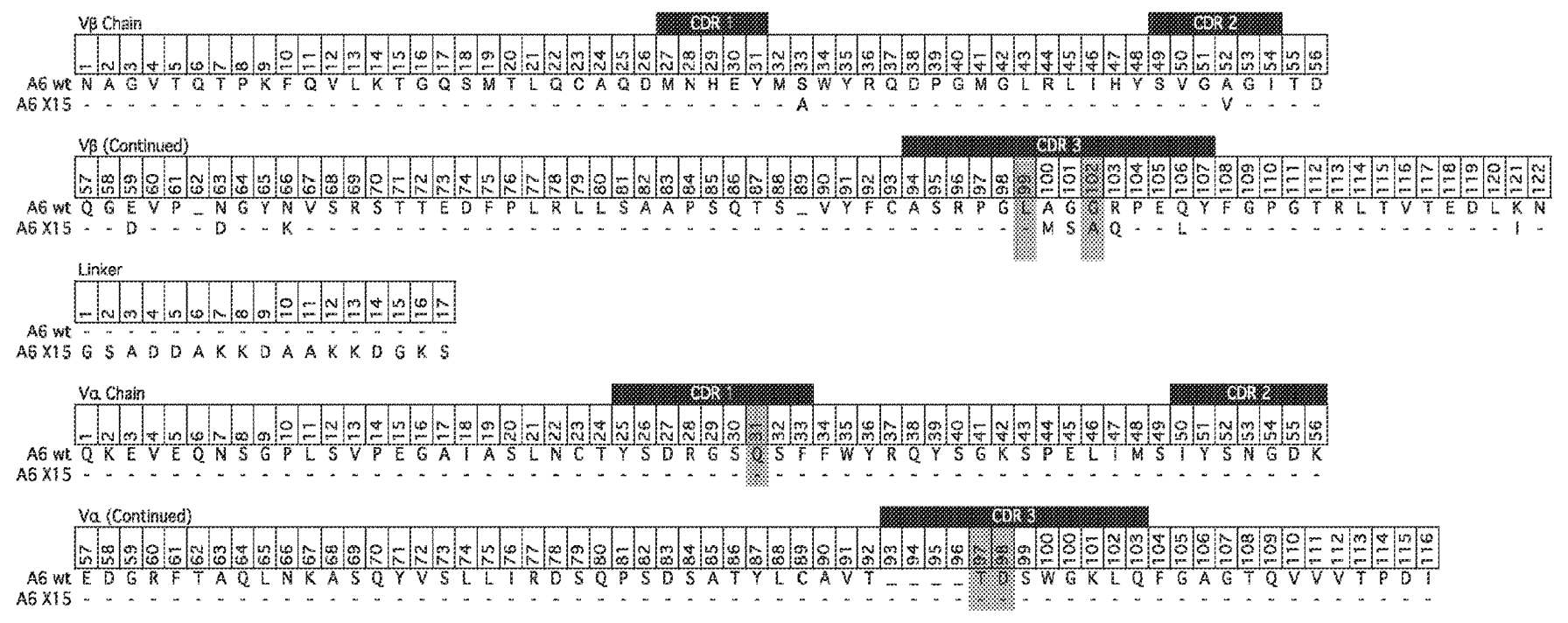

The molecular genetics of the TCR have revealed a process of genetic recombination between multiple genes that combine to form the coding region of the V domains. The process is analogous to antibody development in which the heavy and light chain genes rearrange to generate the tremendous diversity exhibited by B cell-derived antibodies (Tonegawa (1988) In Vitro Cell Dev Biol, 24, 253-65). In the case of T cells, the α chain V domain is formed by the rearrangement of one V region (among about 75 in humans) to one Joining (J) gene segment (among about 61 in humans) (FIG. 5.8, Janeway, $8^{th}$ edition). The β chain V domain is formed by the rearrangement of one V region (among about 52 in humans) to one Diversity (D) gene (among 2 in humans) to one Joining (J) gene segment (among 13 in humans) (FIG. 5.8, (Murphy (2012), xix, 868 p.)). The junctions of the VαJα and JβDβJβ gene rearrangements encode the CDR3 loops of each chain, and they contribute to the tremendous diversity of the αβ TCR, with a theoretical limit of over $10^{15}$ different TCRs (Davis and Bjorkman (1988) Nature, 334, 395-402), well above the achievable diversity in a human because there are only about $10^{11}$ T cells total (Mason (1998) Immunol Today, 19, 395-404). The possible CDR1 and CDR2 diversity of each chain is represented by the number of V genes, as these loops are encoded within the V gene, and TCRs do not undergo somatic mutation in vivo. Although the diversity of CDR1 and CDR2 loops are relatively limited compared to CDR3 loops, there have been a number of examples shown where there has been selection for particular V regions based on the peptide antigen and/or MHC product.

Class I MHC products bind to peptides of 8 to 10 amino acids in length and they are expressed on all nucleated cells in the body (reviewed by (Rock and Goldberg (1999) Annu Rev Immunol, 17, 739-79)). Whereas all the binding energy of an antibody-antigen interaction is focused on the foreign antigen, a substantial fraction of the binding energy of the TCR-peptide:MHC is directed at the self-MHC molecule (Manning and Kranz (1999) Immunology Today, 20, 417-422). In fact, more recent studies have suggested that particular residues of the CDR1 and/or CDR2 loops have evolved to interact with particular residues on the MHC helices, thereby providing a basal affinity for MHC, accounting for the process of MHC-restriction (Garcia et al. (2009) Nat Immunol, 10, 143-7; Marrack et al. (2008) Annu Rev Immunol, 26, 171-203).

There has been interest in using TCRs that have affinities for a peptide-MHC antigen (class I) above the normal range (so called higher affinity TCRs) in order to: 1) drive the activity of CD4 helper T cells (which lack the CD8 co-receptor) or 2) develop soluble TCRs that could be used for direct targeting of a cell, by attaching an "effector" molecule (e.g., antibody Fc regions, a toxic drug, or an antibody scFv such as an anti-CD3 antibody, to form a bispecific protein) ((Ashfield and Jakobsen (2006) IDrugs, 9, 554-9; Foote and Eisen (2000) Proc Natl Acad Sci USA, 97, 10679-81; Holler et al. (2000) Proc Natl Acad Sci USA, 97, 5387-92; Molloy et al. (2005) Curr Opin Pharmacol, 5, 438-43; Richman and Kranz (2007) Biomol Eng, 24, 361-73). This approach also could overcome a problem faced by some cancer patients, whereby their T cells do not express TCRs with adequate specificity and binding affinity to potential tumor antigens (in part due to the thymic and peripheral processes of tolerance). For example, over 300 MHC-restricted, T cell-defined tumor antigens have now been identified (cancer-immunity.org/peptide/) (Boon and Old (1997) Curr Opin Immunol, 9, 681-3; Cheever et al. (2009) Clin Cancer Res, 15, 5323-37). These tumor antigens include mutated peptides, differentiation antigens, and overexpressed antigens, all of which could serve as targets for therapies. Because the majority of the cancer antigens described to date were derived from intracellular proteins that can only be targeted at the cell surface in the context of an MHC molecule, TCRs make the ideal candidate for therapeutics as they have evolved to recognize this class of antigen.

Similarly, TCRs can detect peptides derived from viral proteins that have been naturally processed in infected cells and displayed by an MHC molecule on the cell surface. Many viral antigen targets have been identified over the past 25 years, including peptides derived from viral genomes in HIV and HTLV (e.g., Addo et al. (2007) PLoS ONE, 2, e321; Tsomides et al. (1994) J Exp Med, 180, 1283-93; Utz et al. (1996) J Virol, 70, 843-51). However, patients with these diseases may lack the optimal TCRs for binding and destruction of the infected cells. Finally, it is possible that TCRs could be used as receptor antagonists of autoimmune targets, or as delivery agents to immunosuppress the local immune cell response, in a process that would be highly specific, thereby avoiding general immune suppression ((Molloy et al. (2005) Curr Opin Pharmacol, 5, 438-43; Stone et al. (2012) Protein Engineering)).

Modified T Cell Receptors

Directed evolution has been used to generate TCRs with higher affinity for a specific pepMHC. The three different display methods that have been used are yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), and T cell display (Chervin et al. (2008) J Immunol Methods, 339, 175-84). In all three approaches, the process involves the engineering of a TCR that exhibits the normal, low affinity of the wild-type TCR, so that affinity of mutants of the TCR had increased affinity for the cognate pepMHC (i.e., the original antigen that the T cells were specific for). Thus, the wild-type TCR was used as a template for producing mutagenized libraries in one or more of the CDRs, followed by selection of mutants with higher affinity, by binding to the cognate peptide-MHC antigen.

Yeast display allows for the protein of interest to be expressed on the surface as an Aga2-fusion (Boder and Wittrup (1997) Nat. Biotech., 15, 553-557; Boder and Wittrup (2000) Methods Enzymol, 328, 430-44). This system has been used successfully in the engineering of higher affinity TCRs, single-chain antibodies, fibronectin, and other proteins. In the yeast display system, the TCR has been displayed as a stabilized single-chain protein, in Vβ-linker-Vα or Vα-linker-Vβ forms (Aggen et al. (2011) Protein Engineering, Design, & Selection, 24, 361-72; Holler et al. (2000) Proc Natl Acad Sci USA, 97, 5387-92; Kieke et al. (1999) Proc Natl Acad Sci USA, 96, 5651-6; Richman et al. (2009) Mol Immunol, 46, 902-16; Weber et al. (2005) Proc Natl Acad Sci USA, 102, 19033-8), or as a two-chain heterodimer (Aggen et al. (2011) Protein Engineering, Design, & Selection, 24, 361-72; Richman et al. (2009) Mol Immunol, 46, 902-16). Two mouse TCRs have been engineered for higher affinity using this system: 2C (MHC class-I restricted) and 3.L2 (MHC class-II restricted) (Holler et al. (2000) Proc Natl Acad Sci USA, 97, 5387-92; Weber et al. (2005) Proc Natl Acad Sci USA, 102, 19033-8). Human TCR single-chain Vα Vβ fragments (called scTv or scTCR) have also recently been developed by taking advantage of the exceptional stability of the human Vα region called Vα2 (Aggen et al. (2011) Protein Engineering, Design, & Selection, 24, 361-72). In this case, in vitro engineered, high-affinity T cell receptors in a single-chain format were used to isolate human stabilized scTv fragments (Vβ-linker-Vα), which could be expressed as stable proteins, both on the surface of yeast and in soluble form from E. coli. The TCRs included two stabilized, human scTv fragments, the A6 scTv that is specific for a peptide derived from the human T cell lymphotrophic virus Tax protein (peptide: $Tax_{11-19}$, SEQ ID NO:5), and the 868 scTv that is specific for a peptide derived from the human immunodeficiency virus Gag protein (peptide: $SL9_{77-85}$, SEQ ID NO:8). Both of these TCRs used the Vα2 gene (IMGT: TRAV12 family), but they had CDR3α, CDR1β, CDR2β, and CDR3β residues derived from the original T cell clone from which the TCRs were isolated. Thus, the higher affinity mutants of these scTCRs were each derived from their original (parental) TCR against their cognate peptide-MHC antigens.

In a second system, phage display, the protein of interest is fused to the N-terminus of a viral coat protein (Scott and Smith (1990) Science, 249, 386-90). Various TCRs, including those called A6, 868, and 1G4 (MHC class-I restricted), have been engineered for higher affinity using this method (Li et al. (2005) Nat Biotechnol, 23, 349-54; Sami et al. (2007) Protein Eng Des Sel, 20, 397-403; Varela-Rohena et al. (2008) Nat Med, 14, 1390-5). Phage display of these TCRs was enabled by introduction of a non-native disulfide bond between the two C domains in order to promote pairing of the α and β chains. This system thus uses full-length (VαCα/VβCβ) heterodimeric proteins derived from the original T cell clones for engineering against their cognate peptide-MHC.

A third system that has been reported for the engineering of TCRs is mammalian cell display (Chervin et al. (2008) J Immunol Methods, 339, 175-84; Kessels et al. (2000) Proc Natl Acad Sci USA, 97, 14578-83). This system uses a retroviral vector to introduce the TCR α and β-chains into a TCR-negative T cell hybridoma. In one study (Kessels et al. (2000) Proc Natl Acad Sci USA, 97, 14578-83), the selected mutant TCR was shown to bind to a peptide that was structurally very similar to the cognate peptide (ASNENMDAM, SEQ ID NO:46, versus ASNENMETM, SEQ ID NO:47). In the other study, the affinity of the mutant TCR was shown to be increased for the cognate pepMHC (Chervin et al. (2008) J Immunol Methods, 339, 175-84). It has been shown in many studies that such higher affinity TCRs also exhibit higher affinities against structurally similar variants of the cognate peptide (e.g., (Holler et al. (2003) Nat Immunol, 4, 55-62)). In the mammalian cell display system, introduced TCRs were expressed on the surface in its native conformation, complexed with CD3 subunits, allowing for a fully functional T cell (signaling competent). Full-length, heterodimeric TCRs in their native host were thus engineered using this method.

TCR Scaffold

The present invention provides for the use of a single, e.g., human TCR as a "platform" for engineering higher affinity TCRs against desired antigens (e.g., cognate or non-cognate antigens). In certain embodiments, the TCR scaffold-based TCR engineering methods described herein can include, for example, generating site-directed, mutated libraries of the single TCR, followed by selections for binding to a non-cognate antigen. Engineering is guided by structural analysis of the original, single, or parent TCR. In certain embodiments, the engineered TCRs can be used in soluble form for targeted delivery in vivo, or as recombinantly expressed by T cells in an adoptive transfer method or treatment.

Generally, a TCR scaffold that can be used to engineer TCR mutants against specific antigens is provided. The TCRs are useful for many purposes including, e.g., but not limited to, the treatment of cancer, viral diseases and autoimmune diseases. In a particular embodiment, a single-chain VαVβ TCR (scTCR) scaffold can be prepared and used with a payload such as a cytokine, toxin, radioisotope, chemotherapeutic agent, or drug (similar to antibody-drug conjugates) to deliver the effector molecule to the location where the TCR binds (e.g., tumor). The TCR can also be used in cell therapies, such as adoptive transfer of CD4+ T cells, CD8+ T cells, and/or natural killer (NK) cells, to mediate a response against, e.g., a cancer cell or virus-infected cell. The scTCR scaffolds provided herein can also be used for diagnosis of, e.g., malignant or viral-infected cells through identification of, e.g., neoplastic or viral-associated cell-surface antigens by covalent linkage, for example through amine-reactive or sulfhydryl-reactive amino acid side chains of the TCR, to a detectable group, such as a radioisotope or fluorescent moiety.

In one embodiment, the scTCR scaffold described herein is displayable on the surface of yeast, phage, or mammalian cells and can be used to engineer TCRs with higher affinity to a non-cognate antigen. In one embodiment, the scTCR scaffold described herein can be expressed in a prokaryotic cell, such as *Escherichia coli, Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Bacillus subtilis* or *Bacillus licheniformis*, insect cells (e.g., *Drosophila*), mammalian cells including cell lines such as Chinese hamster ovary cell lines (CHO), or plant species (e.g., canola, soybean, corn, potato, barley, rye, wheat) for example, or other art-known protein expression sources and produced in large quantities. The TCR scaffold can be generated against a particular antigen, and used, for example and by way of example only, to detect a specific peptide/MHC on the surface of a cell. In one embodiment, the scTCR genes disclosed can be linked by use of suitable peptide sequences, encoded within the DNA construct, to the genes for signaling domains and introduced into T cells that can eliminate the targeted cells. These constructs have been termed chimeric antigen receptors (CARs), which are now widely used in the field, including the use of CARs that contain a scTCR.

In another embodiment, the current disclosure provides the amino acid sequences and the form of a single-chain VαVβ T cell receptor (sc VαVβ TCR) scaffold. In the sc VαVβ TCR scaffold provided, the variable alpha and variable beta chains are connected using any suitable peptide linker, including those known in the art such as with antibody single-chain Fv linkages (Bird et al. (1988) Science, 242, 423-426; Holliger et al. (1993) Proc Natl Acad Sci USA, 90, 6444-8; Hoogenboom (2005) Nat Biotechnol, 23, 1105-16; Turner et al. (1997) J Immunol Methods, 205, 43-54). In one embodiment, a soluble human single-chain TCR having the structure: Vα-L-Vβ or Vβ-L-Vα, wherein L is a linker peptide that links Vβ with Vα, Vβ is a TCR variable β region, and Vα is a TCR variable α region is provided. In one embodiment, the model VαVβ TCR is called A6 where Vβ is a TCR variable β region of group 13, and Vα2 is a TCR variable α region of group 2 (Utz, U., et al., 1996). In one embodiment, the model VαVβ TCR is a stabilized single-chain variant of A6 known as A6 X15 (Aggen, D. A., et al., 2011). In one embodiment, the linker peptide contains more than 5 lysine residues. In one embodiment, the linker peptide contains between 5 and 30 amino acids. In one embodiment, the linker peptide has an amino acid sequence of GSADDAKKDAAKKDGKS (SEQ ID NO:21). In one embodiment, the sc VαVβ TCR scaffold provided does not contain a constant region. When the terminology sc VαVβ TCR scaffold is used herein, it is understood that sc VβVα TCR scaffold is also included as the terminology is understood and used in the art. Thus, the Vα and Vβ chains can be connected to each other in any configuration through the linker.

In an aspect of the disclosure, the scVαVβ TCR scaffold of the disclosure binds specifically to a ligand with an equilibrium binding constant $K_D$ of between about $10^{-6}$ M and $10^{-12}$ M. In one embodiment of this aspect of the disclosure, the ligand is a peptide/MHC ligand. In one embodiment, the sc VαVβ TCR of the disclosure has enhanced affinity toward a ligand compared to the affinities of normal, wild type TCRs.

TCRs that bind to a collection of HLA-A, B, and C alleles could be used to treat diseases that encompass a large fraction of the human population. For example, the frequency of many HLA alleles in the population has been determined, and there are many cancer peptide antigens that have been described in association with these alleles (Marsh, Parham, and Barber, The HLA Facts Book, copyright 2000 by Academic Press, ISBN 0-12-545025-7).

By way of example, the average frequency (and range) among Caucasian populations are: HLA-A1, 14%; HLA-A2, 25%; HLA-A3, 12%; HLA-A11, 7%; HLA-A24, 10%; HLA-B7, 9%; HLA-B44, 11%; HLA-Cw4, 12%; HLA-Cw7, 23%. The range found within these populations are: HLA-A1 (5-28%); HLA-A2 (7-40%); HLA-A3 (3-20%); HLA-A11 (2-25%); HLA-A24 (5-18%); HLA-B7 (1-16%); HLA-B44 (5-22%); HLA-Cw4 (6-19%); HLA-Cw7 (13-39%).

The TCR scaffold approach can be extended to other human HLA alleles in various ways. For example, using structure-based design of the TCR scaffolds described here, it is possible to focus mutated libraries in the CDR loops that contact the MHC helices in order to generate leads against other alleles. For example, from the structure of the A6 TCR in complex with HLA-A2, it is known that CDR2alpha libraries would generate variants that bind in the region of the alpha2 helix of HLA-A2. The TCR A 6 residue Y51 resides near HLA-A2 alpha2 helix position(s) E154, Q155, and A158. The HLA-A1 allele differs only at position 158, with a valine rather than an alanine. Thus, the A6 TCR may have a basal affinity for the HLA-A1 allele, which could be improved by generating libraries of CDR2 mutants that encompass position 51, followed by selections for higher affinity binding to the HLA-A1 allele.

Another example makes use of a scaffold that is derived from a TCR specific for a different allele (i.e., peptide bound to the product of that MHC allele). Here, it is possible to generate CDR libraries, as shown for the A6 TCR scaffold, which will react with alternative non-cognate peptide-MHC complexes of that allele. For example, a cancer antigen peptide from MAGE-A3 binds to HLA-A1 and this could be used for selection of the TR libraries.

Biologically Active Groups

Also provided is a sc VαVβ TCR scaffold as described herein which includes a biologically active group. As used herein, "biologically active group" is a group that causes a measurable or detectable effect in a biological system. In one embodiment, the biologically active group is selected from: an anti-tumor agent such as, but not limited to, angiogenesis inhibitors, enzyme inhibitors, microtubule inhibitors, DNA intercalators or cross-linkers, DNA synthesis inhibitors; a cytokine such as, but not limited to IL-2, IL-15, GM-CSF, IL-12, TNF-α, IFN-γ or LT-α (Schrama et al. (2006) Nat Rev Drug Discov, 5, 147-59; Wong et al. (2011) Protein Eng Des Sel, 24, 373-83); an anti-inflammatory group such as, but not limited to, TGF-β, IL-37, IL-10 (Nold et al. (2010) Nat Immunol, 11, 1014-22; Stone et al. (2012) Protein Engineering), a radioisotope such as, but not limited to, $^{90}$Y or $^{131}$I (Reichert and Valge-Archer (2007) Nat Rev Drug Discov, 6, 349-56); a toxin such as, but not limited to, *Pseudomonas* exotoxin A, diphtheria toxin, or the A chain of ricin (Pastan et al. (2006) Nat Rev Cancer, 6, 559-65; Schrama et al. (2006) Nat Rev Drug Discov, 5, 147-59); a drug, or an antibody such as a single-chain Fv.

In one embodiment of this aspect of the disclosure, the biologically active group is a cytotoxic molecule, sometimes referred to as a drug (e.g., in the term "antibody drug conjugate"). As used herein, "cytotoxic" means toxic to cells. Examples of cytotoxic molecules include, but are not limited to, doxorubicin, methotrexate, mitomycin, 5-fluorouracil, duocarmycin, auristatins, maytansines, calicheamicins and analogs of the above molecules (Jarvis (2012) Chemical and Engineering News, 90, 12-18; Litvak-Greenfeld and Benhar (2012) Adv Drug Deliv Rev; Ricart and Tolcher (2007) Nat Clin Pract Oncol, 4, 245-55). Cytotoxic molecules do not need to cause complete cell death, but rather, a measurable or detectable inhibition of growth or decrease in cell activity.

In one embodiment, a TCR described herein is linked to an enzyme capable of converting a prodrug into a drug. This is useful, for example, by allowing the active form of the drug to be created at the location targeted by the TCR (e.g., at the site of a tumor).

In one embodiment, the biologically active group is bound to the single-chain TCR through a linker, which may be accomplished through standard chemical reactions such as with free amine groups or sulfhydryl groups of the TCR.

In another embodiment, the TCR is attached to a single-chain antibody fragment (scFv) to generate a bispecific agent. Bispecific antibodies that contain one scFv against a tumor antigen, and one against the CD3 molecule of the T cell have now been used successfully in the clinic (Bargou et al. (2008) Science, 321, 974-7). In addition, a bispecific agent containing a TCR and a scFv against CD3 has also been reported (Liddy et al. (2012) Nat Med, 18, 980-7).

Also provided is a single-chain VαVβ TCR as described herein which includes a detectable group. In one embodiment, the detectable group is one that can be detected by spectroscopic or enzyme-based methods. In one embodiment, the detectable group is a fluorescent group, such as, but not limited to fluorescein, R-phycoerythrin (PE), PE-Cy5, PE-Cy7, Texas red, or allophycocyanin (APC); a radiolabeled group such as, but not limited to, $^{125}$I, $^{32}$P, $^{99m}$Tc; an absorbing group, or an enzyme with properties that generate detectable products such as, but not limited to, horseradish peroxidase, or alkaline phosphatase.

As known in the art, a biologically active group, detectable group or other group attached to the TCR can be attached using a flexible peptide linker or by chemical conjugation, and can be covalently or noncovalently attached to the TCR.

Antigen Specificity

Also provided herein are sc VαVβ TCR scaffolds that recognize (or target) a specific antigen. In one embodiment, the TCR is specific for recognition of a virus or fragment thereof. In one embodiment, the TCR is specific for recognition of a cancer-specific epitope. In one embodiment, the TCR is specific for recognition of autoimmune associated epitope. Other targets include those listed in The HLA Factsbook (Marsh et al. (2000)) and others known in the art. Specific target antigens include tumor-associated antigens (van der Bruggen P et al. Peptide database: T cell-defined tumor antigens. Cancer Immun 2013. cancerimmunity.org/peptide/; (Cheever et al. (2009) Clin Cancer Res, 15, 5323-37), viral antigens ((Addo et al. (2007) PLoS ONE, 2, e321; Anikeeva et al. (2009) Clin Immunol, 130, 98-109)), and autoimmune associated epitopes ((Bulek et al. (2012) Nat Immunol, 13, 283-9; Harkiolaki et al. (2009) Immunity, 30, 348-57; Skowera et al. (2008) J Clin Invest, 118, 3390-402). 2000; 60: 4845-9), NY-ESO-1 (Barfoed A M et al. Scand J Immunol 2000; 51: 128-33.), PPI (Bulek 2012 Nature Immunology), MDM2 (Asai et al 2002 Cancer Immunity), MDM4, HBE183, gp100 (Bakker A B et al. Int J Cancer 1995; 62: 97-102; Kawakami Y et al. J Immunol 1995; 154: 3961-3968), MUC1 (Brossart P et al. Blood 1999; 93: 4309-17), MAGE A3 (van der Bruggen P et al. Eur J Immunol 1994; 24: 3038-43), HER-2/neu (Fisk B et al. J Exp Med 1995; 181: 2109-2117), EGVFvIII (Sampson Semin Immunol 2008; 20:267-75), CEA (Tsang K Y et al. J Natl Cancer Inst 1995; 87: 982-990), and SL9/HIV gag (Altfeld et al. 2001 J. Virol. 75:1301) listed in Table 1 below. The ranking score in Table 1 is from Cheever et al. (2009) Clin Cancer Res, 15, 5323-37. Also provided is a scVαVβ TCR mutant derived from the A6 scaffold that recognizes the specific non-cognate antigen called MART-1/HLA-A2 (peptide ELAGIGILTV, SEQ ID NO:7, bound to the HLA molecule A2).

TABLE 1

Target Antigens

| Antigen | Type | Peptide Sequence ||||||||| | SEQ ID NO | Ranking |
| | | 0 | 1 | 2 | 3 | 4 | 5 | 6 | 7 | 8 | 9 | | |
| --- | --- | --- | --- | --- | --- | --- | --- | --- | --- | --- | --- | --- | --- |
| MART-1 | Cancer | E | L | A | G | I | G | I | L | T | V | SEQ ID NO: 7 | 14 |
| WT-1 | Cancer | — | R | M | F | P | N | A | P | Y | L | SEQ ID NO: 9 | 1 |
| SURV | Cancer | — | L | T | L | G | E | F | L | K | L | SEQ ID NO: 10 | 21 |
| NY-ESO-1 | Cancer | — | S | L | L | M | W | I | T | Q | C | SEQ ID NO: 11 | 10 |
| PPI | Autoimmune | — | A | L | W | G | P | D | A | A | A | SEQ ID NO: 12 | — |
| MDM2 (also in mdm4) | Cancer | — | V | L | F | Y | L | G | Q | Y | — | SEQ ID NO: 13 | — |
| HBE183 | Viral | — | F | L | L | T | R | I | L | T | I | SEQ ID NO: 14 | — |
| gp100 | Cancer | — | K | T | W | G | Q | Y | W | Q | V | SEQ ID NO: 15 | 16 |
| MUC1 | Cancer | — | S | T | A | P | P | V | H | N | V | SEQ ID NO: 16 | 2 |
| MAGE A3 | Cancer | — | F | L | W | G | P | R | A | L | V | SEQ ID NO: 17 | 8 |
| HER-2/neu | Cancer | — | K | I | F | G | S | L | A | F | L | SEQ ID NO: 18 | 6 |
| EGFRvIII | Cancer | — | L | E | E | K | K | G | N | Y | V | SEQ ID NO: 19 | 5 |
| CEA | Cancer | — | Y | L | S | G | A | N | L | N | L | SEQ ID NO: 20 | 13 |
| SL9/HIVgag | Viral | — | S | L | Y | N | T | V | A | T | L | SEQ ID NO: 8 | — |

In one embodiment, the target antigen is one of MART-1 (Kawakami Y et al. J Exp Med 1994; 180:347-352; Romero et al. 2002. Immunol. Rev. 188, 81-96), WT-1 (Gessler et al. Nature 343 (6260), 774-778 (1990)), SURV (Schmidt S M et al. Blood 2003; 102: 571-6; Schmitz M et al. Cancer Res Also provided herein is a human TCR for use in a method of treating or preventing a disease or disorder in a mammal, comprising administering an effective amount of a modified TCR linked to a therapeutically effective molecule to a mammal. In a particular embodiment, the mammal is human. In another embodiment, the mammal is a companion animal (e.g., a dog, cat, rabbit, rodent, horse) or a livestock animal (e.g., a cow, horse, pig).

As used herein a "disease state" is an abnormal function or condition of an organism. In one embodiment, the disease state is selected from the group consisting of: cancer, viral, bacterial or autoimmune disease. Also provided is an isolated single-chain TCR as described herein, and a method for producing the single-chain TCR in E. coli. Also provided is a pharmaceutical composition comprising a scTCR as described herein and a pharmaceutically acceptable carrier. Also provided is the sc VαVβ TCR described herein which has been linked to signaling domains that yields an active TCR on the surface of a T cell. In one embodiment, this scTCR can be used in a method of treating a disease state in a mammal, comprising: cloning the TCR into a vector, introducing the vector into T cells of a patient, and adoptive transferring of the T cells back into a patient.

Modified TCR Polypeptides and Polynucleotides

The disclosure contemplates a DNA vector that includes at least one DNA segment encoding a single-chain T cell receptor (scTCR).

Those of skill in the art, through standard mutagenesis techniques, in conjunction with the assays described herein, can obtain altered TCR sequences and test them for particular binding affinity and/or specificity. Useful mutagenesis techniques known in the art include, without limitation, de novo gene synthesis, oligonucleotide-directed mutagenesis, region-specific mutagenesis, linker-scanning mutagenesis, and site-directed mutagenesis by PCR (see e.g., Sambrook et al. (1989) and Ausubel et al. (1999)).

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well known that conservative amino acid substitutions, that is, substitution of one amino acid for another amino acid of similar size, charge, polarity and conformation, are unlikely to significantly alter protein function. The 20 standard amino acids that are the constituents of proteins can be broadly categorized into four groups of conservative amino acids as follows: the nonpolar (hydrophobic) group includes alanine, isoleucine, leucine, methionine, phenylalanine, proline, tryptophan and valine; the polar (uncharged, neutral) group includes asparagine, cysteine, glutamine, glycine, serine, threonine and tyrosine; the positively charged (basic) group contains arginine, histidine and lysine; and the negatively charged (acidic) group contains aspartic acid and glutamic acid. Substitution in a protein of one amino acid for another within the same group is unlikely to have an adverse effect on the biological activity of the protein.

In one embodiment, a scTCR of the disclosure may contain additional mutations in any region or regions of the variable domain that results in a stabilized protein. In one embodiment, one or more additional mutations is in one or more of CDR1, CDR2, HV4, CDR3, FR2, and FR3. The regions used for mutagenesis can be determined by directed evolution, where crystal structures or molecular models are used to generate regions of the TCR which interact with the ligand of interest (antigen, for example). In other examples, the variable region can be reshaped, by adding or deleting amino acids to engineer a desired interaction between the scTCR and the ligand.

Polypeptides of the invention include modified TCRs, and antigen-binding fragments thereof (e.g., scTCR), and chimeric antigen receptors (CARs). The terms "polypeptide" "protein" and "peptide" and "glycoprotein" are used interchangeably and mean a polymer of amino acids not limited to any particular length. The term does not exclude modifications such as myristylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the modified TCRs, or antigen-binding fragments thereof, of the present disclosure, or sequences that have deletions from, additions to, and/or substitutions of one or more amino acid of a modified TCR, or antigen binding fragment thereof. Thus, a "polypeptide" or a "protein" can comprise one (termed "a monomer") or a plurality (termed "a multimer") of amino acid chains.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In particular embodiments, a subject modified TCR may have: a) a TCR alpha chain variable region having an amino acid sequence that is at least 80% identical, at least 85% identical, at least 90%, at least 95% or at least 98% or 99% identical, to the alpha chain variable region of a modified TCR described herein; and b) a beta chain variable region having an amino acid sequence that is at least 80% identical, at least 85%, at least 90%, at least 95% or at least 98% or 99% identical, to the light chain variable region of a modified TCR described herein.

In particular embodiments, the modified TCR may comprise: a) a TCR alpha chain variable region comprising: i. a CDR1 region that is identical in amino acid sequence to the alpha chain CDR1 region of a selected TCR described herein; ii. a CDR2 region that is identical in amino acid sequence to the alpha chain CDR2 region of the selected TCR; and iii. a CDR3 region that is identical in amino acid sequence to the alpha chain CDR3 region of the selected TCR; and b) a beta chain variable region comprising: i. a CDR1 region that is identical in amino acid sequence to the beta chain CDR1 region of the selected TCR; ii. a CDR2 region that is identical in amino acid sequence to the beta chain CDR2 region of the selected TCR; and iii. a CDR3 region that is identical in amino acid sequence to the beta chain CDR3 region of the selected TCR; wherein the TCR specifically binds a selected non-cognate antigen. In a further embodiment, the modified TCR, or antigen-binding fragment thereof, is a variant modified TCR wherein the variant comprises an alpha chain and a beta chain identical to the selected modified TCR except for up to 8, 9, 10, 11, 12, 13, 14, 15, or more amino acid substitutions in the CDR regions of the V alpha and V beta regions. In this regard, there may be 1, 2, 3, 4, 5, 6, 7, 8, or in certain embodiments, 9, 10, 11, 12, 13, 14, 15 more amino acid substitutions in the CDR regions of the selected variant modified TCR. Substitutions may be in CDRs either in the V alpha and/or the V beta regions. (See e.g., Muller, 1998, Structure 6:1153-1167).

In one embodiment, a polynucleotide encoding a modified TCR, or an antigen-binding fragment thereof, is provided. In other related embodiments, the polynucleotide may be a variant of a polynucleotide encoding the modified TCR. Polynucleotide variants may have substantial identity to a polynucleotide sequence encoding a modified TCR described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence such as a sequence encoding an antibody described herein, using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

Typically, polynucleotide variants will contain one or more substitutions, additions, deletions and/or insertions, preferably such that the binding affinity of the antibody encoded by the variant polynucleotide is not substantially diminished relative to an antibody encoded by a polynucleotide sequence specifically set forth herein.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J., Unified Approach to Alignment and Phylogenes, pp. 626-645 (1990); Methods in Enzymology vol. 183, Academic Press, Inc., San Diego, Calif.; Higgins, D. G. and Sharp, P. M., CABIOS 5:151-153 (1989); Myers, E. W. and Muller W., CABIOS 4:11-17 (1988); Robinson, E. D., Comb. Theor 11:105 (1971); Santou, N. Nes, M., Mol. Biol. Evol. 4:406-425 (1987); Sneath, P. H. A. and Sokal, R. R., Numerical Taxonomy—the Principles and Practice of Numerical Taxonomy, Freeman Press, San Francisco, Calif. (1973); Wilbur, W. J. and Lipman, D. J., Proc. Natl. Acad., Sci. USA 80:726-730 (1983).

Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., Nucl. Acids Res. 25:3389-3402 (1977), and Altschul et al., J. Mol. Biol. 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, Proc. Natl. Acad. Sci. USA 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode an antibody as described herein. Some of these polynucleotides bear minimal sequence identity to the nucleotide sequence of the native or original polynucleotide sequence that encode modified TCRs that bind to, e.g., the same non-cognate antigen. Nonetheless, polynucleotides that vary due to differences in codon usage are expressly contemplated by the present disclosure. In certain embodiments, sequences that have been codon-optimized for mammalian expression are specifically contemplated.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1-4, Plenum Press, New York. Abbreviations and nomenclature, where employed, are deemed standard in the field and commonly used in professional journals such as those cited herein.

Homology between nucleotide sequences can be determined by DNA hybridization analysis, wherein the stability of the double-stranded DNA hybrid is dependent on the extent of base pairing that occurs. Conditions of high temperature and/or low salt content reduce the stability of the hybrid, and can be varied to prevent annealing of sequences having less than a selected degree of homology. For instance, for sequences with about 55% G-C content, hybridization and wash conditions of 40-50° C., 6×SSC (sodium chloride/sodium citrate buffer) and 0.1% SDS (sodium dodecyl sulfate) indicate about 60-70% homology, hybridization and wash conditions of 50-65° C., 1×SSC and 0.1% SDS indicate about 82-97% homology, and hybridization and wash conditions of 52° C., 0.1×SSC and 0.1% SDS indicate about 99-100% homology. A wide range of computer programs for comparing nucleotide and amino acid sequences (and measuring the degree of homology) are also available, and a list providing sources of both commercially available and free software is found in Ausubel et al. (1999). Readily available sequence comparison and multiple sequence alignment algorithms are, respectively, the Basic Local Alignment Search Tool (BLAST) (Altschul et al., 1997) and ClustalW programs. BLAST is available on the Internet at ncbi.nlm.nih.gov and a version of ClustalW is available at www2.ebi.ac.uk.

Industrial strains of microorganisms (e.g., *Aspergillus niger, Aspergillus ficuum, Aspergillus awamori, Aspergillus oryzae, Trichoderma reesei, Mucor miehei, Kluyveromyces lactis, Pichia pastoris, Saccharomyces cerevisiae, Escherichia coli, Bacillus subtilis* or *Bacillus licheniformis*), insect (*Drosophila*), mammalian (e.g., Chinese hamster ovary cell lines, CHO), or plant species (e.g., canola, soybean, corn, potato, barley, rye, wheat) may be used as host cells for the recombinant production of the TCR proteins. In certain embodiments, the first step in the heterologous expression of a high affinity TCR protein or soluble protein, an expression construct is assembled to include the TCR or soluble TCR coding sequence and control sequences such as promoters, enhancers and terminators. Other sequences such as signal sequences and selectable markers may also be included. To achieve extracellular expression of the TCR, the expression construct may include a secretory signal sequence. In embodiments, the signal sequence is not included on the expression construct if cytoplasmic expression is desired. In embodiments, the promoter and signal sequence are functional in the host cell and provide for expression and secretion of the TCR or soluble TCR protein. Transcriptional terminators may be included to ensure efficient transcription. Ancillary sequences enhancing expression or protein purification may also be included in the expression construct.

Various promoters (transcriptional initiation regulatory region) may be used according to the disclosure. The selection of the appropriate promoter may be dependent upon the proposed expression host. Promoters from heterologous sources may be used as long as they are functional in the chosen host.

Promoter selection is also dependent upon the desired efficiency and level of peptide or protein production. Inducible promoters such as tac are often employed in order to dramatically increase the level of protein expression in *E. coli*. Overexpression of proteins may be harmful to the host cells. Consequently, host cell growth may be limited. The use of inducible promoter systems allows the host cells to be cultivated to acceptable densities prior to induction of gene expression, thereby facilitating higher product yields.

Various signal sequences may be used according to the disclosure. A signal sequence which is homologous to the TCR coding sequence may be used. Alternatively, a signal sequence which has been selected or designed for efficient secretion and processing in the expression host may also be used. For example, suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge consisting of usually fewer than ten codons, where the bridge ensures correct reading frame of the downstream TCR sequence.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

A selective marker is often employed, which may be part of the expression construct or separate from it (e.g., carried by the expression vector), so that the marker may integrate at a site different from the gene of interest. Examples include markers that confer resistance to antibiotics (e.g., bla confers resistance to ampicillin for *E. coli* host cells, nptII confers kanamycin resistance to a wide variety of prokaryotic and eukaryotic cells) or that permit the host to grow on minimal medium (e.g., HIS4 enables *P. pastoris* or His⁻ *S. cerevisiae* to grow in the absence of histidine). The selectable marker has its own transcriptional and translational initiation and termination regulatory regions to allow for independent expression of the marker. If antibiotic resistance is employed as a marker, the concentration of the antibiotic for selection will vary depending upon the antibiotic, generally ranging from 10 to 600 μg of the antibiotic/mL of medium.

The expression construct is assembled by employing known recombinant DNA techniques (Sambrook et al., 1989; Ausubel et al., 1999). Restriction enzyme digestion and ligation are the basic steps employed to join two fragments of DNA. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (λZAP and pBLUESCRIPT SK-1, Stratagene, LaJolla, Calif.; pET, Novagen Inc., Madison, Wis.—cited in Ausubel et al., 1999) and the particular choice is not critical to the disclosure. The selection of cloning vector will be influenced by the gene transfer system selected for introduction of the expression construct into the host cell. At the end of each stage, the resulting construct may be analyzed by restriction, DNA sequence, hybridization and PCR analyses.

The expression construct may be transformed into the host as the cloning vector construct, either linear or circular, or may be removed from the cloning vector and used as is or introduced onto a delivery vector. The delivery vector facilitates the introduction and maintenance of the expression construct in the selected host cell type. The expression construct is introduced into the host cells by any of a number of known gene transfer systems (e.g., natural competence, chemically mediated transformation, protoplast transformation, electroporation, biolistic transformation, transfection, or conjugation) (Ausubel et al., 1999; Sambrook et al., 1989). The gene transfer system selected depends upon the host cells and vector systems used.

For instance, the expression construct can be introduced into *S. cerevisiae* cells by protoplast transformation or electroporation. Electroporation of *S. cerevisiae* is readily accomplished, and yields transformation efficiencies comparable to spheroplast transformation.

Monoclonal or polyclonal antibodies, preferably monoclonal, specifically reacting with a TCR protein at a site other than the ligand binding site may be made by methods known in the art, and many are commercially available. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1999) *Current Protocols in Molecular Biology*, John Wiley & Sons, Inc., New York.

TCRs in cell-bound or soluble form which are specific for a particular target ligand are useful, for example, as diagnostic probes for screening biological samples (such as cells, tissue samples, biopsy material, bodily fluids and the like) or for detecting the presence of the target ligand in a test sample. Frequently, the TCRs are labeled by joining, either covalently or noncovalently, a substance which provides a detectable signal. Suitable labels include but are not limited to radionuclides, enzymes, substrates, cofactors, inhibitors, fluorescent agents, chemiluminescent agents, magnetic particles and the like. Additionally the TCR can be coupled to a ligand for a second binding molecules: for example, the TCR can be biotinylated. Detection of the TCR bound to a target cell or molecule can then be effected by binding of a detectable streptavidin (a streptavidin to which a fluorescent, radioactive, chemiluminescent, or other detectable molecule is attached or to which an enzyme for which there is a chromophoric substrate available). United States patents describing the use of such labels and/or toxic compounds to be covalently bound to the scTCR include but are not limited to U.S. Pat. Nos. 3,817,837; 3,850,752; 3,927,193; 3,939,350; 3,996,345; 4,277,437; 4,275,149; 4,331,647; 4,348,376; 4,361,544; 4,468,457; 4,444,744; 4,640,561; 4,366,241; RE 35,500; 5,299,253; 5,101,827; 5,059,413.

Labeled TCRs can be detected using a monitoring device or method appropriate to the label used. Fluorescence microscopy or fluorescence activated cell sorting can be used where the label is a fluorescent moiety, and where the label is a radionuclide, gamma counting, autoradiography or liquid scintillation counting, for example, can be used with the proviso that the method is appropriate to the sample being analyzed and the radionuclide used. In addition, there can be secondary detection molecules or particle employed where there is a detectable molecule or particle which recognized the portion of the TCR which is not part of the binding site for the target ligand in the absence of a MHC component as noted herein. The art knows useful compounds for diagnostic imaging in situ; see, e.g., U.S. Pat. Nos. 5,101,827; 5,059,413. Radionuclides useful for therapy and/or imaging in vivo include $^{111}$Indium, $^{97}$Rubidium, $^{125}$Iodine, $^{131}$Iodine, $^{123}$Iodine, $^{67}$Gallium, $^{99}$Technetium. Toxins include diphtheria toxin, ricin and castor bean toxin, among others, with the proviso that once the TCR-toxin complex is bound to the cell, the toxic moiety is internalized so that it can exert its cytotoxic effect. Immunotoxin technology is well known to the art, and suitable toxic molecules include, without limitation, chemotherapeutic drugs such as vindesine, antifolates, e.g., methotrexate, cisplatin, mitomycin, .anthrocyclines such as daunomycin, daunorubicin or adriamycin, and cytotoxic proteins such as ribosome inactivating proteins (e.g., diphtheria toxin, pokeweed antiviral protein, abrin, ricin, *pseudomonas* exotoxin A or their recombinant derivatives. See, generally, e.g., Olsnes and Pihl (1982) *Pharmac. Ther.* 25:355-381 and *Monoclonal Antibodies for Cancer Detection and Therapy*, Eds. Baldwin and Byers, pp. 159-179, Academic Press, 1985.

The general structure of TCR molecules and methods of making and using, including binding to a peptide:Major Histocompatibility Complex have been disclosed. See, for example PCT/US98/04274; PCT/US98/20263; WO99/60120.

Pharmaceutical Compositions and Therapeutic Agents scTCRs specific for a particular target ligand are useful in treating animals and mammals, including humans believed to be suffering from a disease associated with the particular antigen.

Therapeutic products can be made using the materials shown herein. Effective amounts of therapeutic products are the minimum dose that produces a measurable effect in a subject. Therapeutic products are easily prepared by one of ordinary skill in the art. In one embodiment, a scTCR of the disclosure is administered directly to a patient. In one embodiment, a scTCR of the disclosure is linked to PEG or to immunoglobulin constant regions, as known in the art. This embodiment lengthens the serum clearance. In one embodiment, the scTCR is linked to a chemotherapeutic agent or drug in order to deliver the drug to a target cell such as a cancer cell. In one embodiment, the scTCR is linked to a biologic effector molecule such as a cytokine (Tayal and Kalra (2008) Eur J Pharmacol, 579, 1-12). In one embodiment, the scTCR is linked to a cytokine with anti-tumor activity, such as IL-2, IL-12, or TNFα (Wong et al. (2011) Protein Eng Des Sel, 24, 373-83). In one embodiment, the scTCR is linked to an immune-inhibitory cytokine, such as IL-10 or IL-13 (Stone et al. (2012) Protein Engineering). In one embodiment, the scTCR is linked to another antigen binding molecule to form a bispecific agent (Miller et al. (2010) Protein Eng Des Sel, 23, 549-57; Thakur and Lum (2010) Curr Opin Mol Ther, 12, 340-9). In one embodiment, the bispecific molecule is comprised of a scTCR linked to a single chain Fv, such as an anti-CD3 ((Bargou et al. (2008) Science, 321, 974-7; Liddy et al. (2012) Nat Med, 18, 980-7), to crosslink T cells and diseased cells. In one embodiment, the scTCR is linked to TCR signaling domains, such as CD3, to form a chimeric antigen receptor ((Porter et al. (2011) N Engl J Med, 365, 725-33; Sadelain et al. (2009) Curr Opin Immunol, 21, 215-23; Stroncek et al. (2012) J Transl Med, 10, 48). These methods and other methods of administering, such as intravenously, are known in the art. Useful dosages can be determined by one of ordinary skill in the art.

The scTCR compositions can be formulated by any of the means known in the art. They can be typically prepared as injectables, especially for intravenous, intraperitoneal or synovial administration (with the route determined by the particular disease) or as formulations for intranasal or oral administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

The active ingredients are often mixed with optional pharmaceutical additives such as excipients or carriers which are pharmaceutically acceptable and compatible with the active ingredient. Suitable excipients include but are not limited to water, saline, dextrose, glycerol, ethanol, or the like and combinations thereof. The concentration of the scTCR in injectable, aerosol or nasal formulations is usually in the range of 0.05 to 5 mg/ml. The selection of the particular effective dosages is known and performed without undue experimentation by one of ordinary skill in the art. Similar dosages can be administered to other mucosal surfaces.

In addition, if desired, vaccines that could include a scTCR may contain minor amounts of pharmaceutical additives such as auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween® 80 emulsion. Such additional formulations and modes of administration as are known in the art may also be used.

The scTCRs of the present disclosure and/or binding fragments having primary structure similar (more than 90% identity) to the TCR variable regions and which maintain the high affinity for the target ligand may be formulated into vaccines as neutral or salt forms. Pharmaceutically acceptable salts include but are not limited to the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

scTCRs for therapeutic use are administered in a manner compatible with the dosage formulation, and in such amount and manner as are prophylactically and/or therapeutically effective, according to what is known to the art. The quantity to be administered, which is generally in the range of about 100 to 20,000 µg of protein per dose, more generally in the range of about 1000 to 10,000 µg of protein per dose. Similar compositions can be administered in similar ways using labeled scTCRs for use in imaging, for example, to detect cells to which a target ligand is bound. Precise amounts of the active ingredient required to be administered may depend on the judgment of the physician or veterinarian and may be peculiar to each individual, but such a determination is within the skill of such a practitioner.

The vaccine or other immunogenic composition may be given in a single dose; two dose schedule, for example two to eight weeks apart; or a multiple dose schedule. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months. Humans (or other animals) immunized with the retrovirus-like particles of the present disclosure are protected from infection by the cognate retrovirus.

Autoimmune diseases are those diseases in which the immune system produces an immune response against an antigen that is normally present in the host. Autoimmune diseases include rheumatoid arthritis, adjuvant arthritis, myasthenia gravis, encephalomyelitis, multiple sclerosis, thyroiditis, inflammatory bowel disease or systemic lupus erythematosus, type I diabetes, non-obese diabetes, Grave's disease, Hashimoto's disease, osteoarthritis, dermatitis, hepatitis, pemphigus vulgaris, celiac disease, Sjogren's syndrome, Addison's disease, primary myxedema, Goodpasture's syndrome, tuberculoid leprosy, ankylosing spondylitis, Reiter's disease, uveitis, amyloidosis, psoriasis vulgaris, idiopathic hemochromatosis and psorasis.

Every formulation or combination of components described or exemplified can be used to practice the disclosure, unless otherwise stated. Specific names of substances are intended to be exemplary, as it is known that one of ordinary skill in the art can name the same substances differently. When a compound is described herein such that a particular isomer or enantiomer of the compound is not specified, for example, in a formula or in a chemical name, that description is intended to include each isomers and enantiomer of the compound described individual or in any combination. One of ordinary skill in the art will appreciate that methods, target ligands, biologically active groups, starting materials, and synthetic methods other than those specifically exemplified can be employed in the practice of the disclosure without resort to undue experimentation. All art-known functional equivalents, of any such methods, target ligands, biologically active groups, starting materials, and synthetic methods are intended to be included in this disclosure. Whenever a range is given in the specification, for example, a temperature range, a time range, or a composition range, all intermediate ranges and subranges, as well as all individual values included in the ranges given are intended to be included in the disclosure.

The exact formulation, route of administration and dosage can be chosen by the individual physician in view of the patient's condition (see e.g., Fingl et. al., in The Pharmacological Basis of Therapeutics, 1975, Ch. 1 p. 1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above also may be used in veterinary medicine.

Depending on the specific conditions being treated and the targeting method selected, such agents may be formulated and administered systemically or locally. Techniques for formulation and administration may be found in Alfonso and Gennaro (1995). Suitable routes may include, for example, oral, rectal, transdermal, vaginal, transmucosal, or intestinal administration; parenteral delivery, including intramuscular, subcutaneous, or intramedullary injections, as well as intrathecal, intravenous, or intraperitoneal injections.

For injection, the agents of the disclosure may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Use of pharmaceutically acceptable carriers to formulate the compounds herein disclosed for the practice of the disclosure into dosages suitable for systemic administration is within the scope of the disclosure. With proper choice of carrier and suitable manufacturing practice, the compositions of the present disclosure, in particular those formulated as solutions, may be administered parenterally, such as by intravenous injection. Appropriate compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, and then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present disclosure include compositions wherein the active ingredients are contained in an effective amount to achieve the intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions, including those formulated for delayed release or only to be released when the pharmaceutical reaches the small or large intestine.

The pharmaceutical compositions of the present disclosure may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

The following examples further describe non-limiting examples of the disclosure.

Example 1

Selection of a Model TCR

TCRs all adopt a similar Ig-fold and docking angle, and TCR recognition of pepMHC is mediated entirely by specific residues on CDR loops (Garcia et al. (2009) Nat Immunol, 10, 143-7; Marrack et al. (2008) Annu Rev Immunol, 26, 171-203; Rudolph et al. (2006) Annu Rev Immunol, 24, 419-66)). Hence, according to the present invention, a single TCR with known structure provides a scaffold for in vitro engineering with specificity and high affinity against non-cognate peptides displayed on MHC. That is, by generating mutants with degenerate residues within CDR loop residues that are most likely to directly contact peptide, libraries of mutants within a single TCR were generated in order to provide TCRs that can be developed having high affinity against non-cognate peptide-MHC antigens.

The general strategy used to discover, or generate, novel TCRs against non-cognate antigens from a single scaffold is shown in FIG. 1. The process involves: selecting a single TCR with a known structure. In this example, the human TCR called A6 was used. The A6 TCR was the first human TCR whose structure was solved (Garboczi et al. (1996) Nature, 384, 134-141), and it has been the topic of a long series of structural and biochemical studies (e.g., (Armstrong et al. (2008) Biochem J, 415, 183-96; Ding et al. (1999) Immunity, 11, 45-56; Hawse et al. (2012) J Immunol, 188, 5819-23). In addition, it has been used in heterodimer form for engineering higher affinity mutants against it's cognate antigen Tax:HLA.A2 (Li et al. (2005) Nat Biotechnol, 23, 349-54). Also, a stable version of the single-chain TCR (Vβ-linker-Vα) has been displayed on the surface in the yeast display system (Aggen et al. (2011) Protein Engineering, Design, & Selection, 24, 361-72).

Another step in the process is identifying residues within the TCR (e.g., A6) binding site that are most likely to contribute to peptide specificity. This step involved modeling a collection of peptides into the HLA.A2 molecule, docking of the A6 TCR, analysis of the frequency by which A6 TCR residues reside within 3 angstroms of each peptide.

Cloning libraries of mutants that have variability at the positions identified by structure-based analysis, as described above, is the next step. These libraries can be cloned into various display systems, such as yeast display. Phage display vectors and cloning have yielded library sizes of $10^{11}$, whereas yeast display vectors and homologous recombination steps have yielded library sizes of $10^{10}$ ((Benatuil et al. (2010) Protein Eng Des Sel, 23, 155-9).

Next, mutants that bind to specific, non-cognate pep-MHC ligands are selected. Various methods have been used for selecting variants, including affinity-based binding to immobilized ligands (phage display) or magnetic particle selections with antigens (yeast display), or fluorescent activated cell sorting with labeled-peptide-MHC antigens (yeast display). Examples of each of these steps are described further below.

Example 2

Figure 2A:
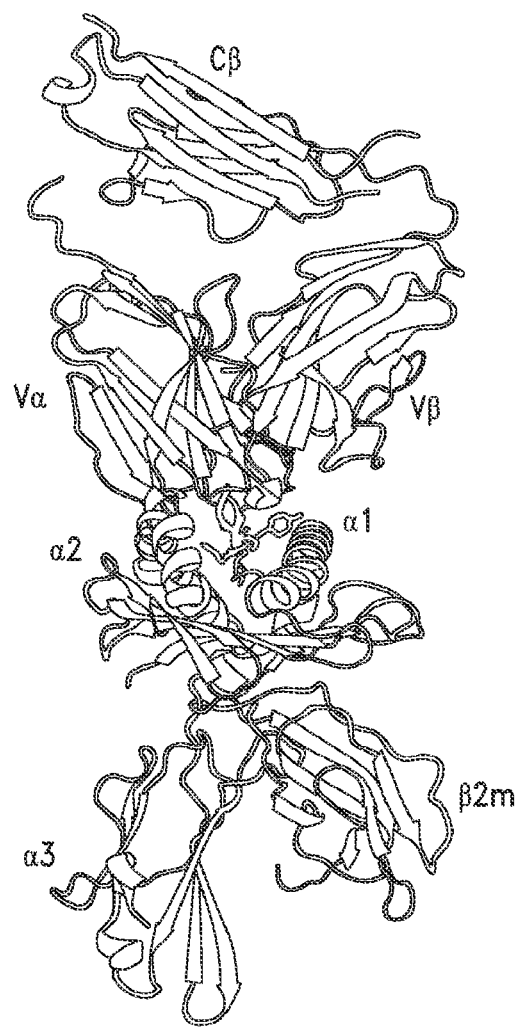
FIG. 2A is a 3-dimensional diagram that shows a structural view of the A6 TCR:pepMHC complex (A6; PDB: 1AO7). The variable (V) and constant (C) regions of the α-chain and β-chain are indicated. The structure shown does not include the Cα region of the A6 TCR. HLA-A2 (α1, α2, α3, and β2m) is shown in gray, and the Tax peptide (LLFGYPVYV; SEQ ID NO:5) is shown in black.
Figure 2B:
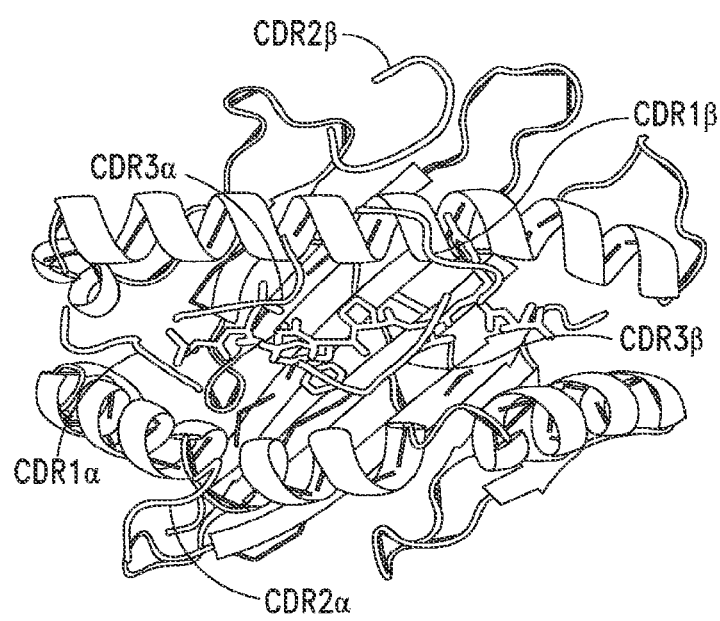
FIG. 2B is a 3-dimensional diagram that shows the CDR footprint over the peptide-MHC (Tax-HLA.A2).

Analysis of the Human TCR A6 in Complex with Tax:HLA.A2 as a Scaffold for TCR Engineering For illustrative purposes, the A6 TCR was selected as the single TCR having a known structure. The structure of the A6:Tax peptide:HLA-A2 complex (PDB: 1AO7) (Garboczi et al. (1996) Nature, 384, 134-141), was published in 1996. The side view of the complex showed that the ends of the variable domains that contained the six CDRs docked onto the Tax:HLA.A2 molecule, with the central region of the binding site positioned over the peptide Tax (FIG. 2A) The top down view of the Tax:HLA.A2 complex, with the TCR "removed", except for the six CDR loops. This view shows that the TCR adopts a diagonal position over the peptide-MHC, a finding which has now been observed for all TCR:peptide-MHC structures. In this orientation, the two CDR3 loops are positioned over the peptide, while there are various residues from CDR1 and CDR2 loops that interact predominantly with the helices of the MHC molecule. This diagonal docking orientation, with the Vα region positioned over the α2 MHC helix and the N-terminal end of the peptide, and the Vβ region positioned over the α1 MHC helix and C-terminal end of the peptide has been observed in virtually all complexes to date. The conserved features of these interactions suggested that it may be possible to use a single TCR as a scaffold, in which mutagenesis of various key "peptide-interacting" residues allowed the generation and discovery of novel TCR specificities (FIG. 2B).

Recent studies have used the A6 TCR for engineering higher affinity TCRs against the cognate antigen Tax/HLA.A2 by 1) directed evolution (Li et al. (2005) Nat Biotechnol, 23, 349-54), and 2) predictive algorithms for site-directed design (Pierce et al. (2010) Biochemistry, 49, 7050-9). According to the present invention, it is shown for the first time that it is possible to use structure-based, rational design of degenerate TCR libraries with mutations in key positions, combined with high-throughput screening to discover TCRs against non-cognate peptides bound to HLA products.

Example 3

Figure 3:
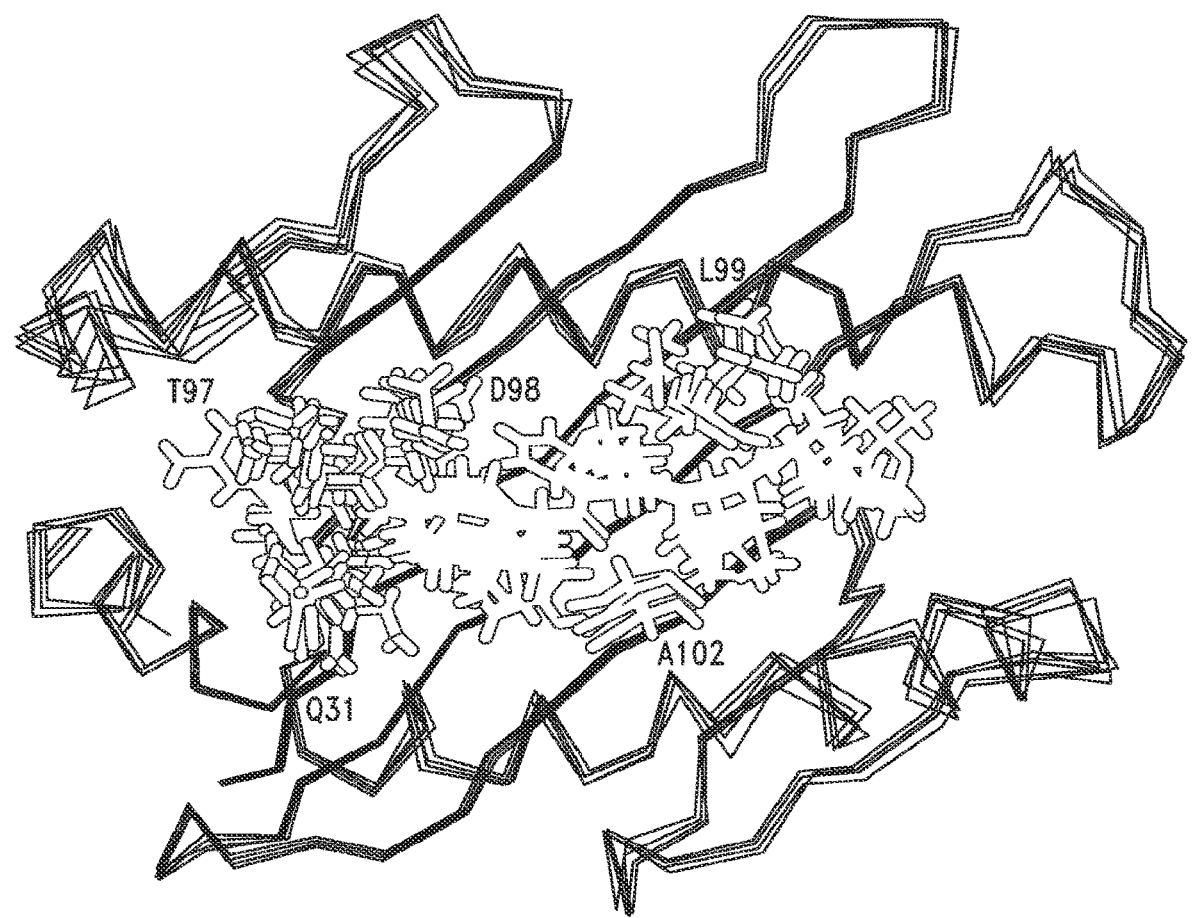
FIG. 3 is an overlay of the footprint of the 5 most encountered residues within 3.0 Å of corresponding peptide in the A6 wt and 5 predicted structures.

Analysis of the CDR Loop Residues Most Likely to Contribute to Peptide Binding and Specificity In order to identify potential contact and specificity-determining residues, various approaches were used to determine which residues of the A6 CDR loops would be most likely to accommodate, and provide binding energy to, a wide array of peptides in the HLA.A2 peptide-binding groove. First, a panel of other HLA.A2 restricted peptides was modeled into the A6 crystal structure (FIG. 3). Using the A6:Tax peptide:HLA.A2 crystal structure (PDB:1AO7) as a starting point (Garboczi et al. (1996) Nature, 384, 134-141), the Rosetta Backrub modeling program was used to model the HLA.A2 restricted peptides (i.e., Tax, Mart1-9mer, Mart1-10mer, SL9 HIV, WT1, and Survivin) into the HLA.A2 groove using Rosetta Backrub flexible backbone modeling algorithms (FIG. 3) ((Lauck et al. (2010) Nucleic Acids Res, 38, W569-75); kortemmelab.ucsf.edu/backrub/). The peptides that were modeled into the binding groove of the A6:tax:HLA-A2 structure in order to determine the A6 TCR residues that are within hydrogen boding distance (2.5-3.5 Å). Candidate residues for degeneracy were then determined by measuring which CDR loop positions would be most likely to allow for contacts with these peptides in the lowest energy conformation model for each peptide.

TABLE 2

HLA.A2 Restricted Polypeptides

| Peptide | 0 | 1 | 2 | 3 | 4 | 5 | 6 | 7 | 8 | 9 |
|---|---|---|---|---|---|---|---|---|---|---|
| Tax (wt) (SEQ ID NO: 5) | | L | L | F | G | Y | P | V | Y | V |
| Mart1 9 mer (SEQ ID NO: 6) | — | A | A | G | I | G | I | L | T | V |
| Mart1 10 mer (SEQ ID NO: 7) | E | L | A | G | I | G | I | L | T | V |
| SL9 HIV (SEQ ID NO: 8) | | S | L | Y | N | T | V | A | T | L |
| WT-1 (SEQ ID NO: 9) | | R | M | F | P | N | A | P | Y | L |
| SURV (SEQ ID NO: 10) | | L | T | L | G | E | F | L | K | L |

Two related peptides for Mart1 are listed, as both have been studied for their binding to HLA-A2. For modeling purposes, the residue in position "0" of the 10mer was omitted from the prediction.

CDR loop residues that were within 3 Å of peptide residues were determined for each of the six models. This analysis revealed that six residues (Table3) were within 3 angstroms in the majority (4/6 or 5/6) of the models. These codon positions thus served as the focus for development of A6 TCR libraries to be used for discovery of novel mutants that bind to non-cognate peptide-HLA antigens.

TABLE 3

CDR Loop Residues within 3Å of Peptide

| Loop | Contact position | Percent of structures |
|---|---|---|
| CDR1α | Q31 | 83% |
| CDR3α | D98 | 83% |
| CDR3β | L99 | 83% |
| CDR3α | T97 | 67% |
| CDR3β | A102/G102 | 67% |
| CDR3α | S99 | 67% |
| CDR3β | A100/M100 | 33% |
| CDR3β | G101/S101 | 33% |
| CDR1α | S32 | 17% |
| CDR1β | E30 | 17% |
| CDR3β | G98 | 17% |

Table 3 lists the A6 TCR residues found within 3.0 Å of peptide in the 6 structures and the percentage of structures in which it was found. Positions in bold type were used to construct a degenerate library, but other positions can be used either separately or in combination to construct additional libraries for developing TCRs against many different peptide/HLA complexes.

The positions of five residues in the A6 TCR are shown in the sequence of the single-chain form of the TCR (FIG. 5). In addition, the sequence of the stabilized, A6 single-chain TCR called A6-X15 (SEQ ID NO:3), which was engineered previously for high-affinity binding to the cognate antigen Tax:HLA.A2, is shown. This sequence also includes five framework mutations (S33A, E59D, N63D, N66K, K121I, all in the Vβ domain) and two CDR mutations (A52V and Q106L, both in the Vβ domain) that were isolated previously in a stability screen of the scTCR. This mutant also contained four CDR3β mutations (A100M, G101S, G102A, and R103Q) that yielded higher affinity binding to Tax:HLA.A2 (Li et al. (2005) Nat Biotechnol, 23, 349-54). A6-X15 also uses the highly stable Vα2 segment (IMGT: TRAV12-2), but contains a Phe49Ser Vα mutation for improved stability.

Example 4

Analysis of Binding Contributions Several CDR Residues

Several CDR residues were predicted to be involved in binding to the HLA.A2 helices and/or the Tax peptide (Borbulevych et al. (2011) J Immunol, 187, 2453-63; Marrack et al. (2008) Annu Rev Immunol, 26, 171-203). The process of engineering A6 TCR mutants that bind to different peptides bound to HLA.A2 would benefit from retaining those amino acid side chains that provide binding energy to their interaction with the HLA.A2 helices. Crystal structures of A6:pepHLA-A2 with both Tax peptide and tax peptide variants have shown pepMHC-contacts mediated predominately by α-chain residues (Ding et al. (1999) Immunity, 11, 45-56; Garboczi et al. (1996) Nature, 384, 134-141). Recent studies of Vα2-containing TCRs have described in detail putative conserved resides in the Vα2 segment that have evolved to recognize the HLA.A2 helices.

Figure 4A:
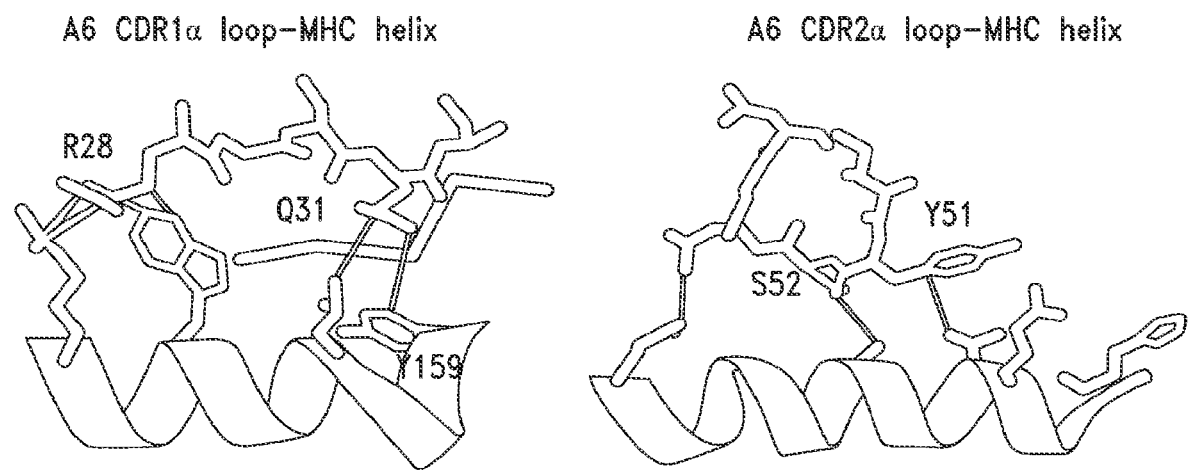
FIG. 4A depicts the crystal structures of Vα2-containing TCRs and shows predicted key MHC contact positions in the TCR CDR1a and CDR2a loops (modified from (Borbulevych et al. (2011) J Immunol, 187, 2453-63)).

FIG. 4 shows the analysis of selected A6 TCR residues for their contribution to binding of Tax:HLA.A2. In accordance with studies that have suggested these residues in CDR1 or CDR2 are important in maintaining MHC restriction, four residues of the (Aggen et al. (2011) Protein Engineering, Design, & Selection, 24, 361-72) were substituted with alanine and tested for binding. Table3 shows approximate affinities of A6 X15 alanine mutants and fold changes in binding affinity relative to wild type. The results showed that the tyrosine at position 51 of CDR2a, which contacts the α helix of HLA.A2, was most important in binding. Thus, this residue was maintained in the library described here.

TABLE 4

Alanine Substitution

| Mutant | Apparent $K_D$ | Fold Change |
|---|---|---|
| wt | 44 nM | — |
| S52A | 27 nM | 0.6X |
| R28A | 68 nM | 1.6X |
| Q31A | >4 uM | >100X |
| Y51A | >4 uM | >100X |

CDR2a residues Y51 and S52 are conserved across different α-chains and frequently bind HLA.A2 at the same position (Marrack et al. (2008) Annu Rev Immunol, 26, 171-203). Crystal structure analysis of the Vα2-containing TCRs A6, DMF4, and DMF5 have shown that CDR1a residues R28 and Q31 are important in making MHC contacts, although the exact HLA residues contacted vary. Q31 has also been shown to make contacts with peptide in addition to HLA-A2 (Borbulevych et al. (2011) J Immunol, 187, 2453-63).

Figure 4B:
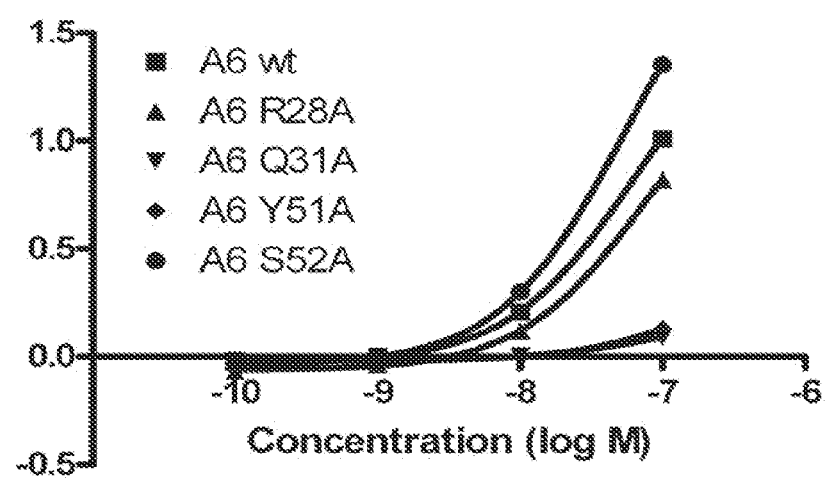
FIG. 4B shows the binding of high-affinity A6 TCR X15 and 4 variants, each having an alanine substitution at one of four residues, to various concentrations of Tax (LLFGYPVYV, SEQ ID NO:5):HLA-A2 dimer (DimerX; obtained from BD Pharmingen).

Although these Vα2 residues (R28, Q31, Y51, and S52) are important in contacting the HLA.A2 molecule, the binding energy contribution of each contact had not been previously described. In order to determine which residues contributed significant binding energy and should therefore be retained in the library, site-directed alanine mutants were made in the A6 X15 construct at each position and stained with Tax (LLFGYPVYV, SEQ ID NO:5):HLA-A2 dimer (FIG. 4B). The residue that contributed the most significant binding energy was CDR2a position Y51. Since this residue exclusively contacted MHC helices in the A6 wt structure, this residue was retained as wild type in the library. The residue that contributed the next highest binding energy was CDR1a residue Q31; however, since this residue also made contacts with the peptide in the A6 wt structure, it was randomized in the RD1 library to prevent any cross-reactivity with the cognate ligand. The other two residues examined, R28 and S52, did not contribute substantial binding energy to the A6:tax:HLA.A2 interaction, but were retained as wild type in order to prevent increased peptide-independent reactivity towards the MHC helices.

Example 5

Yeast Display and Library Construction

This example describes the preparation of a library of mutant TCRs. In order to identify novel TCRs from the single scaffold, it is necessary to use a display system in which a library of TCR mutants can be screened for the rare mutant(s) that bind to the non-cognate antigen. Three display systems have been used for engineering TCRs for higher affinity, and could be used for this process: yeast display, phage display, and T cell (mammalian cell) display. Alternative display methods, such as ribosome, RNA, DNA, and CIS display, may also be suitable for this process. In all of these cases, the wild type TCR with low affinity for the cognate antigen was cloned into the system, and used as a template for engineering higher affinity TCRs against the cognate antigen. Any of these systems could be applied to the approach described here, in which a single scaffold TCR (A6 in the present case) is used as a template for rational design of libraries and the selection of TCRs against non-cognate antigens.

Figure 6:
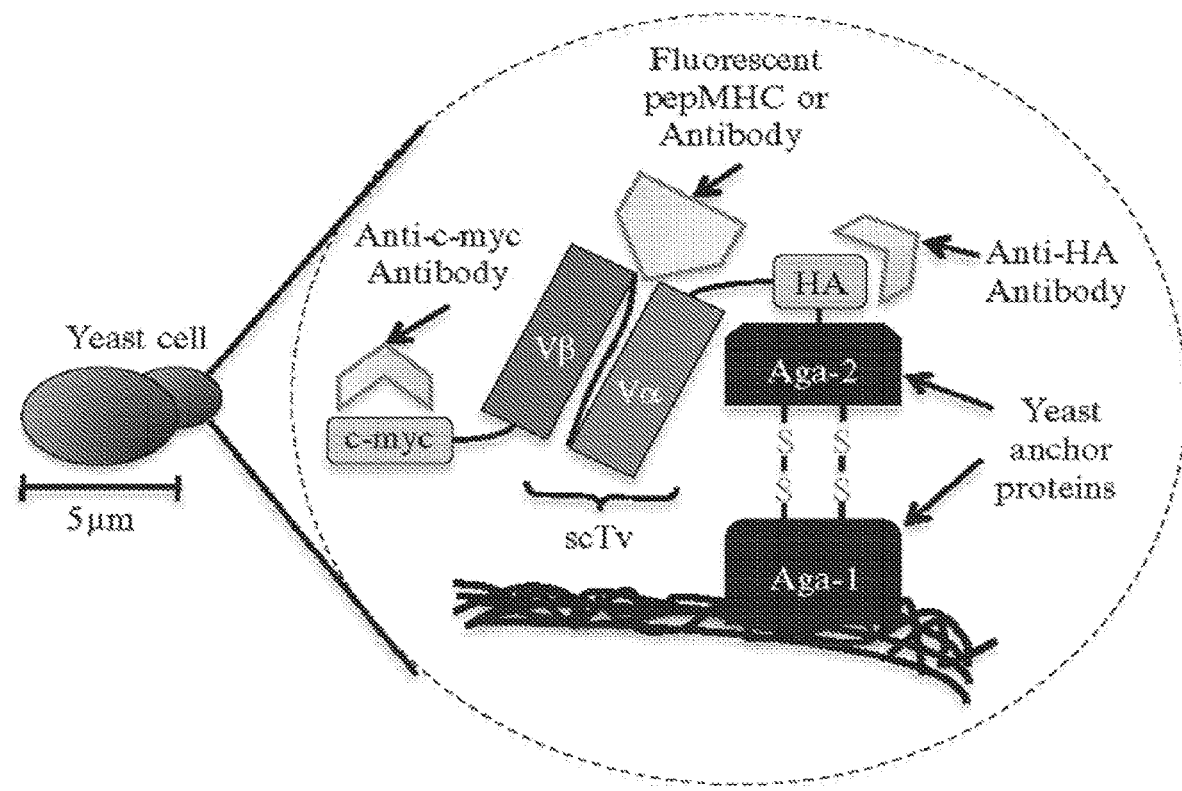
FIG. 6 is a schematic of a single-chain T cell receptor (scTCR) using yeast display.

In the present example, yeast display was used as the platform. The single-chain A6-X15 TCR was used as the template as it is stably expressed in properly folded form on the surface of yeast (FIG. 6). The gene containing degenerate codons at each of the top five positions shown in FIG. 3C and FIG. 4 was synthesized by Genscript (Piscataway, N.J., USA), and was designated the RD1 library. Genes with complete or partial codon degeneracy can now be readily synthesized by commercial sources, or can be generated by PCR using multiple synthetic oligonucleotide primers. The synthetic genes can be used as templates after cloning into a common plasmid (e.g., pET vectors) or directly as PCR product templates. Two flanking oligonucleotide primers with homology to the linearized yeast display vector were synthesized and PCR was performed in order to generate double stranded PCR products that could be inserted by homologous recombination into the yeast display vector, pCT302. The human A6-X15 scTCR library was thus introduced into the yeast display vector by combining the linearized pCT302 vector, A6-X15 RD1 library PCR product, and competent EBY100 yeast cells. The resultant RD1 library contained about $6 \times 10^6$ independent clones, was judged by plating limiting dilution aliquots of yeast after electroporation. As expected due to the diversity at each of the residues that are near the Tax peptide in the complex, the resultant library did not show positive staining with either the cognate antigen Tax:HLA-A2 or the Mart1:HLA-A2 complex as determined using peptide-HLA.A2 DimerX preparations.

In FIG. 6, a Vβ-Linker-Vα scTCR is shown with an N-terminal hemagglutinin (HA) and C-terminal c-myc tags, used to detect expression of the scTCR on the surface of yeast (Stone et al. (2012) Methods Enzymol, 503, 189-222). The scTCR construct was expressed as a fusion with the AGA-2 yeast mating protein which allows the scTCR to be expressed on the surface of yeast and rapidly analyzed via flow cytometry and screened by fluorescent activated cell sorting (FACS).

Figure 7:
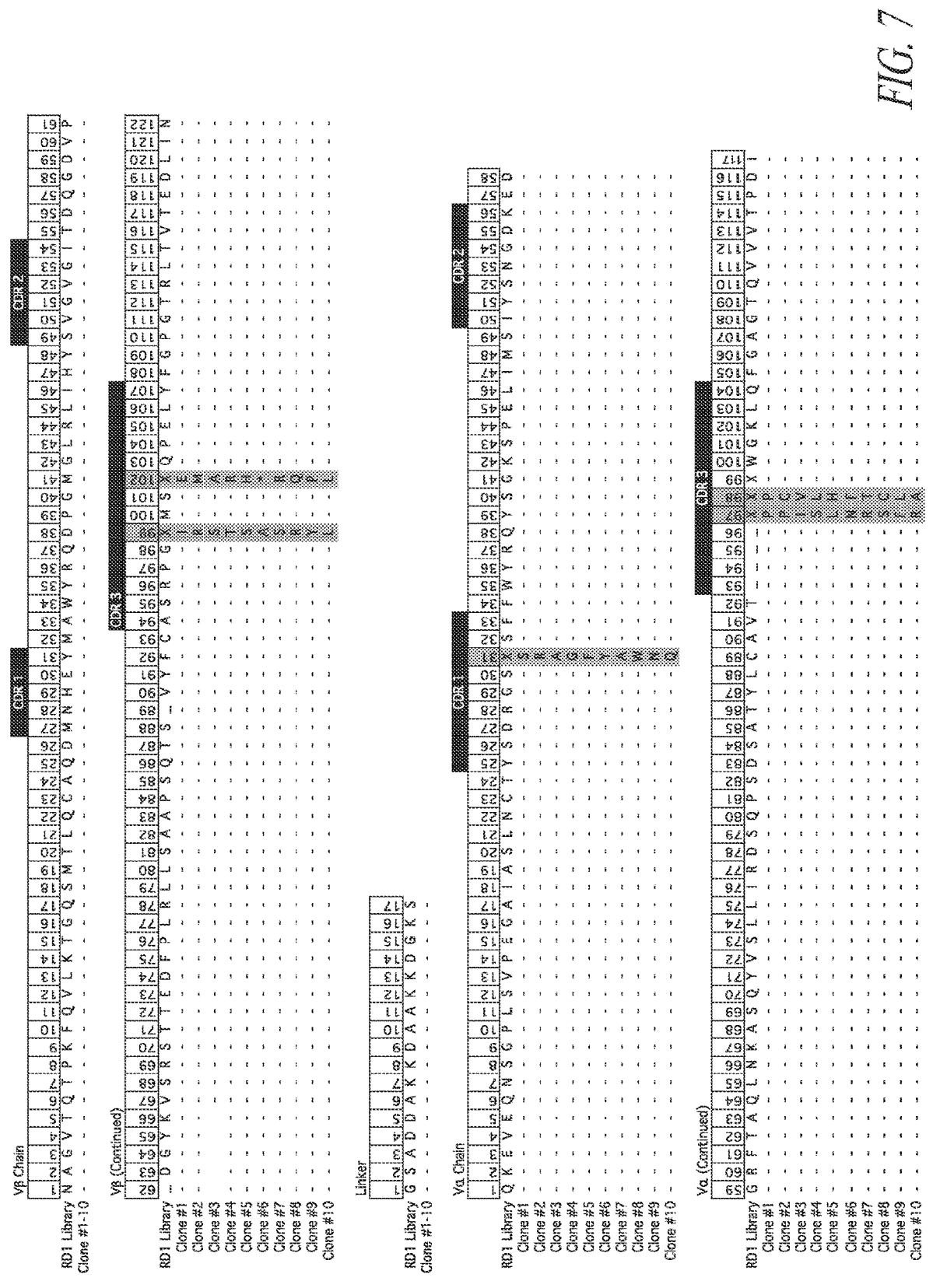

In order to verify the diversity of the RD1 library at each of the five codon positions, ten colonies from the plated library were sequenced (FIG. 7). Each of the five positions showed extensive diversity, indicating that the library contained diverse potential binding sites within the regions that were predicted to be able to contact the peptides bound to HLA.A2.

Example 6

Selection of the Yeast-Display A6 TCR Library by Cell Sorting

This example describes selecting mutant TCRs that bind to target ligands. In order to determine if the A6 scaffold library could be used to identify TCR mutants with binding to a non-cognate peptide antigen, the library was selected with the non-cognate antigen Mart1-10mer:HLA.A2, in addition to the cognate antigen, Tax:HLA.A2. These two peptides differ not only in length, but when aligned only the leucine at position 2 of Mart1-10mer (position 1 of Tax) and the valine at position 10 of Mart1 (position 9 of Tax) are identical. In addition, the valine is considered an HLA.A2 anchor residue, such that the side chains exposed to the TCR are distinctly different between the two cases.

Figure 8:
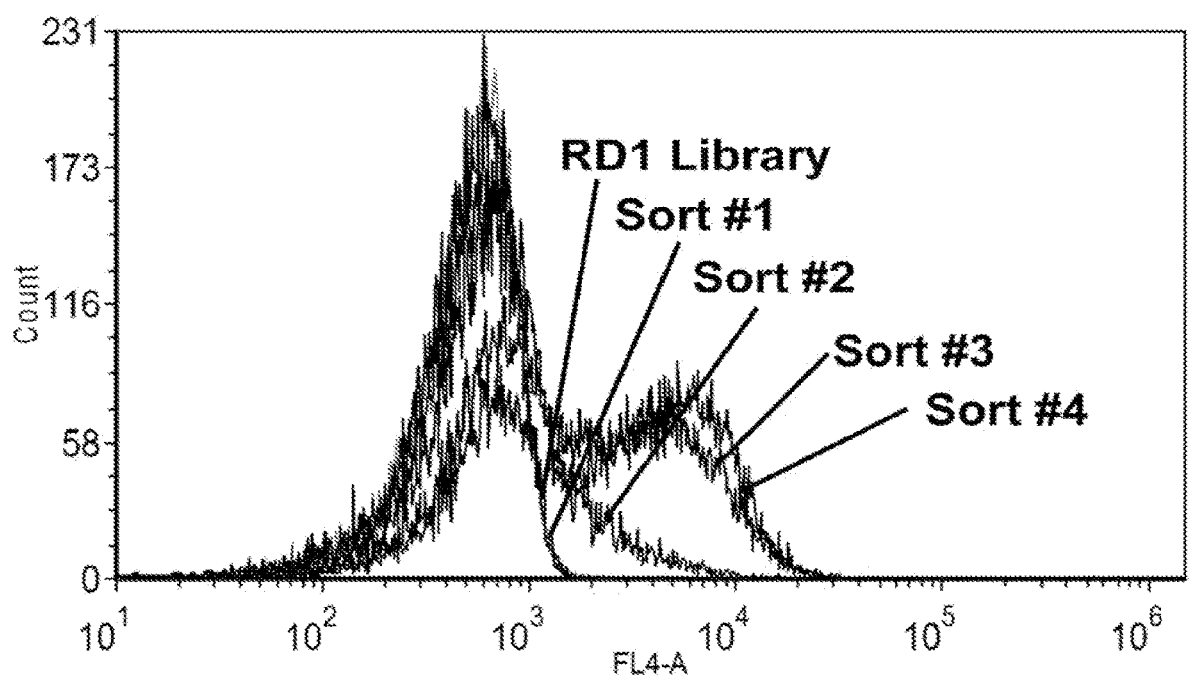
FIG. 8 shows a flow cytometry histogram of the RD1 library after sorting with the cognate antigen (Tax:HLA.A2). Gray indicates yeast cells stained with secondary antibody only.

To verify that the library contained mutants that bound the cognate antigen, fluorescent-activated cell sorting (FACS) was used with the Tax:HLA-A2 dimer (FIG. 8). The RD1 library was sorted sequentially with 10-100 nM Tax (LLFGYPVYV, SEQ ID NO:5):HLA-A2 dimer (DimerX; obtained from BD Pharmingen), APC-conjugated goat anti-mouse secondary antibody, for a total of four sorts according to Table 5. Aliquots of yeast cells after each sort were then incubated with 100 nM Tax (LLFGYPVYV, SEQ ID NO:5): HLA-A2 dimer (DimerX; obtained from BD Pharmingen), followed by APC-conjugated goat anti-mouse secondary antibody. Because the nucleotide sequences vary between clones of the same amino acid sequence, it suggests a strong selective pressure for these residues.

TABLE 4

Sorting Conditions

| Sort | Conditions |
| --- | --- |
| 1 | 20 nM Tax (SEQ ID NO: 5): HLA-A2 dimer APC-conjugated goat anti-mouse secondary antibody |
| 2 | 100 nM Tax (SEQ ID NO: 5): HLA-A2 dimer APC-conjugated goat anti-mouse secondary antibody |
| 3 | 10 nM Tax (SEQ ID NO: 5): HLA-A2 dimer APC-conjugated goat anti-mouse secondary antibody |
| 4 | 10 nM Tax (SEQ ID NO: 5): HLA-A2 dimer APC-conjugated goat anti-mouse secondary antibody |

Figure 10A:
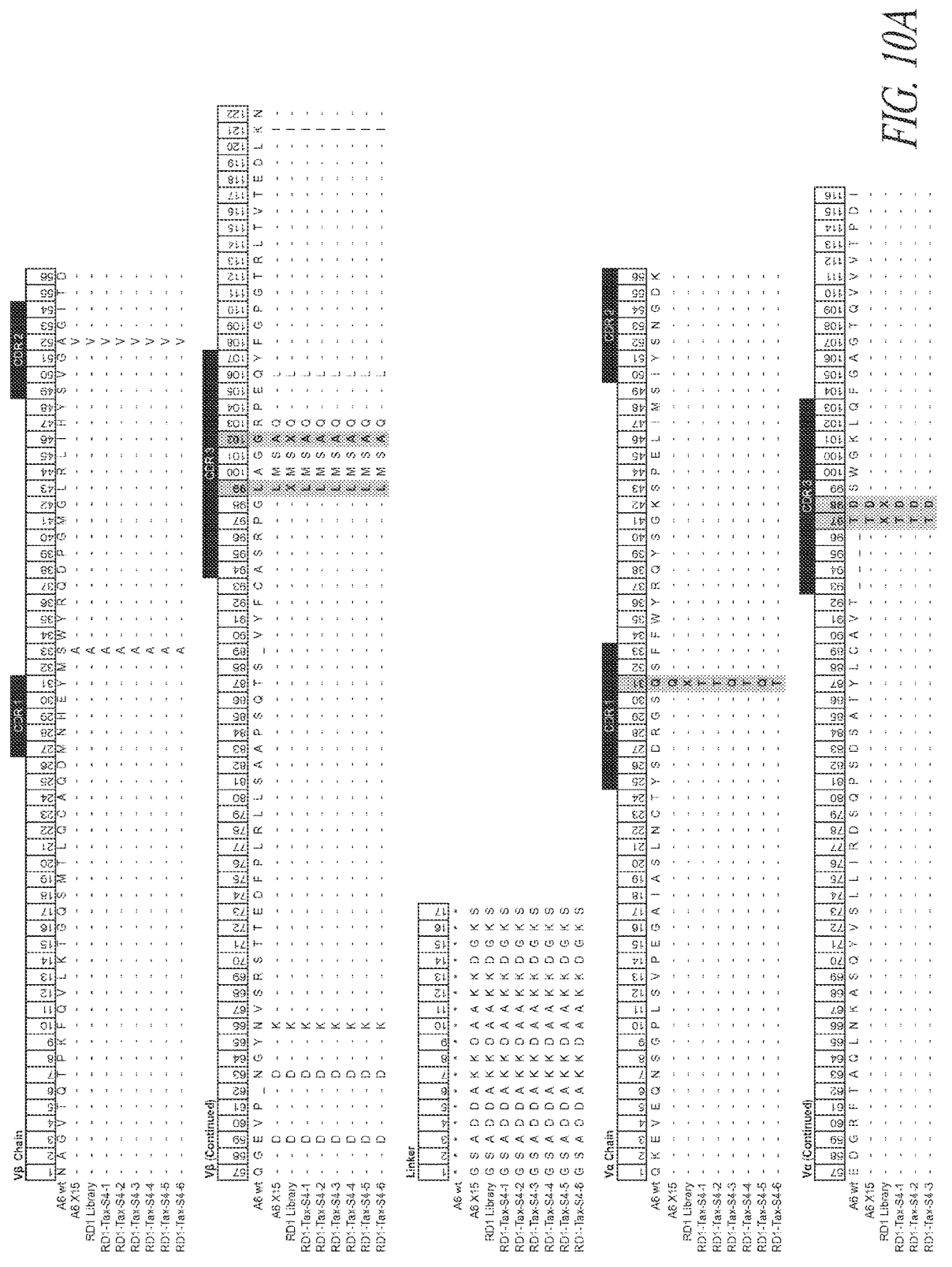

As indicated the RD1 library did not show a detectable positive peak, but after the second sorting, a positive population began to emerge, and cells were plated after the fourth sorting for additional analyses. Six clones revealed that 2 of 6 had identical amino acid sequences to A6-X15 (although the nucleotide sequences/codon usage varied) and 4 of 6 had a threonine substitution at position 31 in CDR1α. All clones had similar staining profiles. The amino acid and nucleotide sequences of the six clones analyzed are in FIG. 10.

Figure 9:
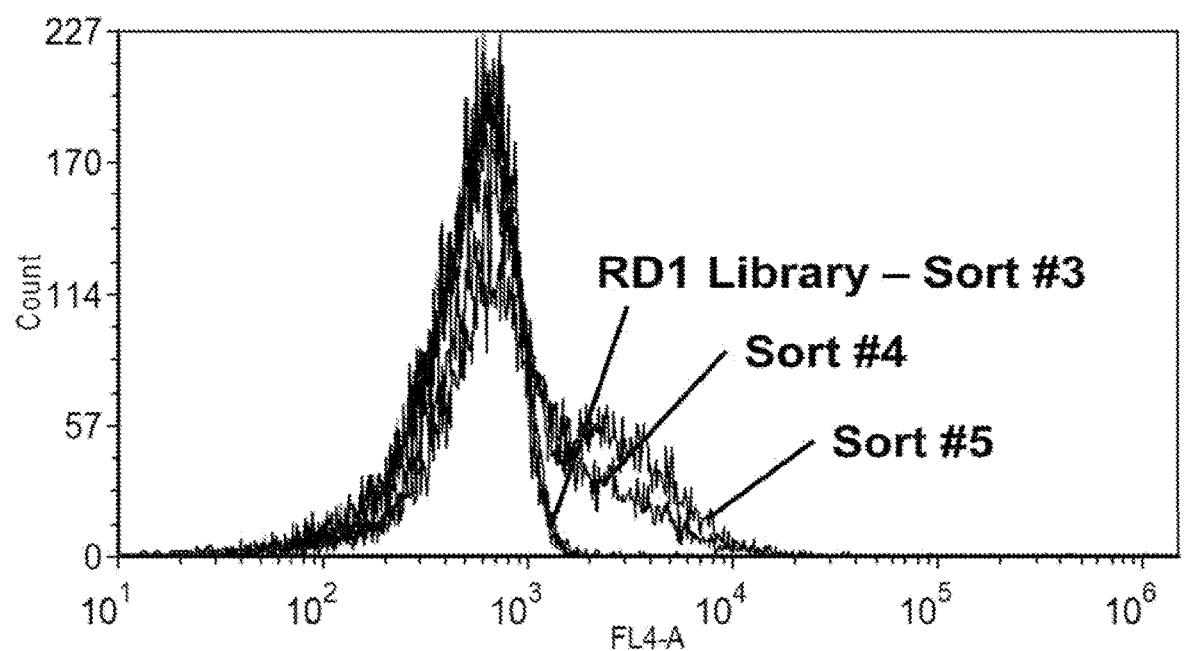
FIG. 9 shows a flow cytometry histogram of the RD1 library after sorting with the non-cognate antigen (Mart1:HLA.A2). Gray indicates yeast cells stained with secondary antibody only.

To determine whether the scaffold approach is capable of generating TCRs with non-cognate specificities, fluorescent-activated cell sorting (FACS) was used with the Mart1-10mer:HLA-A2 dimer (FIG. 9). The RD1 library was sorted sequentially with 20-500 nM Mart1 (ELAGIGILTV, SEQ ID NO:7):HLA-A2 dimer (DimerX; obtained from BD Pharmingen), APC-conjugated goat anti-mouse secondary antibody, for a total of five sorts according to Tale 5. During the 3$^{rd}$ sort, yeast cells were also stained with chicken anti-c-myc antibody, goat anti-chicken IgY alexa 647 secondary antibody and double positives were isolated in order to exclude truncated clones. (B) Aliquots of yeast cells after each sort were then incubated with 100 nM Mart1 (ELAGIGILTV, SEQ ID NO:7):HLA-A2 dimer (DimerX; obtained from BD Pharmingen), followed by APC-conjugated goat anti-mouse secondary antibody.

TABLE 6

Sorting Conditions

| Sort | Conditions |
|---|---|
| 1 | 500 nM Mart1 (SEQ ID NO: 7): HLA-A2 dimer<br>APC-conjugated goat anti-mouse secondary antibody |
| 2 | 500 nM Mart1 (SEQ ID NO: 7): HLA-A2 dimer<br>APC-conjugated goat anti-mouse secondary antibody |
| 3 | 100 nM Mart1 (SEQ ID NO: 7): HLA-A2 dimer<br>APC-conjugated goat anti-mouse secondary antibody<br>AND<br>1:100 Anti-Cmyc epitope antibody<br>FITC-conjugated goat anti-chicken secondary antibody |
| 4 | 100 nM Mart1 (SEQ ID NO: 7): HLA-A2 dimer<br>APC-conjugated goat anti-mouse secondary antibody |
| 5 | 20 nM Mart1 (SEQ ID NO: 7): HLA-A2 dimer<br>APC-conjugated goat anti-mouse secondary antibody |

The RD1 library and the first three sorts did not show detectable positive peaks, but after the fourth sorting, a positive population began to emerge, and cells were plated after the fifth sorting for additional analyses. Five clones revealed that they all had identical amino acid sequences, indicating that these residues were important in conferring high-affinity binding. Although the nucleotide sequences do not vary between clones of the same amino acid sequence, only a small amount of possible codon combinations are possible with this amino acid sequence.

Figure 12A:
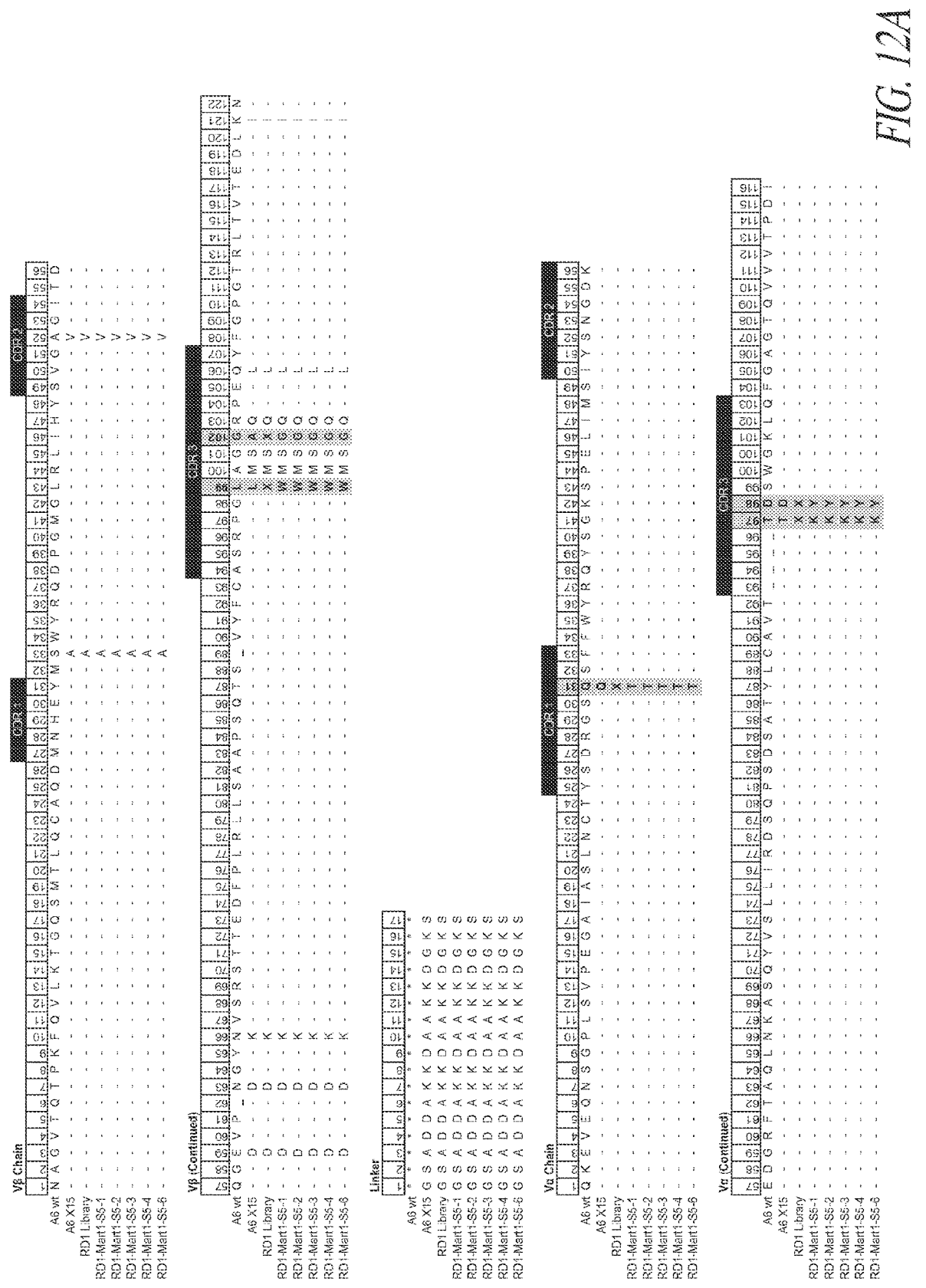

The amino acid and nucleotide sequences are shown in FIG. 12. As would be expected due to the distinctly different sequences of the Tax and Mart1 peptides, all five TCR residues, derived by sorting of the A6 library, differed between the original high-affinity TCR and the Mart1 selection. In the A6 library selection with tax:HLA.A2, the wild type sequence was encountered in 2 of 6 sequences (e.g., Tax-S4-3) and a variant containing threonine at position 31 occurred in 4 of 6 sequences (e.g., Tax-S4-1). In the Tax-specific TCR variant the five residues were: Leu99β, Ala102β, Gln31α or Thr31α, Thr97α, and Asp98α. In the Mart1-specific TCR the residues were: Trp99β, Gly102β, Thr31α, Lys97α, and Tyr98α. Although the Thr31α residue was found in both the Mart1-specific TCR and one variant of the Tax-specific TCR (e.g., Tax-S4-1), the A6 crystal structure shows this position as being important in contacting both the peptide and MHC (see FIG. 4). Due to its structural similarity to glutamine, threonine may allow for MHC contacts to be maintained without leading to cross-reactivity with other peptides.

Example 7

Binding and Specificity Analysis of Selected High-Affinity TCRs

Figure 11E:
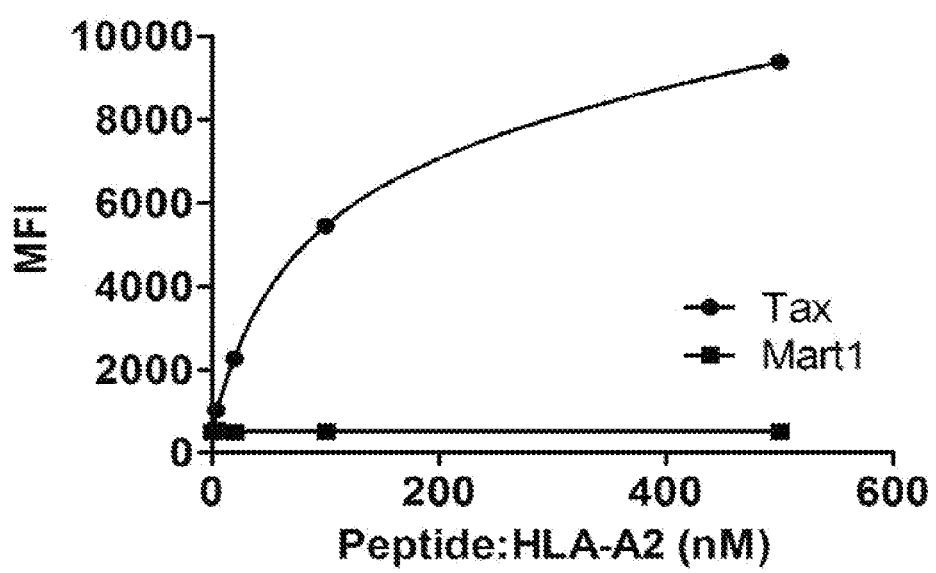
FIG. 11E is a plot of the mean fluorescence intensity (MFI) from staining with various concentrations of the peptide:HLA.A2 dimers Tax or Mart1 peptide:HLA.A2 dimer at 4-500 nM.
Figure 13A:
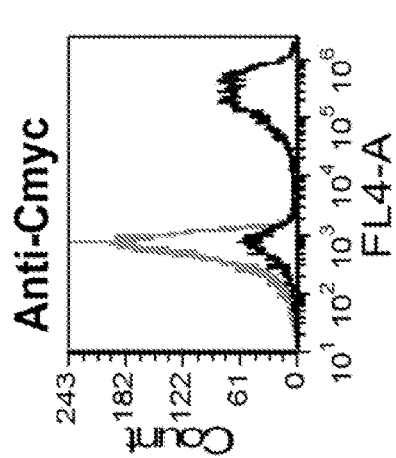
FIG. 13A is a histogram that shows positive staining of the clone with the anti-HA antibody for the N-terminal tag, and thus indicating surface expression of the AGA2 fusion. Cells were stained with anti-HA antibody and goat anti-mouse IgG alexa 647 secondary antibody (black line histogram) or secondary only as a control (gray filled histogram).
Figure 13B:
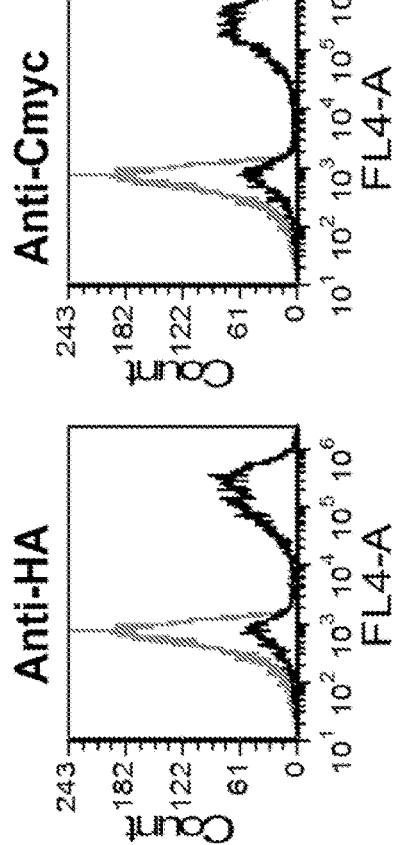
FIG. 13B is a histogram that shows positive staining with c-myc as this clone contained the C-terminal c-myc tag. Cells were stained with chicken anti-c-myc antibody and goat anti-chicken IgY Alexa 647 secondary antibody or secondary only as a control (gray).
Figure 13C:
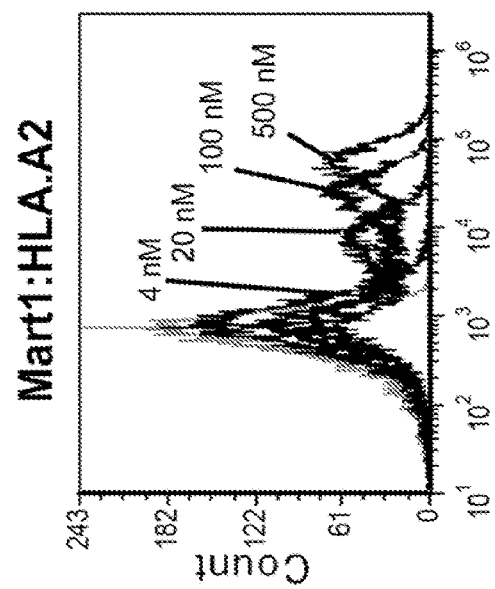
FIG. 13C is a histogram that shows staining of the A6-S5-4 clone with various concentrations of the selecting non-cognate antigen, Mart1:HLA.A2 dimer, at the indicated concentrations.
Figure 13D:
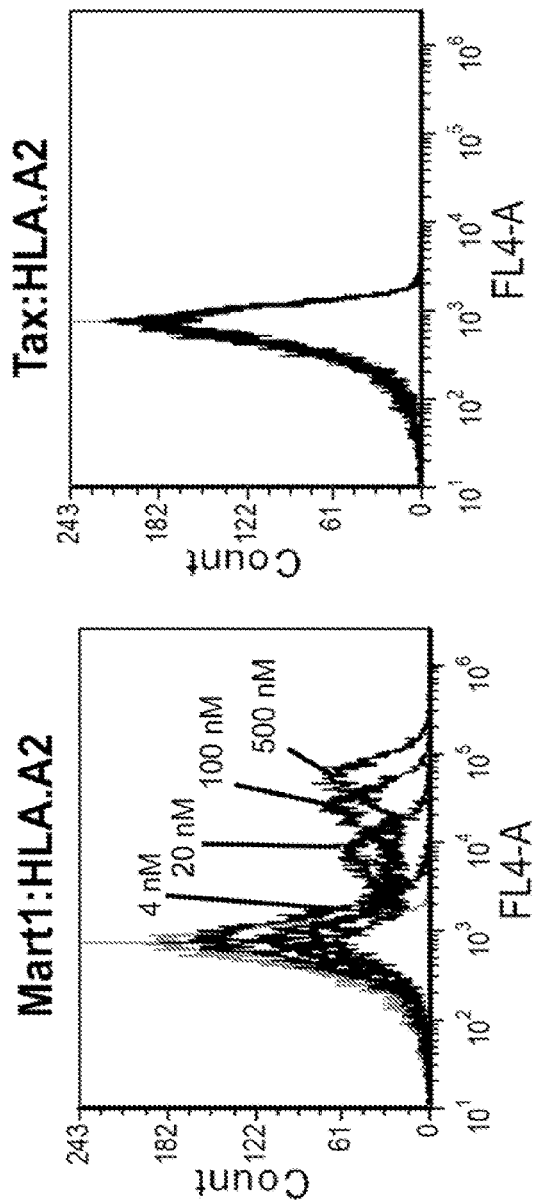
FIG. 13D is a histogram that shows the staining of the A6-S5-4 clone with various concentrations of the non-selecting cognate antigen, Tax:HLA.A2.
Figure 13E:
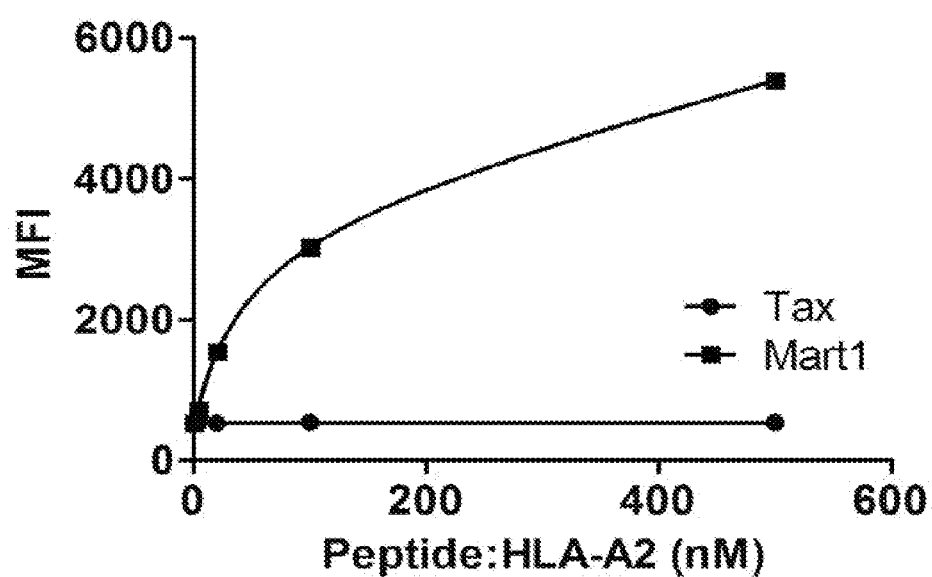
FIG. 13E is a plot of the mean fluorescence intensity (MFI) from staining with various concentrations of the peptide:HLA.A2 dimers Mart1 or Tax peptide:HLA.A2 dimer at 4-500 nM.

In order to use TCRs in the present disclosure for specific targeting of cells that express the antigens, it is critical that they exhibit peptide specificity. To determine if the TCRs selected for binding to the Tax (SEQ ID NO:5) and Mart1 (SEQ ID NO:7) peptides exhibited specificity in their reaction with the selecting peptides, representative clones for each were titrated with various concentrations of both the Tax and Mart1:HLA.A2 dimers. Clone RD1-Mart1-S5-4 which had been selected for binding to the Mart1:HLA-A2 dimer was subjected to binding analysis by titrating yeast with Mart1:HLA-A2 DimerX and tax:HLA-A2 DimerX at concentrations ranging from 4 to 500 nM (FIGS. 11 and 13).

After four sorts of the library with Tax:HLA.A2 as described in FIG. 8, individual yeast clones were cultured, induced, and analyzed for cell surface levels, and peptide: HLA.A2 binding. The A6 high-affinity mutant called X15, which was identical in amino acid sequence to two of six clones isolated after the fourth sort (data not shown), was analyzed.

After five sorts of the library with Mart1:HLA.A2 as described in FIG. 9, individual yeast clones were cultured, induced, and analyzed for cell surface levels, and peptide: HLA.A2 binding. The A6 high-affinity mutant called S5-4 (SEQ ID NO:33), which was identical in amino acid sequence to all clones isolated after the fourth sort (data not shown), was analyzed.

The Mart1-specific TCR bound only to the Mart1 complex, and not to the Tax complex, with a half-maximal concentration of binding in the low nanomolar range. Conversely, the Tax-specific TCR bound only to the Tax complex, and not to the Mart1 complex, with a half-maximal concentration of binding also in the low nanomolar range. The lack of binding even at the highest concentration indicated that the high-affinity TCR variant maintained specificity for the selecting ligand, Tax:HLA.A2. Similarly, the lack of binding even at the highest concentration indicated that the high-affinity TCR variant maintained specificity for the selecting ligand, Mart1:HLA.A2.

Example 8

Figure 15A:
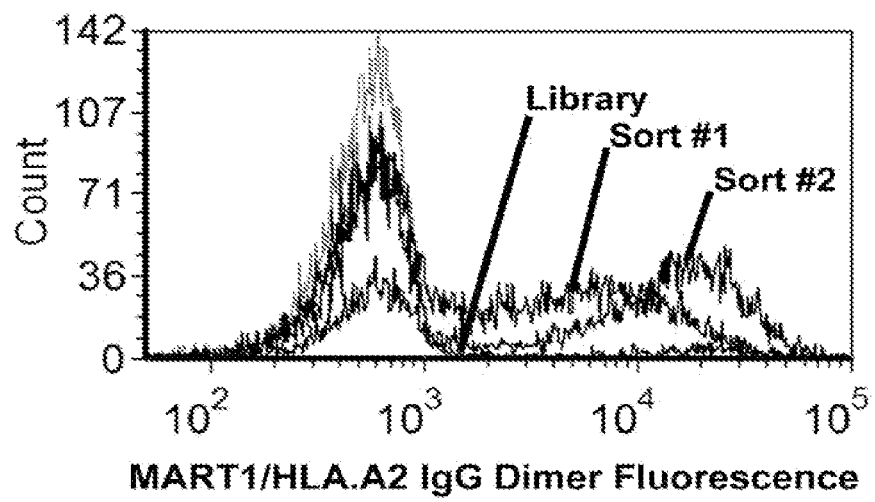
FIG. 15A shows flow cytometry histograms of the RD1-MART1-S5-4 CDR3 libraries after sorting with the non-cognate, selecting antigen, MART1 (ELAGIGILTV; SEQ ID NO:7)/HLA.A2.
Figure 15B:
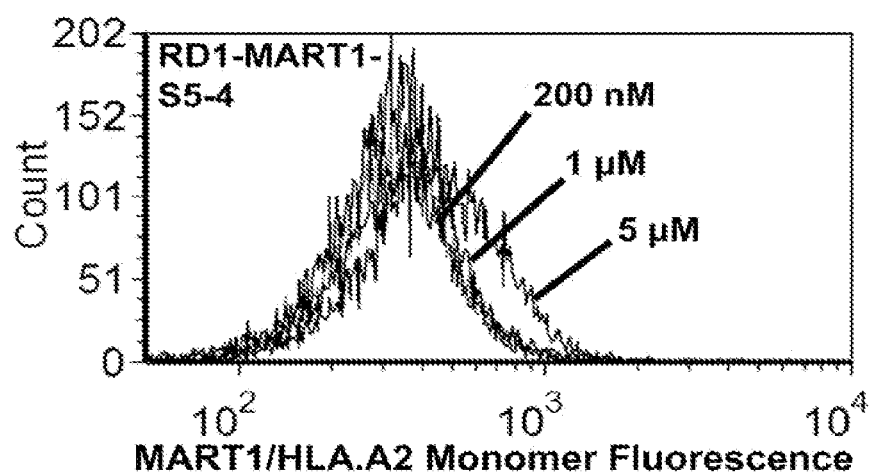
FIG. 15B is a histogram that shows staining of the RD1-MART1-S5-4 clone, which was used as a template for CDR3 affinity maturation libraries, with 200 nM, 1 μM, and 5 μM MART1 (ELAGIGILTV; SEQ ID NO:7)/HLA.A2 UV-exchanged monomers followed by PE-conjugated streptavidin.
Figure 15C:
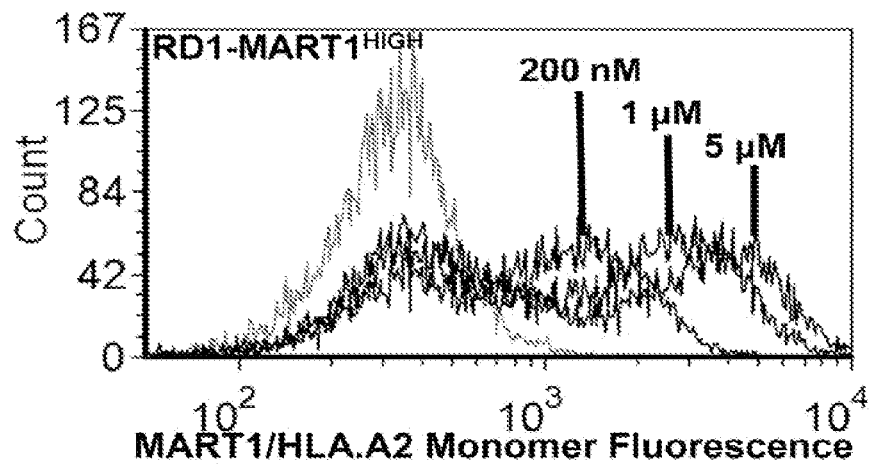
FIG. 15C is a histogram that shows staining of the RD1-MART1$^{HIGH}$ clone isolated after the second sort of the RD1-MART1-S5-4 CDR3 libraries with 200 nM, 1 μM, and 5 μM MART1 (ELAGIGILTV; SEQ ID NO:7)/HLA.A2 UV-exchanged monomers followed by PE-conjugated streptavidin.

Affinity Maturation of the MART1-Selected RD1 Scaffold Variant, RD1-MART1-S5-4 scTv Via Site Directed Mutagenesis In order to increase the affinity of the RD1-MART1-S5-4 isolated scTv (SEQ ID NO:33) for the selecting ligand MART1 (SEQ ID NO:7), degenerate libraries were made in the CDR3 loops of RD1-MART1-S5-4 in order to select for mutants for increased affinity to peptide MART1/HLA-A2/Ig dimers. The RD1-MART1-S5-4 CDR3 libraries were sorted sequentially with 1-200 nM MART1/HLA-A2 dimer (DimerX; obtained from BD Pharmingen), APC-conjugated goat anti-mouse secondary antibody, for a total of two sorts. Following two rounds of selection by FACS with MART1/HLA-A2/Ig dimers, a positively staining population of yeast that bound strongly to MART1/HLA-A2 emerged and various clones were isolated and examined for binding (FIG. 15A). Aliquots of yeast cells after each sort were then incubated with 50 nM MART1/HLA-A2 dimer (DimerX; obtained from BD Pharmingen), followed by APC-conjugated goat anti-mouse secondary antibody. One clone, RD1-MART1$^{HIGH}$ (SEQ ID NO:34), showed a significant binding increase from the template clone, RD1-MART1-S5-4, when stained with MART1/HLA.A2 monomers (FIGS. 15B and 15C).

Example 9

Specificity and Sequence of Selected RD1-MART1$^{HIGH}$ scTv

Figures 16A, 16B:
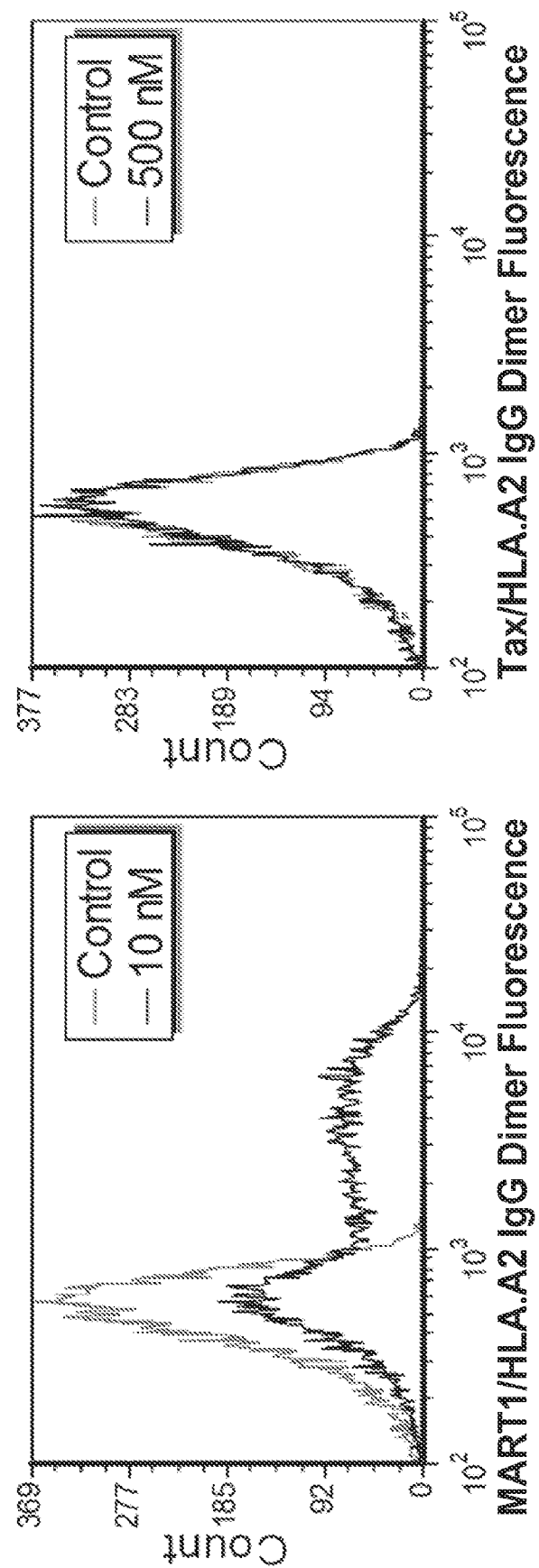
FIG. 16A is a histogram that shows the RD1-MART1$^{HIGH}$ clone stained with 10 nM MART1/HLA-A2 dimer (DimerX; obtained from BD Pharmingen) and APC-conjugated goat anti-mouse secondary antibody as a positive control. Gray indicates yeast cells stained with secondary antibody only.
FIG. 16B is a histogram that shows the RD1-MART1$^{HIGH}$ clone stained with 500 nM null Tax/HLA-A2 dimer (DimerX; obtained from BD Pharmingen) and APC-conjugated goat anti-mouse secondary antibody.
Figure 16D:
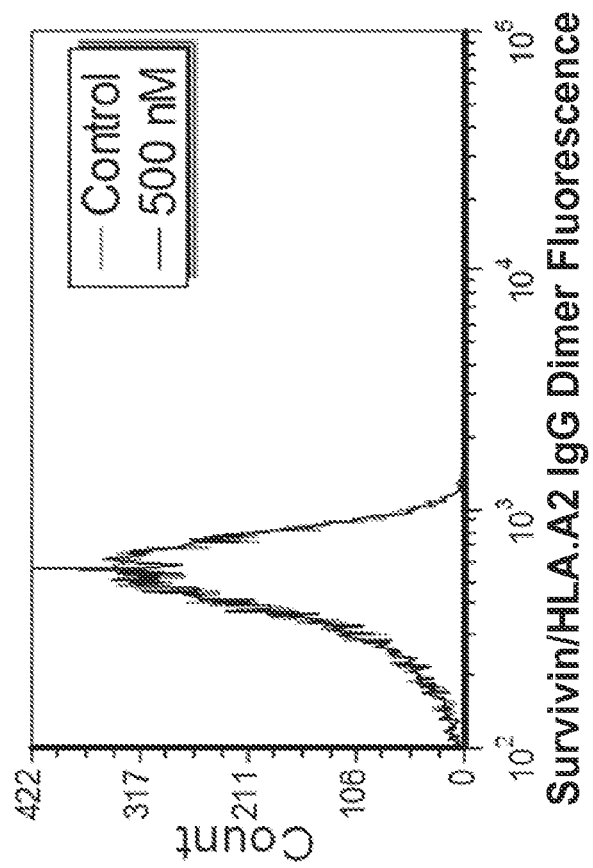
FIG. 16D is a histogram that shows the RD1-MART1$^{HIGH}$ clone stained with 500 nM null Survivin/HLA-A2 dimer (DimerX; obtained from BD Pharmingen) and APC-conjugated goat anti-mouse secondary antibody.
Figure 16C:
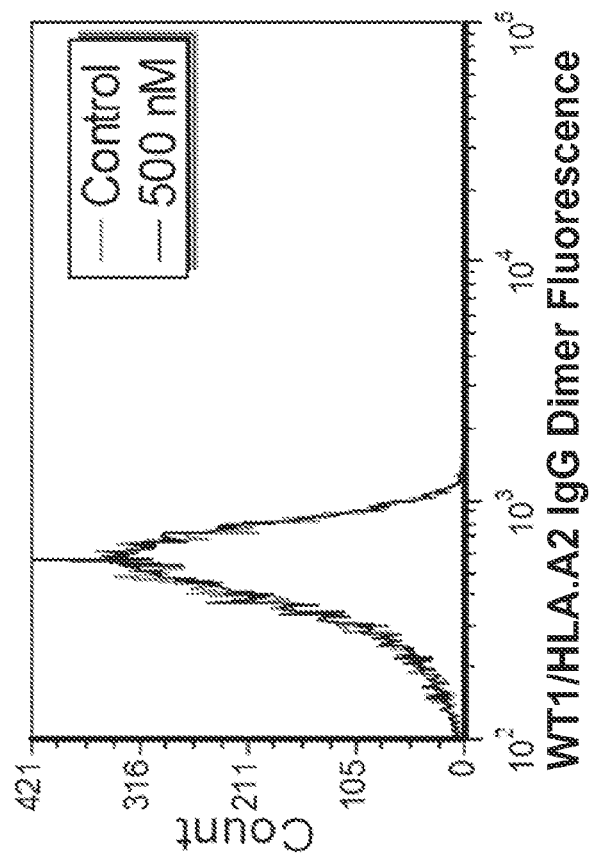
FIG. 16C is a histogram that shows the RD1-MART1$^{HIGH}$ clone stained with 500 nM null WT1/HLA-A2 dimer (DimerX; obtained from BD Pharmingen) and APC-conjugated goat anti-mouse secondary antibody.
Figure 17A:
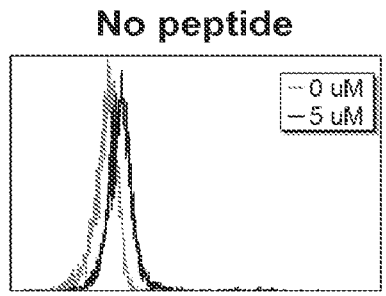
FIGS. 17A-D are a series of histograms that show flow cytometry analysis of human T2 (HLA-A2+) cells incubated first with no peptide (FIG. 17A), Tax (FIG. 17B), WT1 (FIG. 17C), or MART1 (FIG. 17D), followed by incubation with biotin-labeled RD1-MART1$^{HIGH}$ TCR.
Figure 17B:
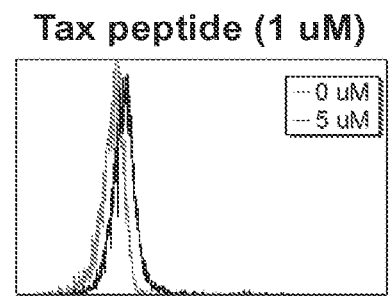
Figure 17C:
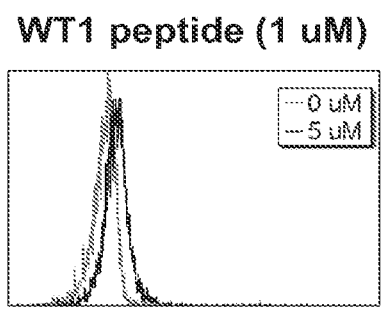
Figure 17D:
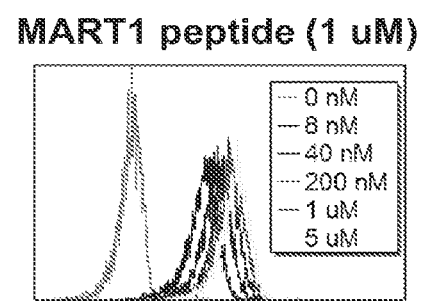
Figure 17E:
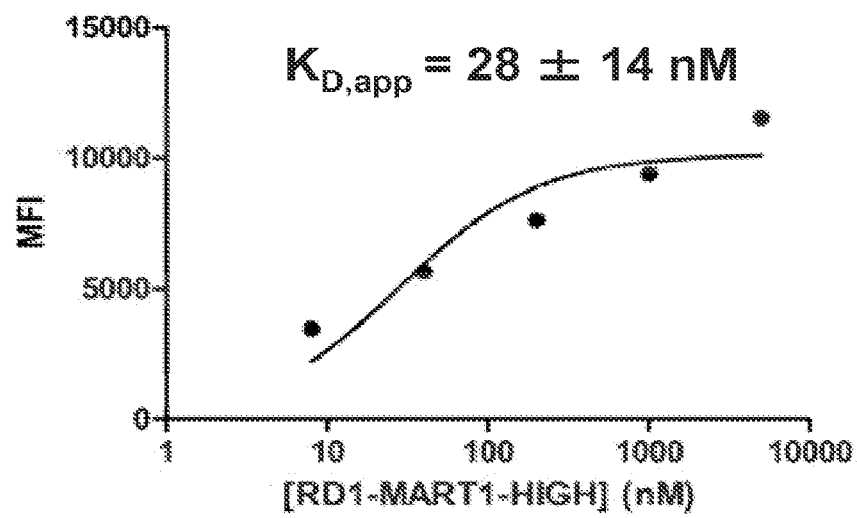
FIG. 17E is a line graph that depicts the titration showing that the RD1-MART1$^{HIGH}$ TCR had an affinity ($K_D$ value) of at least 28 nM.

In order to determine that the isolated TCR was specific only for the selecting ligand MART1, staining RD1-MART1$^{HIGH}$ with non-selecting cognate peptide Tax/HLA.A2, non-selecting non-cognate peptide WT1/HLA.A2, and non-selecting non-cognate peptide Survivin/HLA.A2 were performed. Staining showed no detectable signal with 500 nM peptide/HLA.A2 dimers suggesting the scTv was highly specific for the selecting antigen, MART1 (FIG. 16).

Figure 18:
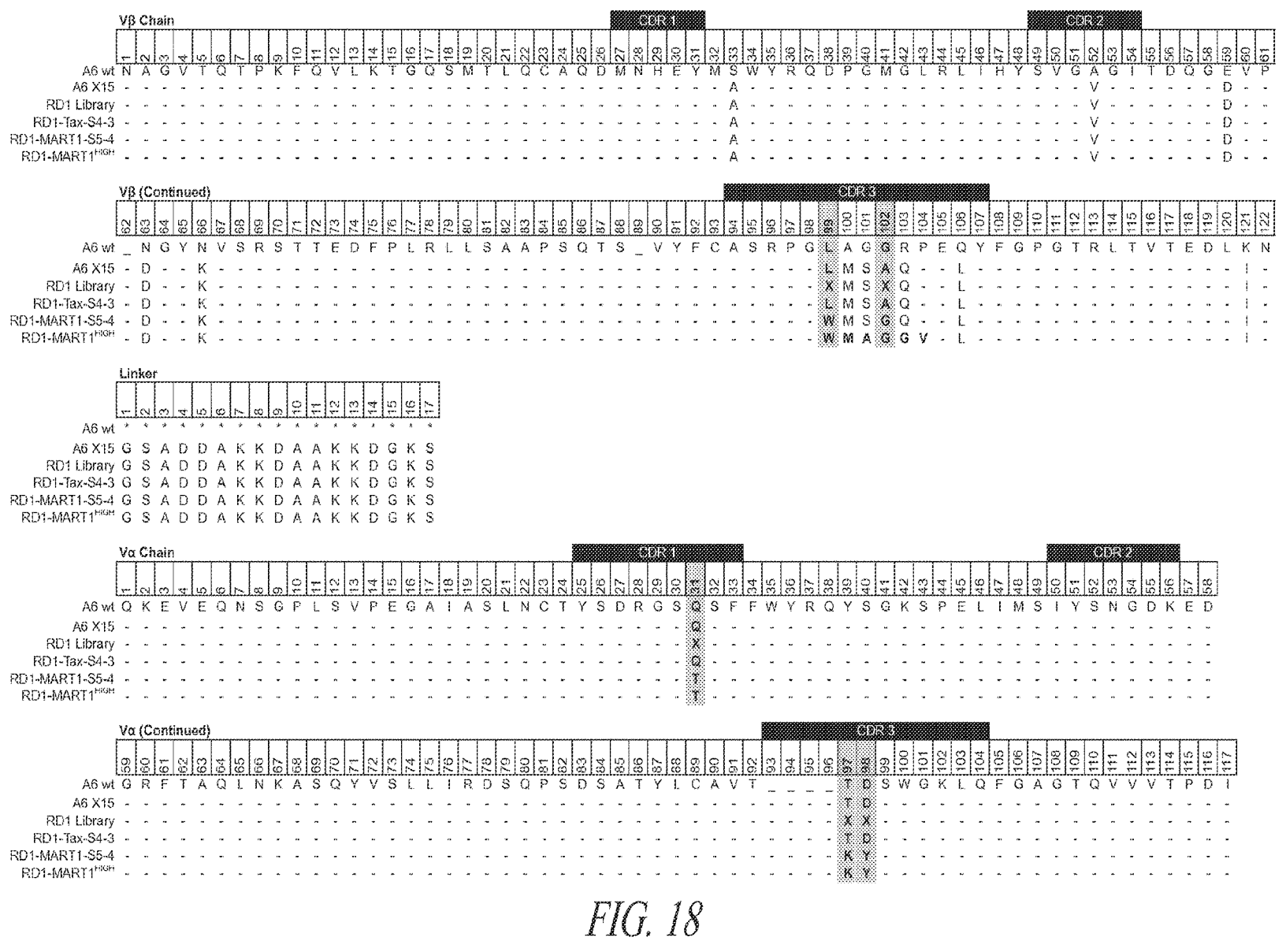

Sequences of the wild type A6 Vα and Vβ regions of the A6 TCR are shown (Garboczi et al. (1996) Nature, 384, 134-141) and the high affinity single-chain variant A6-X15 (Aggen et al. (2011) Protein Engineering, Design, & Selection, 24, 361-72) are shown in FIG. 18. Sequencing revealed that the RD1-MART1$^{HIGH}$ clone contained three mutations in CDR3β, from RD1-MART1-S5-4 template (S101A, Q103G, and P104V) (FIG. 18). Thus, compared to A6, RD1-MART1$^{HIGH}$ contained TCRα mutations Q31T, T97K, and D98Y, and TCRβ mutations L99W, A100M, G101A, R103G, P104V (SEQ ID NO:34).

To further show that the RD1-MART1$^{HIGH}$ scTv specifically bound MART1/HLA.A2 with high-affinity, a soluble form of RD1-MART1$^{HIGH}$ scTv was expressed and refolded from E. coli inclusion bodies and biotinylated via a C-terminal BirA tag (Aggen et al. (2011) Protein Engineering, Design, & Selection, 24, 361-72; Zhang et al. (2007) J Exp Med, 204, 49-55). The human cell line T2 (HLA-A2+) was incubated with 1 μM MART1, Tax, or WT1 peptides and washed. Biotinylated RD1-MART1$^{HIGH}$ scTv was titrated on T2 cells pre-loaded with MART-1 peptide (1 μM), null peptide, tax (1 μM), or without peptide. The cells were washed and incubated with SA-PE and analyzed by flow cytometry. Only cells loaded with MART1 peptide were bound by the RD1-MART1$^{HIGH}$ TCR. The results showed that the soluble TCR was specific for MART-1 and that it exhibited low nanomolar binding affinity (FIG. 17).

Example 10

Design and Selection of a Second Generation A6 Scaffold Library, RD2

Figure 19A:
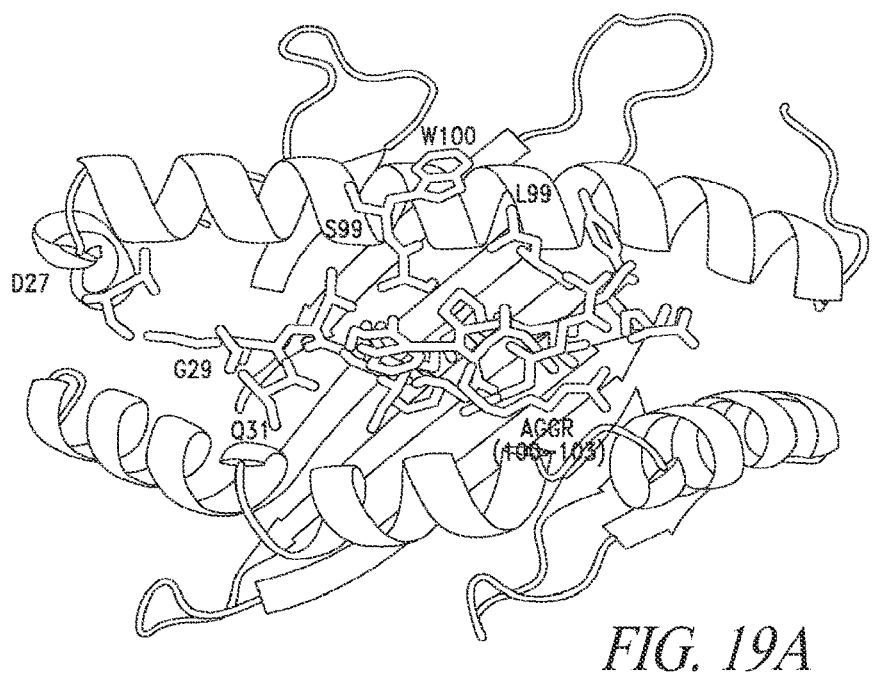
FIG. 19A is 3-dimensional diagram of the A6:Tax (LL-FGYPVYV; SEQ ID NO:5)/HLA.A2 crystal structure (PDB: 1AO7) in close proximity to an overlay of MART1 (ELAGIGILTV; SEQ ID NO:7)/HLA.A2 (PDB: 1JF1) (Sliz et al. (2001) J Immunol, 167, 3276-84) and WT1 (RMFPNAPYL; SEQ ID NO:9)/HLA.A2 (PDB: 3HPJ) (Borbulevych et al. (2010) Mol Immunol, 47, 2519-24) crystal structures. Positions labeled in bold (TCRα D27, G29, and S99; TCRβ L99 and W100) were made degenerate based on NNK nucleic acid composition. TCRα Q31 is a binary position where either the wild type residue glutamine or threonine may be selected. Positions100-103 in CDR3β are binary where the four adjacent residues may be selected as A6 wild type (AGGR, SEQ ID NO:44) or A6-X15 (MSAQ, SEQ ID NO:45).
Figure 20:
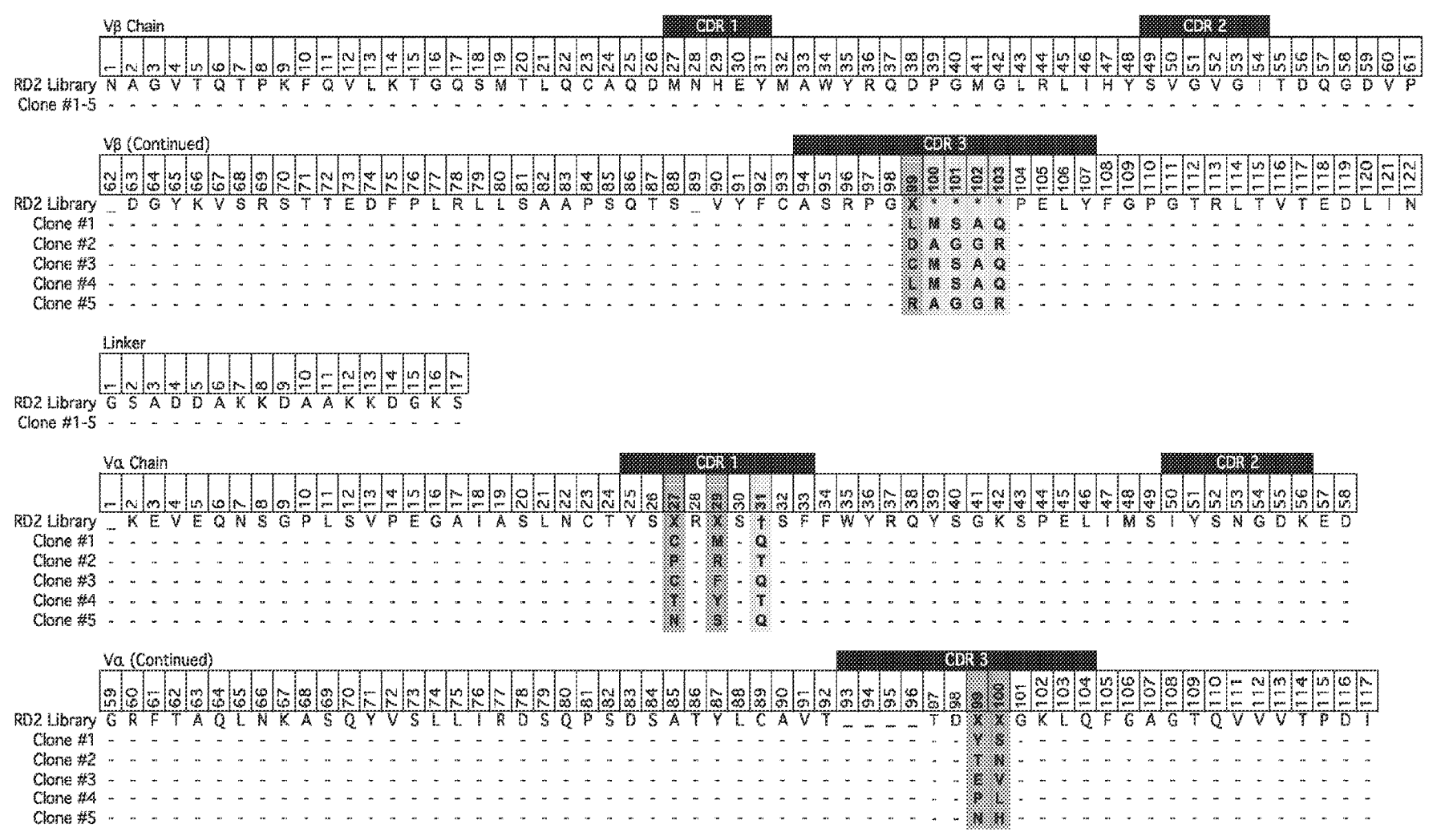

To show that the scaffold approach could work with other libraries using the A6 TCR template, the Rosetta modeling information used to generate the RD1 library (FIG. 3), and the A6:Tax/HLA.A2 crystal structure (PDB: 1AO7) overlaid with the crystal structures of MART1/HLA.A2 (PDB: 1JF1) (Sliz et al. (2001) J Immunol, 167, 3276-84) and WT1/HLA.A2 (PDB: 3HPJ) (Borbulevych et al. (2010) Mol Immunol, 47, 2519-24) (FIG. 19A), were used to guide the generation of a second generation library, called RD2. This library included 5 degenerate positions (TCRα D27, G29, and S99; TCRβ L99 and W100) based on NNK nucleic acid composition, one binary position at TCRα Q31 where either the wild type residue glutamine or threonine could be selected, and a binary sequence in position s100-103 in CDR3β where the four adjacent residues could be selected as A6 wild type (AGGR, SEQ ID NO:44) or A6-X15 (MSAQ, SEQ ID NO:45) (FIG. 20). In addition, the glutamine at position 1 of Vα2 was omitted. In order to verify the diversity of the RD2 library at each of diverse positions, five clones from the plated library were sequenced (FIG. 20).

Figure 19B:
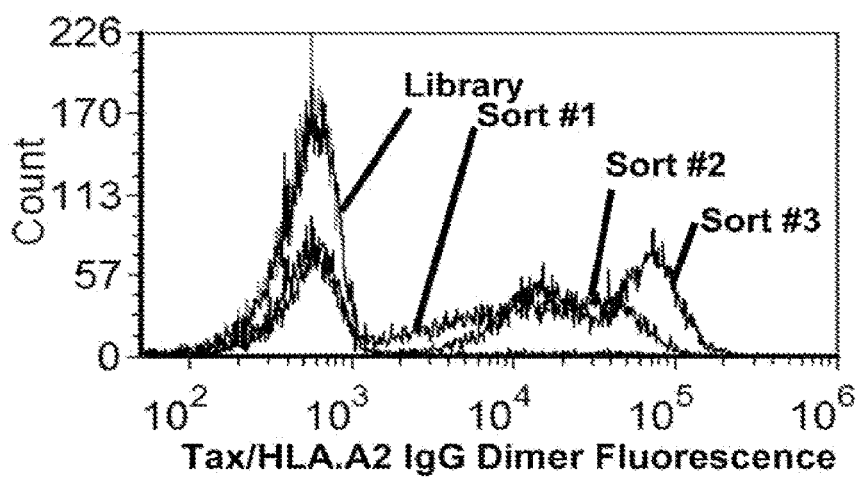
FIG. 19B is a flow cytometry histogram of the RD2 library after sorting with the selecting cognate antigen Tax/HLA.A2. Gray indicates yeast cells stained with secondary antibody only.

Two sequential magnetic bead selections of the RD2 library were performed following incubation with 5 μM Tax/HLA.A2 UV-exchanged monomers and streptavidin MACS beads (obtained from Miltenyi Biotec) (FIG. 19B). Following the second selection, yeast cells were incubated with 1 nM Tax/HLA-A2 dimer (DimerX; obtained from BD Pharmingen) and APC-conjugated goat anti-mouse secondary antibody. Aliquots of yeast cells after each selection were then incubated with 50 nM Tax/HLA-A2 dimer (DimerX; obtained from BD Pharmingen), APC-conjugated goat anti-mouse secondary antibody.

Figure 19C:
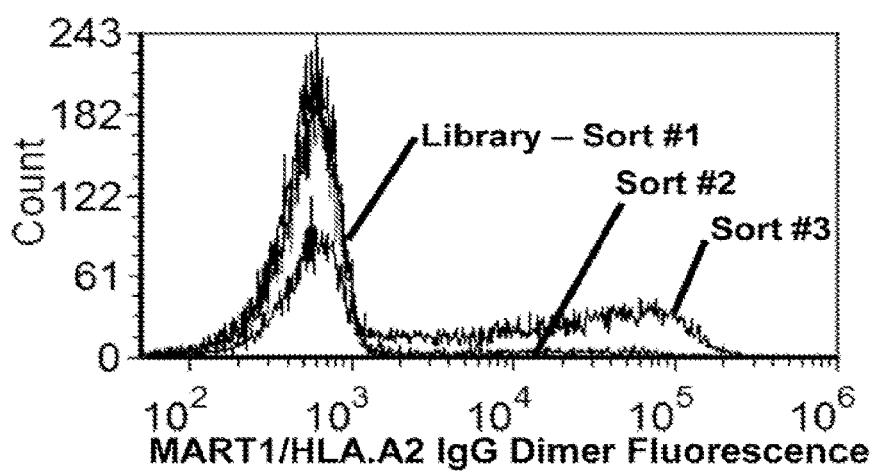
FIG. 19C is a flow cytometry histogram of the RD2 library after sorting with the non-cognate antigen MART1/HLA.A2.

Two sequential magnetic bead selections of the RD2 library were also performed following incubation with 5 μM MART1/HLA-A2 UV-exchanged monomers and streptavidin MACS beads (obtained from Miltenyi Biotec) (FIG. 19C). Following the second selection, yeast cells were incubated with 100 nM MART1/HLA-A2 dimer (DimerX; obtained from BD Pharmingen) and APC-conjugated goat anti-mouse secondary antibody. Aliquots of yeast cells after each selection were then incubated with 50 nM MART1/HLA-A2 dimer (DimerX; obtained from BD Pharmingen), APC-conjugated goat anti-mouse secondary antibody.

The RD2 library was selected with two peptide/MHC ligands, Tax/HLA.A2 (cognate) and MART1/HLA.A2 (non-cognate) via two MACS magnetic bead selections followed by one round of FACS. Selections with the cognate antigen, Tax, showed the emergence of a positively staining population after the first magnetic selection with Tax/HLA.A2 monomers (FIG. 19B). Selections with MART1/HLA.A2 revealed the emergence of a positively staining population following the third FACS selections (FIG. 19C).

Example 11

Isolation and Characterization of RD2 Variants that Bind to MART1/HLA.A2

Figure 21B:
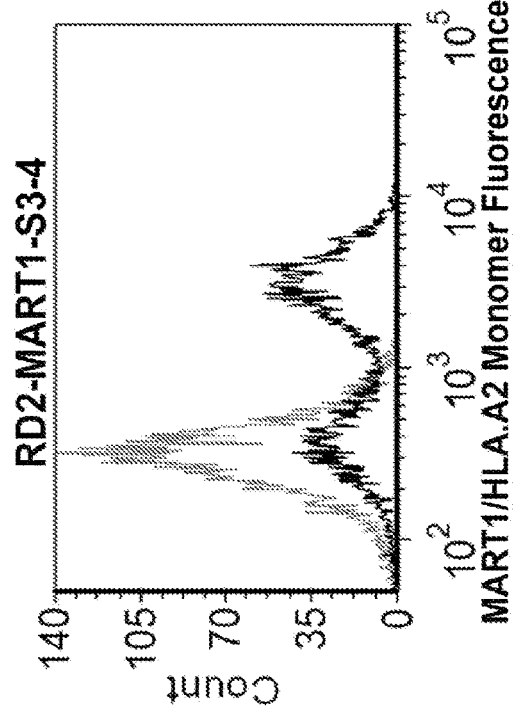
FIG. 21B is a histogram that shows the RD2-MART1-S3-4 clone, selected following the $3^{rd}$ sort of the RD2 library, stained with 2 µM MART1/HLA.A2 UV-exchanged monomers, PE-conjugated streptavidin.
Figure 21D:
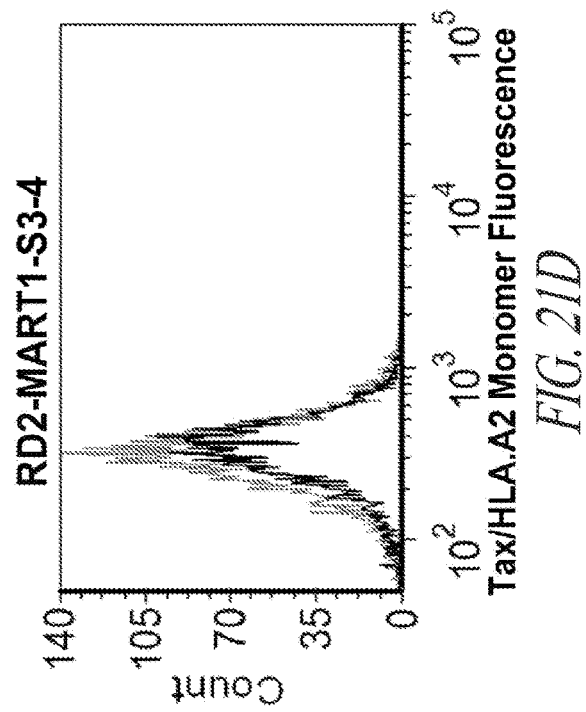
FIG. 21D is a histogram that shows the RD2-MART1-S3-4 clone, selected following the $3^{rd}$ sort of the RD2 library, stained with 2 µM null Tax/HLA.A2 UV-exchanged monomers, PE-conjugated streptavidin.
Figure 21A:
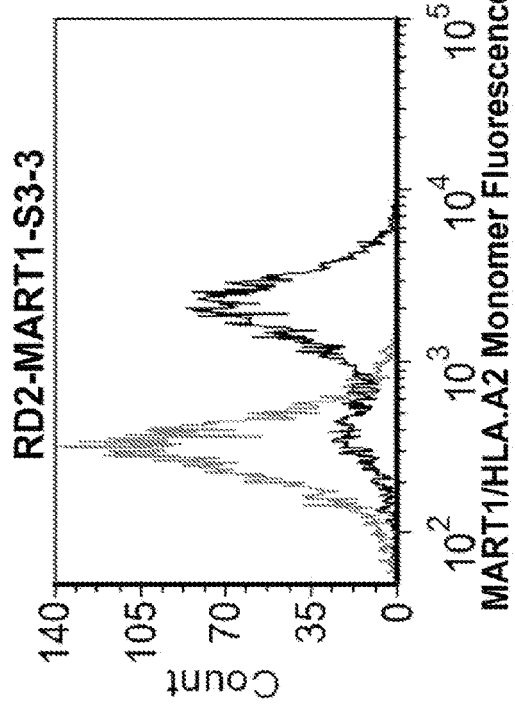
FIG. 21A is a histogram that shows the RD2-MART1-S3-3 clone, selected following the $3^{rd}$ sort of the RD2 library, stained with 2 µM MART1/HLA.A2 UV-exchanged monomers, PE-conjugated streptavidin.
Figure 21C:
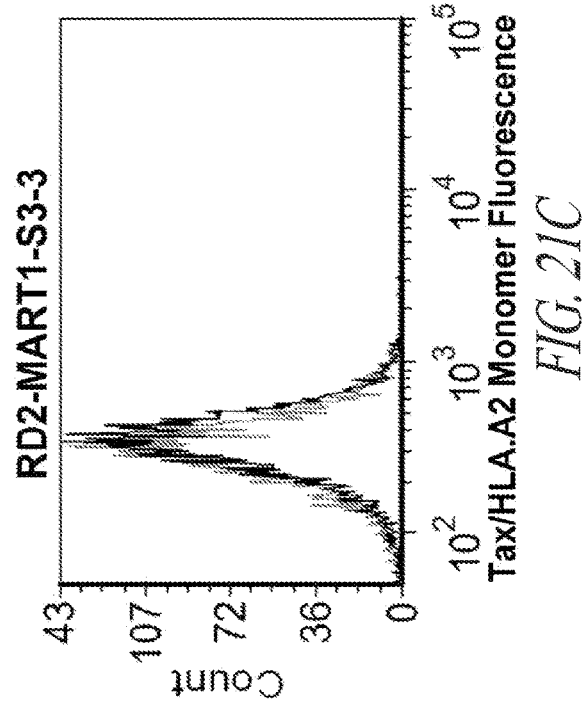
FIG. 21C is a histogram that shows the RD2-MART1-S3-3 clone, selected following the $3^{rd}$ sort of the RD2 library, stained with 2 µM null Tax/HLA.A2 UV-exchanged monomers, PE-conjugated streptavidin.
Figure 21E:
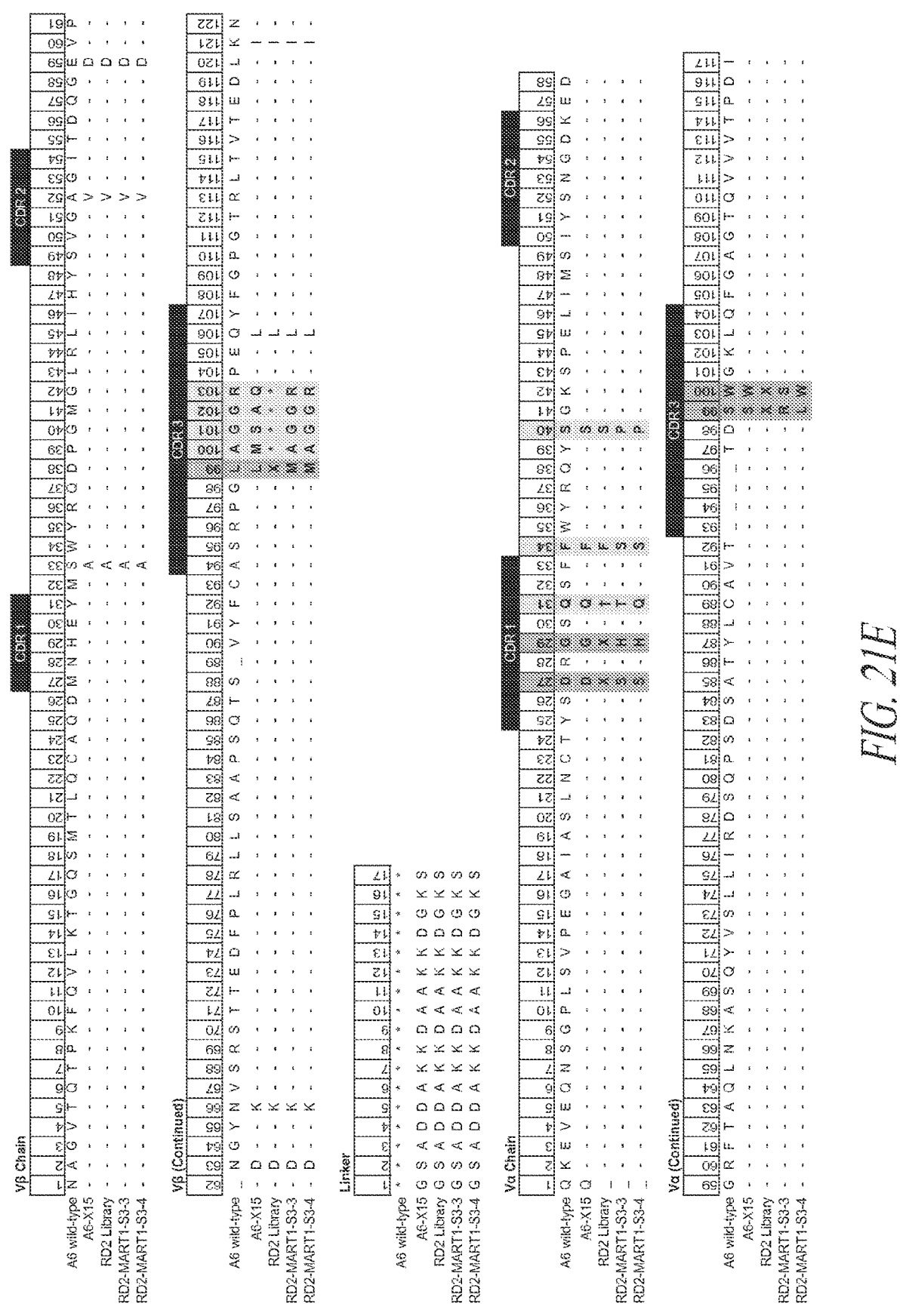

Following the third selection of the RD2 library with MART1/HLA.A2, six colonies were isolated and analyzed for improved staining for MART1/HLA.A2 (data not shown). Individual yeast clones were cultured, induced, and analyzed for peptide/HLA.A2 binding. Two clones, called RD2-MART1-S3-3 (SEQ ID NO:41) and RD2-MART1-S3-4 (SEQ ID NO:42), showed increased binding to MART1/HLA.A2 (FIGS. 21A and 21B), and did not bind to the cognate non-selecting Tax/HLA.A2 (FIGS. 21C and 21D). Sequencing analysis revealed the selection of the A6 wild-type CDR3β loop sequence AGGR (SEQ ID NO:44) for both RD2-MART1-S3-3 and RD2-MART1-S3-4. Additionally, both RD2-MART1-S3-3 and RD2-MART1-S3-4 selected TCR-β M99, TCR-α S27 and H29, and two PCR-based mutations in TCR-α (S34 and P40). Whereas RD2-MART1-S3-3 selected threonine at position 31 in CDR1α binary position, the RD2-MART1-S3-4 clone retained the wild-type Q31. Additionally, RD2-MART1-S3-3 selected TCRα R99 and S100, whereas RD2-MART1-S3-4 selected L99 and W100 (FIG. 21E).

Thus, RD2-MART1-S3-3 contained TCRα mutations D27S, G29H, Q31T, F34S, 540P, S99R, W100S, and TCRβ mutation L99M (SEQ ID NO:41) and RD2-MART1-S3-4 contained TCRα mutations D27S, G29H, F34S, 540P, S99L, and TCRβ mutation L99M (SEQ ID NO:42).

Example 12

Use of an Alternative Scaffold

Figure 22:
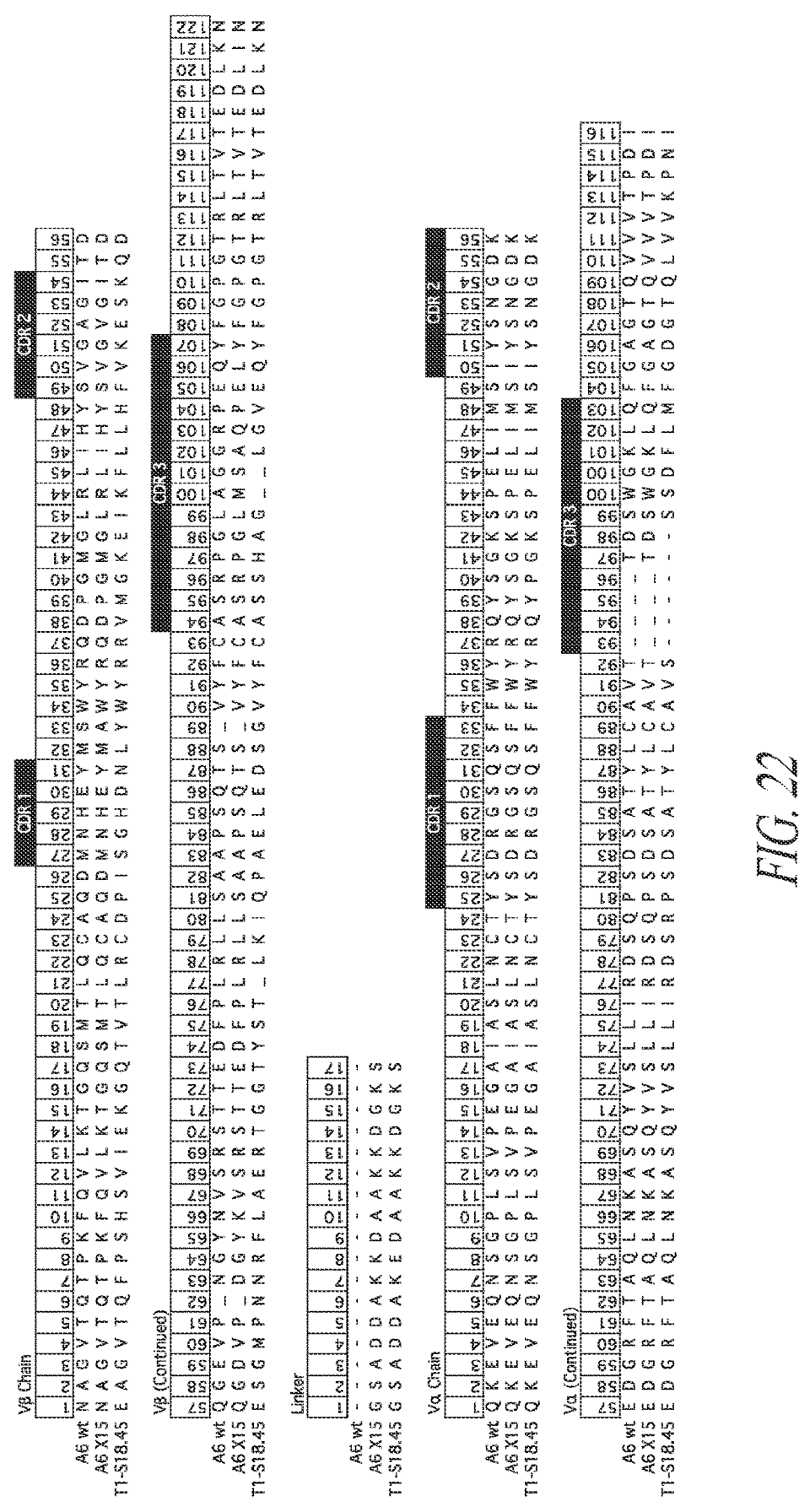

To show that other single-chain TCRs, in addition to the wild type TCR A6 and the stabilized variant of A6 known as A6 X15, another engineered high affinity scTCR known as T1-S18.45 was used as a template TCR for a single chain scaffold in the yeast display system. T1-518.45 uses Vα2 and Vβ16 and was isolated against the MART1/HLA-A2 antigen (Fleischer et al. (2004) J Immunol, 172, 162-9). The wild-type single-chain TCR was used as a template for CDR3 libraries, and affinity maturation was performed as described above. The high-affinity mutant T1-518.45 was sequenced (FIG. 22), showing that it contained the TCRα mutations N92S, D99S, N100S, A101D, and R102F (SEQ ID NO:43).

Figure 23A:
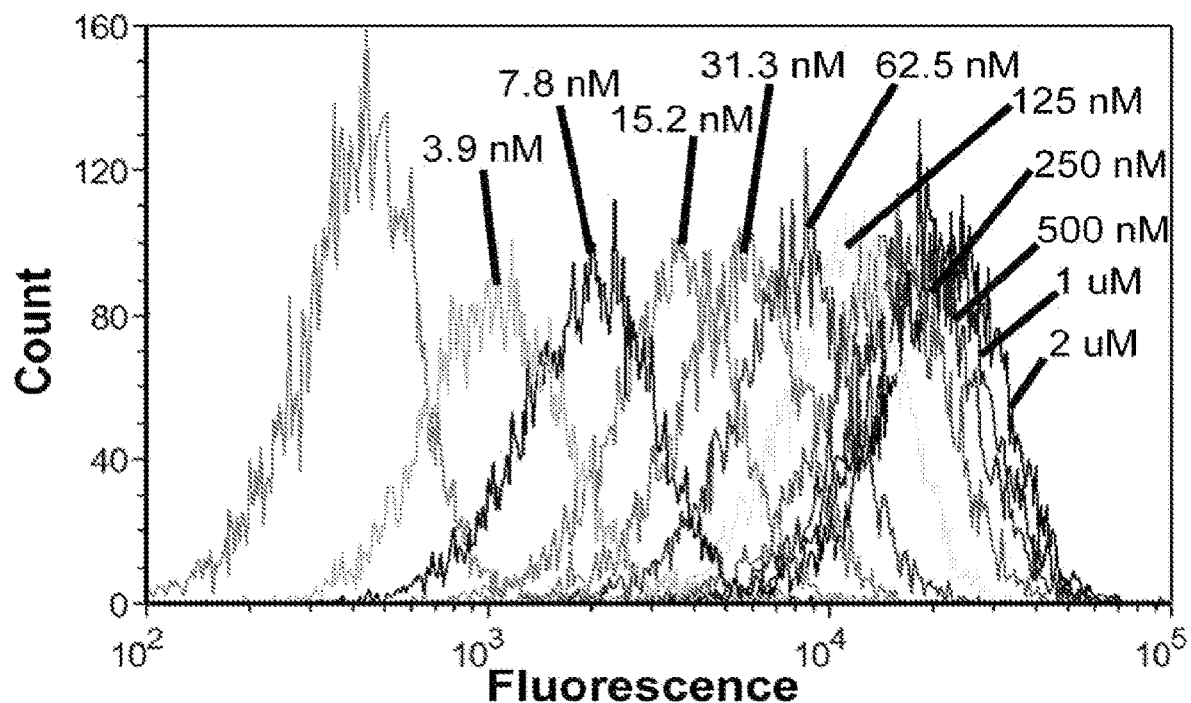
FIG. 23A is a histogram that shows the titration of biotinylated T1-S18.45 scTv on antigen-presenting cell line T2 (HLA-A2+) pre-loaded with MART-1 peptide (1 µM) or null peptide, SL9 (1 µM). Cells were stained with 3.9 nM, 7.8 nM, 15.2 nM, 31.1 nM, 62.5 nM, 125 nM, 250 nM, 500 nM, 1 µM, and 5 µM biotinylated T1-S18.45 scTv as indicated and followed by SA:PE. Data shown is representative of 4 experiments.
Figure 23B:
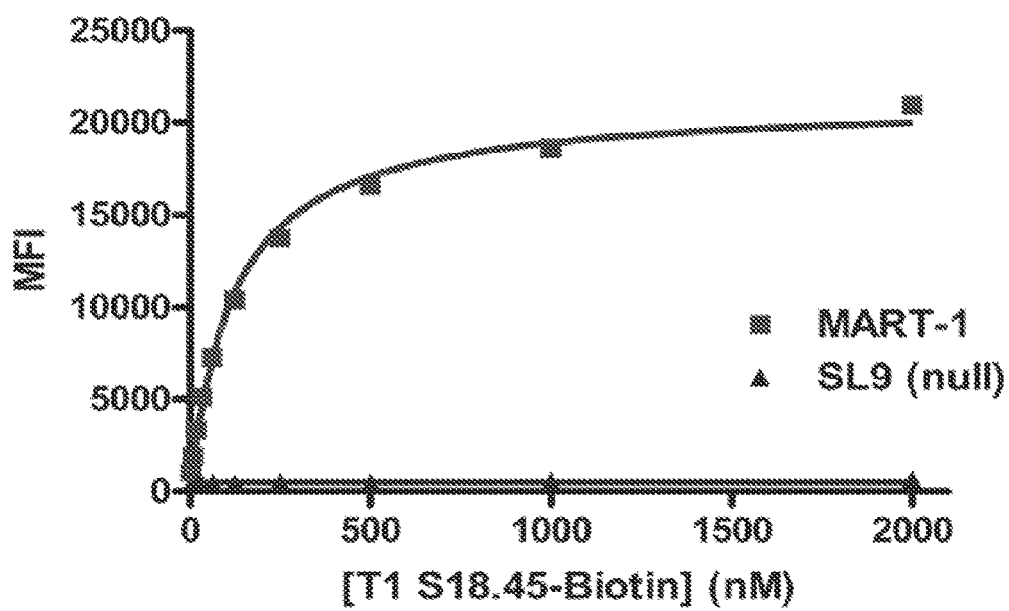
FIG. 23B is a line graph showing the mean fluorescence unit (MFU) values of histograms in FIG. 23A plotted versus scTv-biotin concentration.

To further show that the T1-S18.45 scTv bound MART1/HLA-A2 with high-affinity, a soluble form of T1-518.45 scTv was produced in E. coli and biotinylated (Aggen et al. (2011) Protein Engineering, Design, & Selection, 24, 361-72; Zhang et al. (2007) J Exp Med, 204, 49-55). Biotinylated T1-S18.45 scTv was titrated on antigen-presenting cell line T2 (HLA-A2+) pre-loaded with MART-1 peptide (1 µM) or null peptide, SL9 (1 µM). The results showed that the soluble TCR was specific for MART-1 and that it exhibited low nanomolar binding affinity (FIG. 23).

Example 13

Therapeutic Formats of TCRs Engineered Using the Scaffold Process

It is now well known that higher affinity TCRs can be used in various formats for targeting cells that express the corresponding antigen. Thus, it is clear that the TCRs generated from the scaffold strategy could be used either in soluble form or in TCR gene therapy for adoptive T cell therapies.

Figure 24A:
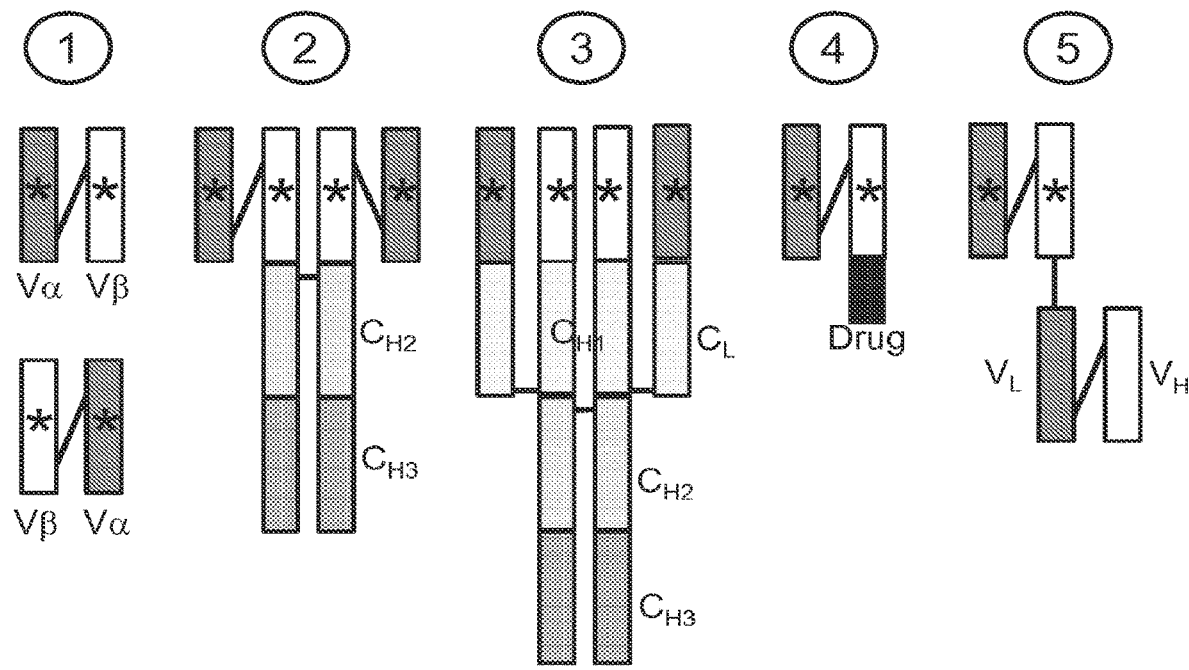
FIGS. 24A and 24B are diagrams that illustrate exemplary therapeutic applications of the high-affinity, single-chain TCRs isolated from the scaffold libraries.

As summarized in FIG. 24, the TCRs can be readily formatted for use as soluble therapeutic products, which carry a "payload" to the target cell expressing the specific peptide-MHC antigen. The formats include those already practiced in the art, including immunoglobulin fusions, chemotherapeutic or drug conjugates, and bispecific antibodies: 1) single-chain TCRs in either a Vα-Vβ orientation or Vβ-Vα orientation, expressed in soluble form for binding applications or as a platform for the other applications shown; mutated, high-affinity V domains are shown with an asterisk (*); 2) the single-chain TCR can be fused in frame with the constant regions domains of an antibody to produce an immunoglobulin fusion with effector functions and other properties of the Fc regions, as has been done with the extracellular domain of the TNF-α receptor in the product Enbrel (Brower (1997) Nat Biotechnol, 15, 1240); 3) The individual Vα and Vβ domains can be configured like a conventional antibody, as in-frame fusions to either the constant region of the light chain or the constant regions of the heavy chain, to produce an immunoglobulin fusion; 4) the single-chain TCR (or the immunoglobulin fusions shown in 2 and 3) can be directly coupled to a drug in order to endow the peptide-MHC targeting domain with a toxic compound for killing the target cell; 5) the single-chain TCR can be linked as a single-chain in-frame with a single-chain Fv (VL-linker-VH) of an antibody to produce a bispecific single-chain; the scFv can be directed against the CD3 subunits of the TCR/CD3 complex in order to recruit the activity of T cells, as has now been done with scFv-based bispecific antibodies, or more recently, a TCR-based bispecific.

Figure 24B:
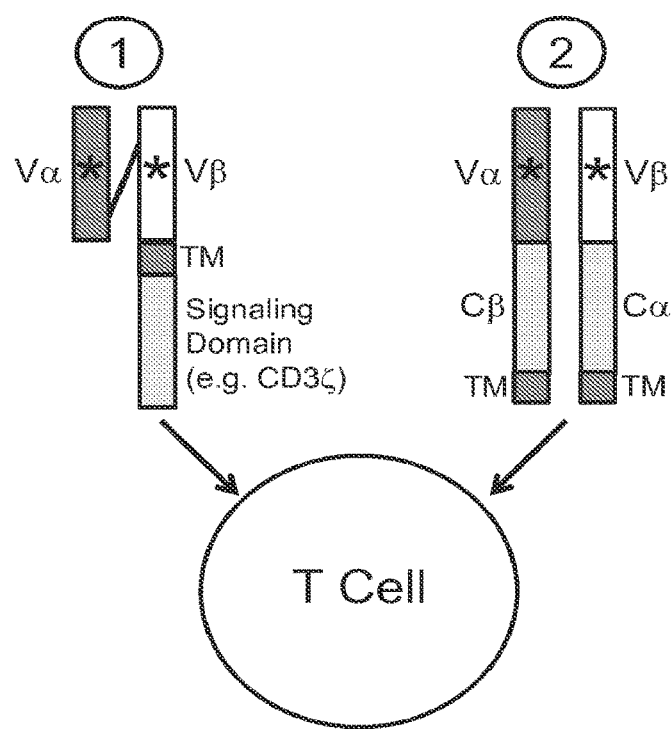

Additionally, FIG. 24B shows the variable domains (V) isolated by yeast display for high-affinity binding using the TCR scaffold can be inserted into mammalian cell vectors for expression in T cells in an adoptive T cell therapies. The TCRs can be used either as 1) single-chain receptors in chimeric antigen receptors (CAR) as is now well known, or 2) they can be cloned as full length α and β TCRs for conventional TCR gene therapy in adoptive T cell formats.

Antibodies, Peptide:HLA-A2, and Flow Cytometry

Antibodies used to detect yeast surface expression included: anti-HA epitope tag (Clone HA.11; Covance), anti-Cmyc epitope tag (Clone 9E10; Molecular Probes), Goat-anti-mouse IgG F(ab')$_2$ AlexaFluor 647 secondary antibody (Invitrogen), and Goat-anti-chicken IgG F(ab')$_2$ AlexaFluor 647 secondary antibody (Invitrogen). Peptides that bind to HLA-A2 [Tax$_{11-19}$: SEQ ID NO:5, Mart1$_{26-35\ A27L}$: SEQ ID NO:7] were synthesized by standard F-moc (N-(9-fluorenyl)methoxycarbonyl) chemistry at the Macromolecular Core Facility at Penn State University College of Medicine (Hershey, Pa., USA). For FACS and flow cytometry analysis, recombinant soluble dimeric HLA-A2:Ig fusion protein (BD DimerX) was used.

A6 RD1 Library Design

Candidate residues for degeneracy were determined by measuring which CDR loop positions would be most likely to allow for contacts with a variety of peptides using Rosetta Backrub flexible backbone modeling algorithms ((Lauck et al. (2010) Nucleic Acids Res, 38, W569-75; Smith and Kortemme (2008) J Mol Biol, 380, 742-56), kortemmelab.ucsf.edu/backrub/). Using the A6:Tax peptide:HLA-A2 crystal structure (PDB: 1AO7) (Garboczi et al. (1996) Nature, 384, 134-141) as input, Rosetta was used to model in a variety of HLA-A2 restricted peptides of interest (SL9, Mart1, WT1, Survivin) into the peptide binding groove of HLA-A2 by using the Multiple Mutation Mutagenesis module. Next, CDR loop residues that were within 3 Å of peptide residues were determined for the lowest energy conformation of each model, and the 5 most frequently encountered positions were made degenerate using A6 X15 scTCR, which contains stabilizing mutations as previously described, as a template (Aggen et al. (2011) Protein Engineering, Design, & Selection, 24, 361-72).

Computational design methodology to improve affinities of T cell receptors for their cognate peptide-MHC has been described (Haidar et al. (2009) Proteins, 74, 948-60; Hawse et al. (2012) J Immunol, 188, 5819-23). In this design method, called ZAFFI, single point mutations are modeled and analyzed for improved binding. Next, point mutations that increase binding were combined and analyzed for additive effects. This algorithm has been used to describe an A6 variant containing 4 mutations that bound 99 times more tightly than the wild type TCR (Haidar et al. (2009) Proteins, 74, 948-60). In a later study, the same methodology was used to design a higher affinity variant of the Mart-1 specific TCR DMF5. The high affinity DMF5 variant contained 2 mutations that increased the affinity 250-fold (Hawse et al. (2012) J Immunol, 188, 5819-23). The use of computational approaches to engineer T cell receptors with de novo affinities for non-cognate ligands has not been described. The present invention provides for the first time the use of computational modeling to guide scaffold generation to be used for directed evolution.

Candidate residues for degeneracy were determined by measuring which CDR loop positions would be most likely to allow for contacts with a variety of peptides using Rosetta Backrub flexible backbone modeling algorithms (Lauck, 2010 #7691}; kortemmelab.ucsf.edu/backrub/). Using the A6:Tax peptide:HLA-A2 crystal structure (PDB: 1AO7), Rosetta was used to model in a variety of HLA-A2 restricted peptides of interest (SL9, Mart1, WT1, Survivin). Next, CDR loop residues that were within 3 Å of peptide residues were determined for each model, and the 5 most frequently encountered positions were made degenerate using A6 X15 scTCR, which contains stabilizing mutations as previously described, as a template (Aggen et al. (2011) Protein Engineering, Design, & Selection, 24, 361-72).

Library Generation, Display, and Selection

The A6 RD1 Library was expressed in yeast display plasmid pCT302 (Vβ-L-Vα) (Boder and Wittrup (1997) Nat. Biotech., 15, 553-557; Boder and Wittrup (2000) Methods Enzymol, 328, 430-44), which contains a galactose-inducible AGA2 fusion allowing for growth in Trp media. Induction of the scTv gene involves growth of the transformed EBY100 yeast cells to stationary phase in selection media followed by transfer to galactose-containing media.

The A6 RD1 Library was synthesized by Genscript (Piscataway, N.J., USA) using A6 X15 as a template (Aggen et al. (2011) Protein Engineering, Design, & Selection, 24, 361-72; Li et al. (2005) Nat Biotechnol, 23, 349-54). The construct consisted of the variable fragments attached by the linker region GSADDAKKDAAKKDGKS (SEQ ID NO: 21) (Aggen et al. (2011) Protein Engineering, Design, & Selection, 24, 361-72; Kieke et al. (1999) Proc Natl Acad Sci USA, 96, 5651-6; Soo Hoo et al. (1992) Proc. Natl. Acad. Sci., 89, 4759-4763; Weber et al. (2005) Proc Natl Acad Sci USA, 102, 19033-8), and N-terminal HA and C-terminal Cmyc epitope tags. The following gene was synthesized where regions indicated by "X" were made degenerate by NNS codons: NAGVTQTPKFQVLKTGQSMTLQCAQ-DMNHEYMAWYRQDPGMGLRLIHYSVGVGITDQG-DVPDGYKVSRSTTEDFPLRLLSAAPSQTSVYFCAS-RPGXMSXQPELYFGPGTRLTVTEDLINGSADDAKK-DAAKKDGKSQKEVEQNSGPLSVPEGAIASLNCTY-SDRGSXSFFWYRQYSGKSPELIMSIYSNGDKEDGR-FTAQLNKASQYVSLLIRDSQPSDSATYLCAVTXXSW-GKLQFGAGTQVVVTPDIEQKLISEEDL** (SEQ ID NO:62). The gene was codon optimized for both yeast and E. coli with 5' sequence TCT GCT AGC (SEQ ID NO:48) and 3' sequence CTC GAG ATC TGA (SEQ ID NO:49).

In order to do homologous recombination in yeast, pCT302 overhangs were added to the synthesized library using forward primer 5'-CAGGCTAGTGGTGGTGGT-GGTTCTGGTGGTGGTGGTTCTGGTGGTGGTGGTTC TGCTAGCAATGCTGGTGTAACACAAACGCCAA-3' (SEQ ID NO: 50) and reverse primer 5'-GGAACAAAGTC-GATTTTGTTACATCTACACTGTTGTTAACAGATC-TCG AGTCATTATAAATCTTCTTCAGAGATC-3' (SEQ ID NO: 51). Yeast libraries were generated by homologous recombination in EBY100 yeast by electroporating PCR products along with NheI and XhoI digested pCT302 (Benatuil et al. (2010) Protein Eng Des Sel, 23, 155-9; Colby et al. (2004) Methods Enzymol, 388, 348-58; Starwalt et al. (2003) Protein Eng, 16, 147-56; Swers et al. (2004) Nucleic Acids Res, 32, e36). The resultant library size was $6 \times 10^6$. The library was induced in galactose-containing media (SG-CAA) for 48 h, washed with 1 mL 1% PBS/BSA, and stained with the following: anti-HA epitope tag (1:50), anti-Vα2 antibody (1:50), and tax or Mart1 peptide:HLA-A2 DimerX (100 nM) along with goat-anti-mouse IgG F(ab')$_2$ AlexaFluor 647 secondary antibody (1:100), and anti-cmyc (1:50) along with goat-anti-chicken IgG F(ab')$_2$ AlexaFluor 647 secondary antibody (1:100). Cells were washed (1 ml, 1% PBS/BSA), and the most fluorescent cells were selected using a FACS Aria (BD Bioscience) high-speed sorter. Selection was performed with tax:HLA-A2 dimer (10-20 nM) and Mart1:HLA-A2 dimer (20-500 nM).

Generation, Display, and Selection of RD-MART1 CDR3 Yeast Display Libraries

CDR3 libraries were generated by splicing by overlap extension (SOE) PCR spanning 5 adjacent codons at a time (2 libraries in the CDR3β loop; 1 in the CDR3α loop) (Horton et al. (1990) Biotechniques, 8, 528-35) using the RD1-MART1 scTV clone selected from the RD1 library as a template. Pre-SOE PCR products were generated for each of the four libraries utilizing the following primer pairs. β1: 5'-GGC AGC CCC ATA AAC ACA CAG TAT-3' (SEQ ID NO:52) (Splice 4L) and 5'-CGG ACG GGA AGC GCA GAA ATA CAC TGA GGT TTG AGA AGG TGC AGC GCT TAA CAG ACG CAG CGG-3' (SEQ ID NO:53), and 5'-ACC TCA GTG TAT TTC TGC GCT TCC CGT CCG NNKNNKNNKNNKNNK CAG CCT GAA CTG TAC TTT GGT CCA GGC ACT AGA C-3' (SEQ ID NO:54) and 5'-TAA TAC GAC TCA CTA TAG GG-3' (SEQ ID NO:55) (T7); β2: Splice 4L and 5'-CGG ACG GGA AGC GCA GAA ATA CAC TGA GGT TTG AGA AGG TGC AGC GCT TAA CAG ACG CAG CGG-3' (SEQ ID NO:56), and 5'-ACC TCA GTG TAT TTC TGC GCT TCC CGT CCG GGT TGG NNKNNKNNKNNKNNK GAA CTG TAC TTT GGT CCA GGC ACT AGA CTG ACC G-3' (SEQ ID NO:57) and T7; α: Splice 4L and 5'-CGT AAC CGC GCA CAA GTA TGT GGC CGA ATC GGA AGG CTG GGA GTC ACG AAT CAG CAA ACT AAC ATA CTG GC-3' (SEQ ID NO:58), and 5'-TCC GAT TCG GCC ACA TAC TTG TGC GCG GTT ACG NNKNNKNNKNNKNNK AAA CTG CAA TTT GGT GCG GGC ACC CAG GTT GTG G-3' (SEQ ID NO:59) and T7. SOE PCR was performed with each corresponding Pre-SOE along with both T7 and Splice 4L for each library.

Yeast libraries were generated by homologous recombination in EBY100 yeast by electroporation of PCR products along with NheI and XhoI digested yeast display vector pCT302 (Benatuil et al. (2010) Protein Eng Des Sel, 23, 155-9; Colby et al. (2004) Methods Enzymol, 388, 348-58; Starwalt et al. (2003) Protein Eng, 16, 147-56; Swers et al. (2004) Nucleic Acids Res, 32, e36). The resultant library sizes were β1: $2.1 \times 10^7$, β2: $1.7 \times 10^7$, and α: $1.1 \times 10^7$. Libraries were pooled in equal cell numbers in ratios reflecting relative diversity, and expanded in SD-CAA media.

The combined library was induced in galactose-containing media (SG-CAA) for 48 hours, washed with 1 mL 1% PBS/BSA, and stained with MART1/HLA.A2 DimerX, goat-anti-mouse IgG F(ab')2 AlexaFluor 647 secondary antibody (1:100). Cells were washed (1 ml, 1% PBS/BSA), and the most fluorescent cells were selected using a FACS Aria (BD Bioscience) high-speed sorter. Selection was performed with MART1/HLA-A2 dimer (1-200 nM). Expression was monitored with anti-HA epitope tag (1:50), goat-anti-mouse IgG F(ab')2 AlexaFluor 647 secondary antibody (1:100), and anti-cmyc (1:50), goat-anti-chicken IgG F(ab')2 AlexaFluor 647 secondary antibody (1:100).

A6 RD2 Library Design

PyMOL software (The PyMOL Molecular Graphics System, Version 1.5.0.4 Schrödinger, LLC) was used to overlay crystal structures of the A6:Tax/HLA.A2 complex (PDB: 1AO7) with crystal structures of the MART1/HLA.A2 (PDB: 1JF1) (Sliz et al. (2001) J Immunol, 167, 3276-84) and WT1/HLA.A2 (PDB: 3HPJ) (Borbulevych et al. (2010) Mol Immunol, 47, 2519-24). Visual inspection and rational design were used to select residue positions in the A6:Tax/HLA.A2 crystal structure that were in close proximity with MART1/HLA.A2 and WT1/HLA.A2 in the overlaid crystal structures. Five positions (TCRα D27, G29, and S99; TCRβ L99 and W100) were made degenerate based on NNK nucleic acid composition. The glutamine at the first position of Vα2 was omitted from synthesis. The TCRα Position Q31 was a binary position where either the wild type residue glutamine or threonine could be selected, and the positions 100-103 in CDRβ3, were binary where the four adjacent residues could be selected as A6 wild type (AGGR, SEQ ID NO:44) or A6-X15 (MSAQ, SEQ ID NO:45).

Generation, Display, and Selection of RD2 Yeast Display Library

The A6 RD2 library was expressed in yeast display plasmid pCT302 (Vβ-L-Vα) (Boder and Wittrup (1997) Nat. Biotech., 15, 553-557; Boder and Wittrup (2000) Methods Enzymol, 328, 430-44), which contains a galactose-inducible AGA2 fusion allowing for growth in Trp media. Induction of the scTv gene involves growth of the transformed EBY100 yeast cells to stationary phase in selection media followed by transfer to galactose-containing media. The A6 RD2 Library was synthesized by DNA2.0 (Menlo Park, Calif., USA) using the A6-X15 as a template. The construct consisted of the variable fragments attached by the linker region GSADDAKKDAAKKDGKS (SEQ ID NO:21) and N-terminal HA and C-terminal Cmyc epitope tags. The following gene was synthesized where positions indicated by "X" were made degenerate by NNK codons, the positions labeled "1234" were binary allowing for A6 wild type CDR3β loop AGGR (SEQ ID NO:44) or A6-X15 CDR3β loop MSAQ (SEQ ID NO:45), the position indicated by "#" was binary allowing for either wild type residue Q or mutated T, and positions indicated by "*" were stop codons: NAGVTQTPKFQVLKTGQSMTLQCAQDMNH-EYMAWYRQDPGMGLRLIHYSVGVGITDQGDVPD-GYKVSRSTTEDFPLRLLSAAPSQTSVYFCASRPGX-1234PELYFGPGT RLTVTEDLINGSADDAKKDAAKK-DGKSKEVEQNSGPLSVPEGAIASLNCTYSXRXS#SF-FWYRQYSGKSPELIMSIYSNGDKEDGRFTAQLNKA-SQYVSLLIRDSQPSDSATYLCAVTTDXXGKLQFG-AGTQVVVTPDIEQKLISEEDL** (SEQ ID NO:63). The gene was codon optimized for yeast, and the following flanking DNA sequences were added which contained overlap with the T7 and Splice4L cloning primers: N-terminal DNA sequence: 5'-GGC AGC CCC ATA AAC ACA CAG TAT GTT TTT AAG GAC AAT AGC TCG ACG ATT GAA GGT AGA TAC CCA TAC GAC GTT CCA GAC TAC GCT CTG CAG GCT AGT GGT GGT GGT GGT TCT GGT GGT GGT GGT TCT GGT GGT GGT GGT TCT GCT AGC-3' (SEQ ID NO:60), and C-terminal DNA sequence: 5'-CTC GAG ATC TGT TAA CAA CAG TGT AGA TGT AAC AAA ATC GAC TTT GTT CCC ACT GTA CTT TTA GCT CGT ACA AAA TAC AAT ATA CTT TTC ATT TCT CCG TAA ACA ACA TGT TTT CCC ATG TAA TAT CCT TTT CTA TTT TTC GTT CCG TTA CCA ACT TTA CAC ATA CTT TAT ATA GCT ATT CAC TTC TAT ACA CTA AAA AAC TAA GAC AAT TTT AAT TTT GCT GCC TGC CAT ATT TCA ATT TGT TAT AAA TTC CTA TAA TTT ATC CTA TTA GTA GCT AAA AAA AGA TGA ATG TGA ATC GAA TCC TAA GAG AAT TGA GCT CCA ATT CGC CCT ATA GTG AGT CGT ATT A-3' (SEQ ID NO:61). The delivered PCR product was amplified via PCR using the Splice4L and T7 primers, and yeast libraries were generated by homologous recombination in EBY100 yeast by electroporation of amplified PCR products along with NheI and XhoI digested yeast display vector pCT302 (Benatuil et al. (2010) Protein Eng Des Sel, 23, 155-9; Colby et al. (2004) Methods Enzymol, 388, 348-58; Starwalt et al. (2003) Protein Eng, 16, 147-56; Swers et al. (2004) Nucleic Acids Res, 32, e36). The resultant library size was $2.4 \times 10^8$.

The RD2 library was induced in galactose-containing media (SG-CAA) for 48 hours, washed with 1 mL 1% PBS/BSA, and stained with 5 μm Tax (SEQ ID NO:5) or MART1 (SEQ ID NO:7) peptide/HLA.A2 UV-exchanged HLA.A2 monomers (Rodenko et al. (2006) Nat Protoc, 1, 1120-32; Toebes et al. (2006) Nat Med, 12, 246-51). Magnetic bead selections were performed utilizing streptavidin MACS microbeads (Miltenyl Biotec), for a total of two selections using MACS LS columns on a QuadroMACS™ Separator (Miltenyl Biotec). Following two selections, the selected libraries was stained with the following: selecting peptide/HLA.A2 DimerX, goat-anti-mouse IgG F(ab')2 AlexaFluor 647 secondary antibody (1:100). Cells were washed (1 ml, 1% PBS/BSA), and the most fluorescent cells were selected using a FACS Aria (BD Bioscience) high-speed sorter. Selections were performed with 1 nM and 100 nM peptide/HLA.A2 for selecting cognate antigen Tax, and selecting, non-cognate antigen MART1, respectively. Expression was monitored with anti-HA epitope tag (1:50), goat-anti-mouse IgG F(ab')2 AlexaFluor 647 secondary antibody (1:100), and anti-cmyc (1:50), goat-anti-chicken IgG F(ab')2 AlexaFluor 647 secondary antibody (1:100).

Isolation and Staining of High Affinity Clones

Following the fourth sort with Tax:HLA-A2 and the fifth sort with Mart1:HLA-A2, single colonies were isolated by plating limiting dilutions. Colonies were expanded and induced in galactose-containing media (SG-CAA) for 48 h, washed with 1 mL 1% PBS/BSA, and stained with the following: anti-HA epitope tag (1:50), anti-Vα2 antibody (1:50), and tax or Mart1 peptide:HLA-A2 DimerX (100 nM) along with goat-anti-mouse IgG F(ab')$_2$ AlexaFluor 647 secondary antibody (1:100), and anti-cmyc (1:50) along with goat-anti-chicken IgG F(ab')$_2$ AlexaFluor 647 secondary antibody (1:100). Cells were washed (1 ml, 1% PBS/BSA) and analyzed on an Accuri C6 flow cytometer.

Plasmids were recovered using Zymoprep™ Yeast Plasmid Miniprep II (Zymo Research) and introduced back into E. coli via heat shock transformation into Subcloning Efficiency™ DH5α™ Competent Cells (Invitrogen). E. coli cells were expanded and plasmids were isolated using QIAprep Spin Miniprep Kit (Qiagen). Sequences of individual clones were determined by Sanger sequencing.

STATEMENTS REGARDING INCORPORATION BY REFERENCE AND VARIATIONS

All references cited herein, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the disclosure pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art or to use methods or materials that are in the state of the art without the specific inclusion of the methods or materials in the disclosure herein. For example, when a compound is claimed, it should be understood that compounds known in the prior art, including certain compounds disclosed in the references disclosed herein (particularly in referenced patent documents), are not intended to be included in the claim.

When a Markush group or other grouping is used herein, all individual members of the group and all combinations and subcombinations possible of the group are intended to be individually included in the disclosure.

Where the terms "comprise", "comprises", "comprised", or "comprising" are used herein, they are to be interpreted as specifying the presence of the stated features, integers, steps, or components referred to, but not to preclude the presence or addition of one or more other feature, integer, step, component, or group thereof. Separate embodiments of the disclosure are also intended to be encompassed wherein the terms "comprising" or "comprise(s)" or "comprised" are optionally replaced with the terms, analogous in grammar, e.g.; "consisting/consist(s)" or "consisting essentially of/consist(s) essentially of" to thereby describe further embodiments that are not necessarily coextensive. For clarification, as used herein "comprising" is synonymous with "having," "including," "containing," or "characterized by," and is inclusive or open-ended and does not exclude additional, unrecited elements or method steps. As used herein, "consisting of" excludes any element, step, component, or ingredient not specified in the claim element. As used herein, "consisting essentially of" does not exclude materials or steps that do not materially affect the basic and novel characteristics of the claim (e.g., not affecting an active ingredient). In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

The disclosure has been described with reference to various specific and preferred embodiments and techniques. However, it should be understood that many variations and modifications may be made while remaining within the spirit and scope of the disclosure. It will be appreciated by one of ordinary skill in the art that compositions, methods, devices, device elements, materials, optional features, procedures and techniques other than those specifically described herein can be applied to the practice of the disclosure as broadly disclosed herein without resort to undue experimentation. All art-known functional equivalents of compositions, methods, devices, device elements, materials, procedures and techniques described herein; and portions thereof; are intended to be encompassed by this disclosure. Whenever a range is disclosed, all subranges and individual values are intended to be encompassed. This disclosure is not to be limited by the embodiments disclosed, including any shown in the drawings or exemplified in the specification, which are given by way of example or illustration and not of limitation.

Some references provided herein are incorporated by reference herein to provide details concerning additional starting materials, additional methods of synthesis, and additional methods of analysis and additional uses of the disclosure.

One skilled in the art would readily appreciate that the present disclosure is well adapted to carry out the objects and obtain the ends and advantages mentioned, as well as those inherent therein. The compositions and methods and accessory methods described herein as presently representative of preferred embodiments are exemplary and are not intended as limitations on the scope of the disclosure. Changes therein and other uses will occur to those skilled in the art, which are encompassed within the spirit of the disclosure.

REFERENCES

1. Addo M. M., Draenert R., Rathod A., Verrill C. L., Davis B. T., Gandhi R. T., Robbins G. K., Basgoz N. O., Stone D. R., Cohen D. E., Johnston M. N., Flynn T., Wurcel A. G., Rosenberg E. S., Altfeld M. and Walker B. D. (2007) Fully Differentiated HIV-1 Specific CD8+T Effector Cells Are More Frequently Detectable in Controlled than in Progressive HIV-1 Infection. *PLoS ONE* 2, e321.
2. Aggen D. H., Chervin A. S., Insaidoo F. K., Piepenbrink K., H., Baker B. M. and Kranz D. M. (2011) Identification and engineering of human variable regions that allow expression of stable single-chain T cell receptors. *Protein Engineering, Design, & Selection* 24, 361-72.
3. Anikeeva N., Mareeva T., Liu W. and Sykulev Y. (2009) Can oligomeric T-cell receptor be used as a tool to detect viral peptide epitopes on infected cells? *Clin Immunol* 130, 98-109.
4. Armstrong K. M., Piepenbrink K. H. and Baker B. M. (2008) Conformational changes and flexibility in T-cell receptor recognition of peptide-MHC complexes. *Biochem J* 415, 183-96.
5. Ashfield R. and Jakobsen B. K. (2006) Making high-affinity T-cell receptors: a new class of targeted therapeutics. *IDrugs* 9, 554-9.
6. Bargou R., Leo E., Zugmaier G., Klinger M., Goebeler M., Knop S., Noppeney R., Viardot A., Hess G., Schuler M., Einsele H., Brandi C., Wolf A., Kirchinger P., Klappers P., Schmidt M., Riethmuller G., Reinhardt C., Baeuerle P. A. and Kufer P. (2008) Tumor regression in cancer patients by very low doses of a T cell-engaging antibody. *Science* 321, 974-7.
7. Benatuil L., Perez J. M., Belk J. and Hsieh C. M. (2010) An improved yeast transformation method for the generation of very large human antibody libraries. *Protein Eng Des Sel* 23, 155-9.
8. Bird R. E., Hardman K. D., Jacobson J. W., Johnson S., Kaufman B. M., Lee S. M., Lee T., Pope S. H., Riordan G. S. and Whitlow M. (1988) Single-chain antigen-binding proteins. *Science* 242, 423-426.
9. Boder E. T. and Wittrup K. D. (1997) Yeast surface display for screening combinatorial polypeptide libraries. *Nat. Biotech.* 15, 553-557.
10. Boder E. T. and Wittrup K. D. (2000) Yeast surface display for directed evolution of protein expression, affinity, and stability. *Methods Enzymol* 328, 430-44.
11. Boon T. and Old L. J. (1997) Cancer tumor antigens. *Curr Opin Immunol* 9, 681-3.
12. Borbulevych O. Y., Do P. and Baker B. M. (2010) Structures of native and affinity-enhanced WT1 epitopes bound to HLA-A*0201: implications for WT1-based cancer therapeutics. *Mol Immunol* 47, 2519-24.

13. Borbulevych O. Y., Santhanagopolan S. M., Hossain M. and Baker B. M. (2011) TCRs used in cancer gene therapy cross-react with MART-1/Melan-A tumor antigens via distinct mechanisms. *J Immunol* 187, 2453-63.
14. Brower V. (1997) Enbrel's phase III reinforces prospects in RA [news]. *Nat Biotechnol* 15, 1240.
15. Bulek A. M., Cole D. K., Skowera A., Dolton G., Gras S., Madura F., Fuller A., Miles J. J., Gostick E., Price D. A., Drijfhout J. W., Knight R. R., Huang G. C., Lissin N., Molloy P. E., Wooldridge L., Jakobsen B. K., Rossjohn J., Peakman M., Rizkallah P. J. and Sewell A. K. (2012) Structural basis for the killing of human beta cells by CD8(+) T cells in type 1 diabetes. *Nat Immunol* 13, 283-9.
16. Cheever M. A., Allison J. P., Ferris A. S., Finn O. J., Hastings B. M., Hecht T. T., Mellman I., Prindiville S. A., Viner J. L., Weiner L. M. and Matrisian L. M. (2009) The prioritization of cancer antigens: a national cancer institute pilot project for the acceleration of translational research. *Clin Cancer Res* 15, 5323-37.
17. Chervin A. S., Aggen D. H., Raseman J. M. and Kranz D. M. (2008) Engineering higher affinity T cell receptors using a T cell display system. *J Immunol Methods* 339, 175-84.
18. Colby D. W., Kellogg B. A., Graff C. P., Yeung Y. A., Swers J. S. and Wittrup K. D. (2004) Engineering antibody affinity by yeast surface display. *Methods Enzymol* 388, 348-58.
19. Davis M. M. and Bjorkman P. J. (1988) T-cell antigen receptor genes and T-cell recognition. *Nature* 334, 395-402.
20. Davis M. M., Boniface J. J., Reich Z., Lyons D., Hampl J., Arden B. and Chien Y. (1998) Ligand recognition by alpha beta T cell receptors. *Annu Rev Immunol* 16, 523-544.
21. Ding Y. H., Baker B. M., Garboczi D. N., Biddison W. E. and Wiley D. C. (1999) Four A6-TCR/peptide/HLA-A2 structures that generate very different T cell signals are nearly identical. *Immunity* 11, 45-56.
22. Fleischer K., Schmidt B., Kastenmuller W., Busch D. H., Drexler I., Sutter G., Heike M., Peschel C. and Bernhard H. (2004) Melanoma-reactive class I-restricted cytotoxic T cell clones are stimulated by dendritic cells loaded with synthetic peptides, but fail to respond to dendritic cells pulsed with melanoma-derived heat shock proteins in vitro. *J Immunol* 172, 162-9.
23. Foote J. and Eisen H. N. (2000) Breaking the affinity ceiling for antibodies and T cell receptors. *Proc Natl Acad Sci USA* 97, 10679-81.
24. Garboczi D. N., Ghosh P., Utz U., Fan Q. R., Biddison W. E. and Wiley D. C. (1996) Structure of the complex between human T-cell receptor, viral peptide and HLA-A2. *Nature* 384, 134-141.
25. Garcia K. C., Adams J. J., Feng D. and Ely L. K. (2009) The molecular basis of TCR germline bias for MHC is surprisingly simple. *Nat Immunol* 10, 143-7.
26. Haidar J. N., Pierce B., Yu Y., Tong W., Li M. and Weng Z. (2009) Structure-based design of a T-cell receptor leads to nearly 100-fold improvement in binding affinity for pepMHC. *Proteins* 74, 948-60.
27. Harkiolaki M., Holmes S. L., Svendsen P., Gregersen J. W., Jensen L. T., McMahon R., Friese M. A., van Boxel G., Etzensperger R., Tzartos J. S., Kranc K., Sainsbury S., Harlos K., Mellins E. D., Palace J., Esiri M. M., van der Merwe P. A., Jones E. Y. and Fugger L. (2009) T cell-mediated autoimmune disease due to low-affinity cross-reactivity to common microbial peptides. *Immunity* 30, 348-57.
28. Hawse W. F., Champion M. M., Joyce M. V., Hellman L. M., Hossain M., Ryan V., Pierce B. G., Weng Z. and Baker B. M. (2012) Cutting edge: evidence for a dynamically driven T cell signaling mechanism. *J Immunol* 188, 5819-23.
29. Holler P. D., Chlewicki L. K. and Kranz D. M. (2003) TCRs with high affinity for foreign pMHC show self-reactivity. *Nat Immunol* 4, 55-62.
30. Holler P. D., Holman P. O., Shusta E. V., O'Herrin S., Wittrup K. D. and Kranz D. M. (2000) In vitro evolution of a T cell receptor with high affinity for peptide/MHC. *Proc Natl Acad Sci USA* 97, 5387-92.
31. Holliger P., Prospero T. and Winter G. (1993) "Diabodies": small bivalent and bispecific antibody fragments. *Proc Natl Acad Sci USA* 90, 6444-8.
32. Hoogenboom H. R. (2005) Selecting and screening recombinant antibody libraries. *Nat Biotechnol* 23, 1105-16.
33. Horton R. M., Cal Z. L., Ho S. N. and Pease L. R. (1990) Gene splicing by overlap extension: tailor-made genes using the polymerase chain reaction. *Biotechniques* 8, 528-35.
34. Jarvis L. M. (2012) Rethinking Antibody-Drug Conjugates. *Chemical and Engineering News* 90, 12-18.
35. Kessels H. W., van Den Boom M. D., Spits H., Hooijberg E. and Schumacher T. N. (2000) Changing T cell specificity by retroviral T cell receptor display. *Proc Natl Acad Sci USA* 97, 14578-83.
36. Kieke M. C., Shusta E. V., Bader E. T., Teyton L., Wittrup K. D. and Kranz D. M. (1999) Selection of functional T cell receptor mutants from a yeast surface-display library. *Proc Natl Acad Sci USA* 96, 5651-6.
37. Lauck F., Smith C. A., Friedland G. F., Humphris E. L. and Kortemme T. (2010) RosettaBackrub—a web server for flexible backbone protein structure modeling and design. *Nucleic Acids Res* 38, W569-75.
38. Li Y., Moysey R., Molloy P. E., Vuidepot A. L., Mahon T., Baston E., Dunn S., Liddy N., Jacob J., Jakobsen B. K. and Boulter J. M. (2005) Directed evolution of human T-cell receptors with picomolar affinities by phage display. *Nat Biotechnol* 23, 349-54.
39. Liddy N., Bossi G., Adams K. J., Lissina A., Mahon T. M., Hassan N. J., Gavarret J., Bianchi F. C., Pumphrey N. J., Ladell K., Gostick E., Sewell A. K., Lissin N. M., Harwood N. E., Molloy P. E., Li Y., Cameron B. J., Sami M., Baston E. E., Todorov P. T., Pastor'S. J., Dennis R. E., Harper J. V., Dunn S. M., Ashfield R., Johnson A., McGrath Y., Plesa G., June C. H., Kalos M., Price D. A., Vuidepot A., Williams D. D., Sutton D. H. and Jakobsen B. K. (2012) Monoclonal TCR-redirected tumor cell killing. *Nat Med* 18, 980-7.
40. Litvak-Greenfeld D. and Benhar I. (2012) Risks and untoward toxicities of antibody-based immunoconjugates. *Adv Drug Deliv Rev.*
41. Manning T. C. and Kranz D. M. (1999) Binding energetics of T-cell receptors: correlation with immunological consequences. *Immunology Today* 20, 417-422.
42. Marrack P., Scott-Browne J. P., Dai S., Gapin L. and Kappler J. W. (2008) Evolutionarily conserved amino acids that control TCR-MHC interaction. *Annu Rev Immunol* 26, 171-203.
43. Marsh S. G. E., Parham P. and Barber L. D. (2000) *The HLA Facts Book*. Academic Press, London.
44. Mason D. (1998) A very high level of crossreactivity is an essential feature of the T-cell receptor. *Immunol Today* 19, 395-404.

45. Miller B. R., Demarest S. J., Lugovskoy A., Huang F., Wu X., Snyder W. B., Croner L. J., Wang N., Amatucci A., Michaelson J. S. and Glaser S. M. (2010) Stability engineering of scFvs for the development of bispecific and multivalent antibodies. *Protein Eng Des Sel* 23, 549-57.
46. Molloy P. E., Sewell A. K. and Jakobsen B. K. (2005) Soluble T cell receptors: novel immunotherapies. *Curr Opin Pharmacol* 5, 438-43.
47. Murphy K. (2012) *Janeway's immunobiology*. Garland Science, New York.
48. Nold M. F., Nold-Petry C. A., Zepp J. A., Palmer B. E., Butler P. and Dinarello C. A. (2010) IL-37 is a fundamental inhibitor of innate immunity. *Nat Immunol* 11, 1014-22.
49. Pastan I., Hassan R., Fitzgerald D. J. and Kreitman R. J. (2006) Immunotoxin therapy of cancer. *Nat Rev Cancer* 6, 559-65.
50. Pierce B. G., Haidar J. N., Yu Y. and Weng Z. (2010) Combinations of affinity-enhancing mutations in a T cell receptor reveal highly nonadditive effects within and between complementarity determining regions and chains. *Biochemistry* 49, 7050-9.
51. Porter D. L., Levine B. L., Kalos M., Bagg A. and June C. H. (2011) Chimeric antigen receptor-modified T cells in chronic lymphoid leukemia. *N Engl J Med* 365, 725-33.
52. Reichert J. M. and Valge-Archer V. E. (2007) Development trends for monoclonal antibody cancer therapeutics. *Nat Rev Drug Discov* 6, 349-56.
53. Ricart A. D. and Tolcher A. W. (2007) Technology insight: cytotoxic drug immunoconjugates for cancer therapy. *Nat Clin Pract Oncol* 4, 245-55.
54. Richman S. A., Aggen D. H., Dossett M. L., Donermeyer D. L., Allen P. M., Greenberg P. D. and Kranz D. M. (2009) Structural features of T cell receptor variable regions that enhance domain stability and enable expression as single-chain ValphaVbeta fragments. *Mol Immunol* 46, 902-16.
55. Richman S. A. and Kranz D. M. (2007) Display, engineering, and applications of antigen-specific T cell receptors. *Biomol Eng* 24, 361-73.
56. Rock K. L. and Goldberg A. L. (1999) Degradation of cell proteins and the generation of MHC class I-presented peptides. *Annu Rev Immunol* 17, 739-79.
57. Rodenko B., Toebes M., Hadrup S. R., van Esch W. J., Molenaar A. M., Schumacher T. N. and Ovaa H. (2006) Generation of peptide-MHC class I complexes through UV-mediated ligand exchange. *Nat Protoc* 1, 1120-32.
58. Rudolph M. G., Stanfield R. L. and Wilson L A. (2006) How TCRs bind MHCs, peptides, and coreceptors. *Annu Rev Immunol* 24, 419-66.
59. Sadelain M., Brentjens R. and Riviere L (2009) The promise and potential pitfalls of chimeric antigen receptors. *Curr Opin Immunol* 21, 215-23.
60. Sami M., Rizkallah P. J., Dunn S., Molloy P., Moysey R., Vuidepot A., Baston E., Todorov P., Li Y., Gao F., Boulter J. M. and Jakobsen B. K. (2007) Crystal structures of high affinity human T-cell receptors bound to peptide major histocompatibility complex reveal native diagonal binding geometry. *Protein Eng Des Sel* 20, 397-403.
61. Schrama D., Reisfeld R. A. and Becker J. C. (2006) Antibody targeted drugs as cancer therapeutics. *Nat Rev Drug Discov* 5, 147-59.
62. Scott J. K. and Smith G. P. (1990) Searching for peptide ligands with an epitope library. *Science* 249, 386-90.
63. Skowera A., Ellis R. J., Varela-Calvino R., Arif S., Huang G. C., Van-Krinks C., Zaremba A., Rackham C., Allen J. S., Tree T. I., Zhao M., Dayan C. M., Sewell A. K., Unger W. W., Drijfhout J. W., Ossendorp F., Roep B. O. and Peakman M. (2008) CTLs are targeted to kill beta cells in patients with type 1 diabetes through recognition of a glucose-regulated preproinsulin epitope. *J Clin Invest* 118, 3390-402.
64. Sliz P., Michielin O., Cerottini J. C., Luescher I., Romero P., Karplus M. and Wiley D. C. (2001) Crystal structures of two closely related but antigenically distinct HLA-A2/melanocyte-melanoma tumor-antigen peptide complexes. *J Immunol* 167, 3276-84.
65. Smith C. A. and Kortemme T. (2008) Backrub-like backbone simulation recapitulates natural protein conformational variability and improves mutant side-chain prediction. *J Mol Biol* 380, 742-56.
66. Soo Hoo W. F., Lacy M. J., Denzin L. K., Voss E. W. J., Hardman K. D. and Kranz D. M. (1992) Characterization of a single-chain T cell receptor expressed in E. Coll. *Proc. Natl. Acad. Sci.* 89, 4759-4763.
67. Starr T. K., Jameson S. C. and Hogquist K. A. (2003) Positive and negative selection of T cells. *Annu Rev Immunol* 21, 139-76.
68. Starwalt S. E., Masteller E. L., Bluestone J. A. and Kranz D. M. (2003) Directed evolution of a single-chain class II MHC product by yeast display. *Protein Eng* 16, 147-56.
69. Stone J. D., Chervin A. S., Aggen D. H. and Kranz D. M. (2012) T cell receptor engineering. *Methods Enzymol* 503, 189-222.
70. Stone J. D., Yin Y., Mo M., Weber K. S., Donermeyer D. L., Allen P. M., Mariuzza R. A. and Kranz D. M. (2012) Engineering High-Affinity T Cell Receptor/Cytokine Fusions for Therapeutic Targeting. In *Protein Engineering* (Edited by Kaumaya P.). InTech.
71. Stroncek D. F., Berger C., Cheever M. A., Childs R. W., Dudley M. E., Flynn P., Gattinoni L., Heath J. R., Kalos M., Marincola F. M., Miller J. S., Mostoslaysky G., Powell D. J., Jr., Rao M., Restifo N. P., Rosenberg S. A., O'Shea J. and Melief C. J. (2012) New directions in cellular therapy of cancer: a summary of the summit on cellular therapy for cancer. *J Trans Med* 10, 48.
72. Swers J. S., Kellogg B. A. and Wittrup K. D. (2004) Shuffled antibody libraries created by in vivo homologous recombination and yeast surface display. *Nucleic Acids Res* 32, e36.
73. Tayal V. and Kalra B. S. (2008) Cytokines and anti-cytokines as therapeutics—an update. *Eur J Pharmacol* 579, 1-12.
74. Thakur A. and Lum L. G. (2010) Cancer therapy with bispecific antibodies: Clinical experience. *Curr Opin Mol Ther* 12, 340-9.
75. Toebes M., Coccoris M., Bins A., Rodenko B., Gomez R., Nieuwkoop N. J., van de Kasteele W., Rimmelzwaan G. F., Haanen J. B., Ovaa H. and Schumacher T. N. (2006) Design and use of conditional MHC class I ligands. *Nat Med* 12, 246-51.
76. Tonegawa S. (1988) Nobel lecture in physiology or medicine—1987. Somatic generation of immune diversity. *In Vitro Cell Dev Biol* 24, 253-65.
77. Tsomides T. J., Aldovini A., Johnson R. P., Walker B. D., Young R. A. and Eisen H. N. (1994) Naturally processed viral peptides recognized by cytotoxic T lymphocytes on cells chronically infected by human immunodeficiency virus type 1. *J Exp Med* 180, 1283-93.
78. Turner D. J., Ritter M. A. and George A. J. (1997) Importance of the linker in expression of single-chain Fv antibody fragments: optimisation of peptide sequence using phage display technology. *J Immunol Methods* 205, 43-54.

79. Utz U., Banks D., Jacobson S. and Biddison W. E. (1996) Analysis of the T-cell receptor repertoire of human T-cell leukemia virus type 1 (HTLV-1) Tax-specific CD8+ cytotoxic T lymphocytes from patients with HTLV-1-associated disease: evidence for oligoclonal expansion. *J Virol* 70, 843-51.
80. Varela-Rohena A., Molloy P. E., Dunn S. M., Li Y., Suhoski M. M., Carroll R. G., Milicic A., Mahon T., Sutton D. H., Laugel B., Moysey R., Cameron B. J., Vuidepot A., Purbhoo M. A., Cole D. K., Phillips R. E., June C. H., Jakobsen B. K., Sewell A. K. and Riley J. L. (2008) Control of HIV-1 immune escape by CD8 T cells expressing enhanced T-cell receptor. *Nat Med* 14, 1390-5.
81. Weber K. S., Donermeyer D. L., Allen P. M. and Kranz D. M. (2005) Class II-restricted T cell receptor engineered in vitro for higher affinity retains peptide specificity and function. *Proc Natl Acad Sci USA* 102, 19033-8.
82. Wong R. L., Liu B., Zhu X., You L., Kong L., Han K. P., Lee H. I., Chavaillaz P. A., Jin M., Wang Y., Rhode P. R. and Wong H. C. (2011) Interleukin-15:Interleukin-15 receptor alpha scaffold for creation of multivalent targeted immune molecules. *Protein Eng Des Sel* 24, 373-83.
83. Zhang B., Bowerman N. A., Salama J. K., Schmidt H., Spiotto M. T., Schietinger A., Yu P., Fu Y. X., Weichselbaum R. R., Rowley D. A., Kranz D. M. and Schreiber H. (2007) Induced sensitization of tumor stroma leads to eradication of established cancer by T cells. *J Exp Med* 204, 49-55.

U.S. Patents

U.S. Pat. No. 7,569,357; Filed 20 Feb. 2004; Issued 4 Aug. 2009; Board of Trustees University of Illinois. High affinity TCR proteins and methods.
U.S. Pat. No. 7,465,787; Filed 16 Dec. 2003; Issued 16 Dec. 2008; Board of Trustees University of Illinois. Yeast cell surface display of proteins and uses thereof.
U.S. Pat. No. 6,759,243; Filed 6 Dec. 2000; Issued 6 Jul. 2004; Board of Trustees University of Illinois. High affinity TCR proteins and methods.
U.S. Pat. No. 6,699,658; Filed 20 Jan. 1998; Issued 2 Mar. 2004; Board of Trustees University of Illinois. Yeast cell surface display of proteins and uses thereof.
U.S. Pat. No. 6,696,251; Filed 28 Nov. 2000; Issued 24 Feb. 2004; Board of Trustees University of Illinois. Yeast cell surface display of proteins and uses thereof.
U.S. Pat. No. 6,423,538; Filed 28 Nov. 2000; Issued 23 Jul. 2002; Board of Trustees University of Illinois. Yeast cell surface display of proteins and uses thereof.
U.S. Pat. No. 6,300,065; Filed 26 Aug. 1998; Issued 9 Oct. 2001; Board of Trustees University of Illinois. Yeast cell surface display of proteins and uses thereof.
U.S. Pat. No. 8,143,376; Filed 18 May 2005; Issued 27 Mar. 2012; Immunocore Limited; High affinity NY-ESO T cell receptor.
U.S. Pat. No. 8,088,379; Filed 26 Sep. 2007; Issued 3 Jan. 2012; Immunocore Limited; Modified T cell receptors and related materials and methods.
U.S. Pat. No. 8,017,730; Filed 19 May 3006; Issued 13 Sep. 2011; Immunocore Limited; T cell receptors which bind to antigen-HLA-A24.
U.S. Pat. No. 7,763,718; Filed 29 Oct. 2007; Issued 27 Jul. 2010; Immunocore Limited; Soluble T cell receptors.
U.S. Pat. No. 7,666,604; Filed 9 Jul. 2003; Issued 23 Feb. 2010; Immunocore Limited; Modified soluble T cell receptor.
U.S. Pat. No. 7,608,410; Filed 7 Oct. 2008; Issued 27 Oct. 2009; Immunocore Limited; Method of improving T cell receptors.
U.S. Pat. No. 7,569,664; Filed 3 Oct. 2003; Issued 4 Aug. 2009; Immunocore Limited; Single chain recombinant T cell receptors.
U.S. Pat. No. 8,105,830; Filed 5 Nov. 2002; Issued 31 Jan. 2012; Altor Bioscience Corporation; Polyspecific binding molecules and uses thereof.
U.S. Pat. No. 6,534,633; Filed 21 Oct. 1999; 18 Mar. 2003; Altor Bioscience Corporation; Polyspecific binding molecules and uses thereof.

The invention claimed is:

1. A method for engineering a T cell receptor, the method comprising:
    a) isolating a polynucleotide that encodes a wild type T cell receptor, wherein the wild type T cell receptor is a single-chain T cell receptor A6-X15 comprising the amino acid sequence set forth in SEQ ID NO:3;
    b) generating a library of mutant T cell receptors, wherein the mutant T cell receptors comprise a mutation in one or more complementarity determining regions relative to the wild type T cell receptor;
    c) expressing the mutant T cell receptors in a surface display system; and
    d) measuring the binding of the mutant T cell receptors to a non-cognate peptide-MHC, in order to select mutant T cell receptors that bind to the non-cognate peptide-MHC,
    wherein the non-cognate peptide-MHC is SURV: HLA.A2.

2. The method of claim 1 wherein the wild type T cell receptor comprises the Vα amino acid sequence set forth in SEQ ID NO:1 and the Vβ amino acid sequence set forth in SEQ ID NO:2.

3. The method of claim 1 wherein the surface display system is a yeast display system.

4. The method of claim 1, further comprising a step of affinity maturation.

5. The method of claim 1, wherein the mutation comprises an amino acid substitution at one or more of CDR1α 31, CDR3α 98, CDR3β 99, CDR3α 97, CDR3β 102, CDR3α 99, CDR3β 100, CDR1α 32, CDR1β 30, CDR3β 101 and CDR3β 98.

6. A method for engineering a T cell receptor, the method comprising:

a) isolating a polynucleotide that encodes a wild type T cell receptor, wherein the wild type T cell receptor is a single-chain T cell receptor A6-X15 comprising the amino acid sequence set forth in SEQ ID NO:3;

b) generating a library of mutant T cell receptors, wherein the library comprises a plurality of mutant T cell receptors, each comprising a mutation in one or more complementarity determining regions relative to the wild type T cell receptor;

c) expressing the mutant T cell receptors in a surface display system; and d) measuring the binding of the mutant T cell receptors to a non-cognate peptide-MHC, in order to select mutant T cell receptors that bind to the non-cognate peptide-MHC.

7. The method of claim 6 wherein the surface display system is a yeast display system.

8. The method of claim 6, wherein the mutation comprises an amino acid substitution at one or more of CDR1α 31, CDR3α 98, CDR3β 99, CDR3α 97, CDR3β 102, CDR3α 99, CDR3β 100, CDR1α 32, CDR1β 30, CDR3β 101 and CDR3β 98.

* * * * *